US012685782B2

(12) United States Patent
Bunin et al.

(10) Patent No.: US 12,685,782 B2
(45) Date of Patent: Jul. 21, 2026

(54) BIFUNCTIONAL DEGRADERS FOR THE TREATMENT OF GRAVES' DISEASE

(71) Applicant: Biohaven Therapeutics Ltd., New Haven, CT (US)

(72) Inventors: Anna Bunin, Queens, NY (US); Seong Lee, West Haven, CT (US); Kathren Croce, New Haven, CT (US); Miranda L. Simes, Somerville, MA (US); Edward Deramon, Hamden, CT (US); Mariano Oppikofer, Stamford, CT (US)

(73) Assignee: Biohaven Therapeutics Ltd., Tortola (VG)

( * ) Notice: Subject to any disclaimer, the term of this patent is extended or adjusted under 35 U.S.C. 154(b) by 0 days.

(21) Appl. No.: 19/253,824

(22) Filed: Jun. 28, 2025

(65) Prior Publication Data

US 2026/0034231 A1 Feb. 5, 2026

Related U.S. Application Data

(60) Provisional application No. 63/677,437, filed on Jul. 31, 2024.

(51) Int. Cl.
*A61K 47/68* (2017.01)
*C07K 16/28* (2006.01)

(52) U.S. Cl.
CPC ...... *A61K 47/6849* (2017.08); *A61K 47/6803* (2017.08); *C07K 16/2869* (2013.01); *C07K 2317/92* (2013.01)

(58) Field of Classification Search
CPC ................................................. C07K 2319/30
See application file for complete search history.

(56) References Cited

U.S. PATENT DOCUMENTS

2016/0175458 A1* 6/2016 Alvarez .................... A61P 7/04 435/219
2022/0098242 A1* 3/2022 Zhu ........................ A61K 39/12

FOREIGN PATENT DOCUMENTS

| | | | | | |
|---|---|---|---|---|---|
| CN | 111330013 | A | | 6/2020 | |
| WO | 2008/025991 | A1 | | 3/2008 | |
| WO | 2015/189543 | A2 | | 12/2015 | |
| WO | WO-2018075308 | A1 | * | 4/2018 | .............. A61P 35/00 |
| WO | 2021/142377 | A2 | | 7/2021 | |
| WO | 2022/157626 | A1 | | 7/2022 | |
| WO | WO-2022260659 | A1 | * | 12/2022 | .............. A61P 35/00 |
| WO | 2023/288033 | A1 | | 1/2023 | |
| WO | 2024/155750 | A1 | | 7/2024 | |
| WO | 2025/030000 | A1 | | 2/2025 | |
| WO | 2025/207934 | A1 | | 10/2025 | |

OTHER PUBLICATIONS

Pyzik, Nature Reviews Immunology, 2023, vol. 23, pp. 415-432 (Year: 2023).*
Liu and May (mAbs, 2012, vol. 4, pp. 17-23). (Year: 2012).*
Jai Prakash et al. "Tumor-targeted intracellular delivery of anticancer drugs through the mannose-6-phosphate/insulin-like growth factor receptor" International Journal of Cancer, 2009, 126(8), 1966-1981.
Jennifer Miller-Gallacher et al. "Crystal structure of a ligand-free stable TSH receptor leucine-rich repeat domain" Journal of Molecular Endocrinology, 2019, 62, 117-128.

* cited by examiner

*Primary Examiner* — Karen A. Canella

(57) ABSTRACT

A composition of matter including an anti-TSH receptor autoantibody-binding moiety, a cellular receptor-binding moiety that binds to hepatocytes or other degrading cells through asialoglycoprotein receptors (ASGPR) on the surface of hepatocytes or other degrading cells in a patient or subject, and optionally, a linker moiety connecting the anti-TSH receptor autoantibody-binding moiety and the cellular receptor-binding moiety, wherein the composition of matter is useful for removing anti-TSH receptor autoantibody from a patient or subject, such as a Graves' disease patient.

5 Claims, 25 Drawing Sheets

Specification includes a Sequence Listing.

- Autoantibodies bind the extracellular LRD domain of TSHR.
- Antibody binding overlaps with that of the native ligand, TSH.

selected as bait for degrader.

LRD = Leucine Rich Domain
TSHR = Thyroid-Stimulating Hormone Receptor
TSH = Thyroid-Stimulating Hormone ASGPR Binder
Trimeric Beta-GaLNAc (BGN3)

MATCH TO FIG. 2

Payload, DAR2

TBT301

Endocytosis cellular assay

- HEK293-ASGPR1 cell line
- M22 directly conjucated to AlexaFluor-647
- FA, fluorescence area
- $EC_{50}$ fitting limited to [Ligand] > 34 nM
- Data points are mean ± SEM from two technical replicates

• 8 mpk dose achieved higher $C_{MAX}$ than 3 mpk.
• AGN301 (3 mpk IV) achieved ~95% depletion of M22
• Both doses achieved similar M22 reduction.
• No rebound of M22 was observed.

8 mpk = ~500:1 D:T
3 mpk = ~200:1 D:T

- Both doses of AGN301 (3 and 8 mpk) achieved robust depletion of M22, ~95%
- Both doses achieved similar M22 reduction.
- No rebound of M22 was observed.

• All dose levels tested, 3, 0.3, and 0.1 mpk, successfully depleted > 90% M22

• AGN301 maintains potent activity at a dose level of 0.1 mpk

| TABLE 1<br>R-Groups for MATE reagents and bifunctional MoDE final components | |
|---|---|
| MAT01A |  |

TABLE 1
R-Groups for MATE reagents and bifunctional MoDE final components

| | |
|---|---|
| MAT018 |  |

TABLE 1
R-Groups for MATE reagents and bifunctional MoDE final components

| | |
|---|---|
| MATOIC |  |

TABLE 1
R-Groups for MATE reagents and bifunctional MoDE final components

| | |
|---|---|
| MAT010 |  |

TABLE 1
R-Groups for MATE reagents and bifunctional MoDE final components

| | |
|---|---|
| MATOIE |  |
| MATOIF |  |

TABLE 1
R-Groups for MATE reagents and bifunctional MoDE final components

| | |
|---|---|
| MATOIG |  |

TABLE 1
R-Groups for MATE reagents and bifunctional MoDE final components

| | |
|---|---|
| MAT01H |  |
| MAT01I |  |
| MAT01J |  |
| MAT01K |  |

FcIII-GN3

```
     CH1 →
IGG1 ASTKGPSVFP LAPSSKSTSG GTAALGCLVK DYFPEPVTVS WNSGALTSGV HTFPAVLQSS GLYSLSSVVT 187
IGG2 ASTKGPSVFP LAPCSRSTSE STAALGCLVK DYFPEPVTVS WNSGALTSGV HTFPAVLQSS GLYSLSSVVT
IGG4 ASTKGPSVFP LAPCSRSTSE STAALGCLVK DYFPEPVTVS WNSGALTSGV HTFPAVLQSS GLYSLSSVVT

                                                                     P247I
                                                 CH2 →       S239D   |   T250Q
IGG1 VPSSSLGTQT YICNVNHKPS NTKVDKKVEP KSCDKTHTCP PCPAPELLGG PSVFLFPPKP KDTLMISRTP 257
IGG2 VPSSNFGTQT YTCNVDHKPS NTKVDKTVER KCCV---ECP PCPAPPVA-G PSVFLFPPKP KDTLMISRTP
IGG4 VPSSSLGTKT YTCNVDHKPS NTKVDKRVES KYGP---PCP SCPAPEFLGG PSVFLFPPKP KDTLMISRTP
                                  (HINGE)      (LOWER HINGE)           M252Y/S254T/T256E

                                           N297
IGG1 EVTCVVVDVS HEDPEVKFNW YVDGVEVHNA KTKPREEQYN STYRVVSVLT VLHQDWLNGK EYKCKVSNKA 327
IGG2 EVTCVVVDVS HEDPEVQFNW YVDGVEVHNA KTKPREEQFN STFRVVSVLT VVHQDWLNGK EYKCKVSNKG
IGG4 EVTCVVVDVS QEDPEVQFNW YVDGVEVHNA KTKPREEQFN STYRVVSVLT VLHQDWLNGK EYKCKVSNKG
                                            S298A

     A330L     A339D/Q
     | I332E   |  CH3 →
IGG1 LPAPIEKTIS KAKGQPREPQ VYTLPPSRDE LTKNQVSLTC LVKGFYPSDI AVEWESNGQP ENNYKTTPPV 397
IGG2 LPAPIEKTIS KTKGQPREPQ VYTLPPSREE MTKNQVSLTC LVKGFYPSDI AVEWESNGQP ENNYKTTPPM
IGG4 LPSSIEKTIS KAKGQPREPQ VYTLPPSQEE MTKNQVSLTC LVKGFYPSDI AVEWESNGQP ENNYKTTPPV
       E333A/K334A
                                  M428L
                                  |    H433K/N434Y
IGG1 LDSDGSFFLY SKLTVDKSRW QQGNVFSCSV MHEALHNHYT QKSLSLSPGK* 447
IGG2 LDSDGSFFLY SKLTVDKSRW QQGNVFSCSV MHEALHNHYT QKSLSLSPGK*
IGG4 LDSDGSFFLY SRLTVDKSRW QEGNVFSCSV MHEALHNHYT QKSLSLSLGK*
                                           N434A
```

Fig. 15

SEQUENCE LISTING

```
Sequence total quantity: 10
SEQ ID NO: 1            moltype = AA  length = 330
FEATURE                 Location/Qualifiers
source                  1..330
                        mol_type = protein
                        organism = Homo sapiens
SEQUENCE: 1
ASTKGPSVFP LAPSSKSTSG GTAALGCLVK DYFPBPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWINGK EYKCRVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEATHNHYT QKSLSLSPGK                                   330

SEQ ID NO: 2            moltype = AA  length = 326
FEATURE                 Location/Qualifiers
source                  1..326
                        mol_type = protein
                        organism = Homo sapiens
SEQUENCE: 2
ASTKGPSVFP LAPCSRSTSE STAALGCLVK DYFPBPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REBQFNSTFR  180
VVSVLTVLHQ DWLNGKEYKC KVSNKGLPAP IEKTISKTKG OPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA THNHYTQKSL SLSPGK                                       326

SEQ ID NO: 3            moltype = AA  length = 327
FEATURE                 Location/Qualifiers
source                  1..327
                        mol_type = protein
                        organism = Homo sapiens
SEQUENCE: 3
ASTKGPSVFP LAPCSRSTSE STAALGCLVK DYFPBPVTVS WNSGALTSGV HTFPAVLQSS  60
GLYSLSSVVT VPSSSLGTKT YTCNVDHKPS NTKVDKRVES KTGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWINGKEYK CKVSNKGLPS SIEKTISKAK GOPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ATHNHYTQKS LSLSLGK                                      327

SEQ ID NO: 4            moltype = AA  length = 764
FEATURE                 Location/Qualifiers
source                  1..764
                        mol_type = protein
                        organism = Homo sapiens
SEQUENCE: 4
MRPADLLQLV LLLDLPRDLG GMGCSSPPCE CHQEEDFRVT CKDIQRIPSL PPSTQTLKLI  60
ETHLRTIPSH AFSNLPNISR IYVSIDLTLQ QLESHSFYNL SKVTHIEIRN TRNLTYIDPD  120
```

-continued

```
ALKELPLLKF LGIFNTGLKM FPDLTKVYST DIFFILEITD NPYMTSIPVN AFQGLCNETL  180
TLKLYNNGFT SVQGYAFNGT KLDAVYLNKN KYLTVIDKDA FGGVYSGPSL LDVSQTSVTA  240
LPSKGLEHLK ELIARNTWTL KKLPLSLSFL HLTRADLSYP SHCCAFKNQK KIRGILESLM  300
CNESSMQSLR QRKSVNALNS PLHQEYEENL GDSIVGYKEK SKFQDTHNNA HYYVFFEEQE  360
DEIIGFGQEL KNPQEETLQA FDSHYDYTIC GDSEDMVCTP KSDEFNPCED IMGYKFLRIV  420
VWFVSLLALL GNVFVLLILL TSHYKLNVPR FLMCNLAFAD FCMGMYLLLI ASVDLYTHSE  480
YYNHAIDWQT GPGCNTAGFF TVFASELSVY TLTVITLERW YAITFAMRLD RKIRLRHACA  540
IMVGGWVCCF LLALLPLVGI SSYAKVSICL PMDTETPLAL AYIVFVLTLN IVAFVIVCCC  600
YVKIYITVRN PQYNPGDKDT KIAKRMAVLI FTDFICMAPI SFYALSAILN KPLITVSNSK  660
ILLVLFYPLN SCANPFLYAI FTKAFQRDVF ILLSKFGICK RQAQAYRGQR VPPKNSTDIQ  720
VQKVTHDMRQ GLHNMEDVYE LIENSHLTPK KQGQISEEYM QTVL                  764

SEQ ID NO: 5           moltype = AA  length = 260
FEATURE                Location/Qualifiers
source                 1..260
                       mol_type = protein
                       organism = Homo sapiens
SEQUENCE: 5
MRPADLLQLV LLLDLPRDLG GMGCSSPPCE CHQEEDFRVT CKDIQRIPSL PPSTQTLKLI  60
ETHLRTIPSH AFSNLPNISR IYVSIDLTLQ QLESHSFYNL SKVTHIEIRN TRNLTYIDPD  120
ALKELPLLKF LGIFNTGLKM FPDLTKVYST DIFFILEITD NPYMTSIPVN AFQGLCNETL  180
TLKLYNNGFT SVQGYAFNGT KLDAVYLNKN KYLTVIDKDA FGGVYSGPSL LDVSQTSVTA  240
LPSKGLEHLK ELIARNTWTL                                             260

SEQ ID NO: 6           moltype = AA  length = 238
FEATURE                Location/Qualifiers
source                 1..238
                       mol_type = protein
                       organism = Homo sapiens
SEQUENCE: 6
GCSSPPCECH QEEDFRVTCK DIQRIPSLPP STQTLKLIET HLRTIPSHAF SNLPNISRIY  60
VSIDLTLQQL ESHSFYNLSK VTHIEIRNTR NLTYIDPDAL KELPLLKFLG IFNTGLKMFP  120
DLTKVYSTDI FFILEITDNP YMTSIPVNAF QGLCNETLTL KLYNNGFTSV QGYAFNGTKL  180
DAVYLNKNKY LTVIDKDAFG GVYSGPSLLD VSQTSVTALP SKGLEHLKEL IARNTWTL    238

SEQ ID NO: 7           moltype = AA  length = 239
FEATURE                Location/Qualifiers
source                 1..239
                       mol_type = protein
                       organism = synthetic construct
SEQUENCE: 7
MGCSSPPCEC HQEEDFRVTC KDIQRIPSLP PSTQTLKLIE TCLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTE IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTL   239

SEQ ID NO: 8           moltype = AA  length = 232
FEATURE                Location/Qualifiers
source                 1..232
                       mol_type = protein
                       organism = synthetic construct
SEQUENCE: 8
EPKSADKTHT CPPCPAPEAA GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALAAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 9           moltype = AA  length = 5
FEATURE                Location/Qualifiers
source                 1..5
                       mol_type = protein
                       organism = synthetic construct
SEQUENCE: 9
GGGGS                                                             5

SEQ ID NO: 10          moltype = AA  length = 13
FEATURE                Location/Qualifiers
source                 1..13
                       mol_type = protein
                       organism = synthetic construct
DISULFID               2
                       note = Cys2 and Cys12 form a disulfide linkage that make
                        the peptide have a cyclic structure.
DISULFID               12
                       note = Cys2 and Cys12 form a disulfide linkage that make
                        the peptide have a cyclic structure.
MOD_RES                1
                       note = Triazole-x3(alpha-N-acetylgalactosamine -
                        Polyethylene glycol) (GN3) moiety
```

-continued

```
SEQUENCE: 10
DCAWHLGELV WCT                                                         13
```

BIFUNCTIONAL DEGRADERS FOR THE TREATMENT OF GRAVES' DISEASE

CROSS-REFERENCE TO RELATED APPLICATIONS

This patent matter claims the benefit of priority under 35 U.S.C. § 119(e) of U.S. provisional patent application No. 63/677,437, filed, Jul. 31, 2024, the contents of which are incorporated by reference in their entirety.

SEQUENCE LISTING

The instant application contains a Sequence Listing which has been submitted electronically in XML format and is hereby incorporated by reference in its entirety. Said XML copy, created on May 22, 2025, is named 30133-US-NP_SL.xml and is 13,604 bytes in size.

FIELD OF THE INVENTION

The invention generally relates to medicinal preparations characterized by the non-active ingredients used, e.g., carriers or inert additives, targeting or modifying agents chemically bound to the active ingredient, the non-active ingredient being chemically bound to the active ingredient, e.g., polymer-drug conjugates the non-active ingredient being a modifying agent the modifying agent being an antibody, an immunoglobulin or a fragment thereof, e.g., an Fc-fragment the modifying agent being an antibody or an immunoglobulin bearing at least one antigen-binding site the antibody targeting a receptor, a cell surface antigen or a cell surface determinant, and particularly to bifunctional molecules which contain a circulating protein-binding moiety linked through a linker group to a cellular receptor-binding moiety for the treatment of Graves' disease, Thyroid Eye Disease, Hashimoto thyroiditis, and other thyroid stimulating hormone (TSH) receptor (TSHR)-related diseases.

BACKGROUND OF THE INVENTION

Graves' disease (GD) is an autoimmune condition and the most common cause of hyperthyroidism. In Graves' disease, the feedback control mechanism of thyroid function is no longer effective in the presence of thyroid stimulating autoantibodies. Graves' disease patients present with clinical symptoms of a hyperactive thyroid characterized by excess of thyroid hormones in serum and their metabolic consequences. Extrathyroidal manifestations include Graves orbitopathy (GO) or Thyroid Eye Disease (TED).

Thyroid stimulating hormone (TSH) receptor autoantibodies (TRAbs) are responsible for the pathology of Graves' disease. There are two main types of TSH receptor autoantibodies, the stimulating type and the blocking type. See Rees Smith et al., Thyroid, 17, 923-938 (2007) and Rees Smith et al., Hormone and Metabolic Research, 41, 448-455 (2009). Thyroid-stimulating autoantibodies bind to the TSH receptor and mimic the actions of TSH, thereby stimulating the thyroid to produce high levels of hormones triiodothyronine (T3) and thyroxine (T4). Thyroid-stimulating autoantibodies have TSHR agonist activity. Rees Smith et al., Thyroid, 17, 923-938 (2007). The detection of high anti-TSHR levels establishes a Graves' disease diagnosis. See Davies et al., Nature Reviews Disease Primers, 6 (1), 52 (Jul. 2, 2020). Stimulating anti-TSHR antibodies are correlated with clinical activity score. See Lytton et al. J Clin Endocrinol Metab. (2010).

The standard of care for treatment for Graves' disease and other TSH receptor-related diseases centers on antithyroid drugs, radioiodine therapy and surgery, with no significant changes in treatment for many years. There remains a need in the biomedical art for new medicines capable of treating, preventing, or slowing down the progression of Graves' disease and other TSH receptor-related diseases.

SUMMARY OF THE INVENTION

The invention provides anti-TSHR selective compositions of matter for the targeted degradation of anti-TSHR antibodies.

In one embodiment, the invention provides a composition of matter (an agent, a TRAP) comprising:

- a binding moiety that can bind to anti-TSH receptor autoantibody,
- a cellular receptor-binding moiety that can bind to hepatocytes or other degrading cells through asialoglycoprotein receptors (ASGPR) of hepatocytes or other cell receptors on the surface of hepatocytes or other degrading cells in a patient or subject, and
- a linker moiety connecting the anti-TSH receptor autoantibody-binding moiety and the cellular receptor-binding moiety.

In some embodiments, the invention provides a composition of matter (an agent) having a structure of:

$R^{CN}$-(Xaa)y—$R^{CC}$,

[AGN101]

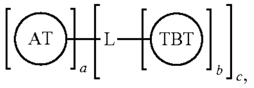

[AGN102]

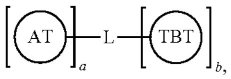

or a salt thereof.

In some embodiments, the composition of matter has a structure:

Formula (I)

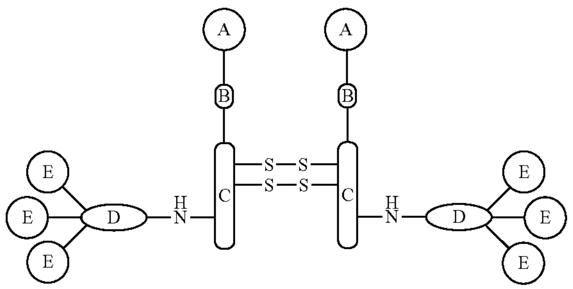

wherein, each 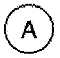 is a moiety having SEQ ID NO: 7 or a sequence having 95% sequence identity therewith;

each 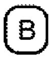 is a means for connecting 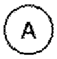 and

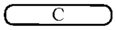;

each

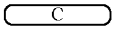

is a peptide moiety having SEQ ID NO: 8, wherein the moieties

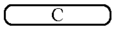

are linked together via two disulfide bridges

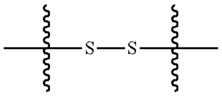 [SMILES: *SS*]

as shown in Formula (II), wherein one disulfide bridge links cysteine residues located in position 11 of SEQ ID NO: 8 of each moiety

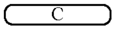, and wherein the other disulfide bridge links cysteine residues located in position 14 of SEQ ID NO: 8 of each moiety

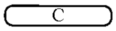;

each

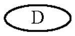

is a means for connecting

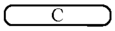

and 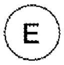, wherein each

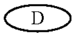

is connected to

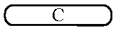

via a side chain amino group of a lysine residue of

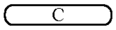

to form

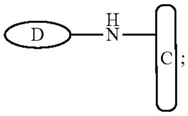;

and each 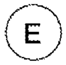 is an asialoglycoprotein receptor ("ASGPR") binding moiety comprising an N-acetyl-D-galactosamine ("GalNAc") group having Formula (II):

Formula (II)

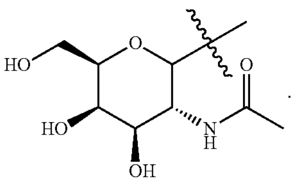.

In a particular embodiment, the composition of matter is AGN301.

In some embodiments, the binding moiety that can bind to anti-TSH receptor autoantibody is selected from the Markush group consisting of any suitable form of TSH receptor, a mutant TSH receptor, or fragments thereof, e.g., TSHR260™, that includes one or more epitopes of a TSH receptor. In some embodiments, the binding moiety may be a polypeptide comprising one or more epitopes of a TSH receptor, as described by International Patent Publication WO 2015/189543 (RSR Ltd.). Many TSH receptors are commercially available. In some commercially available TSH receptors, the protein is rendered stable by the introduction of six mutations.

In some embodiments, the binding moiety further comprises a VHH moiety conjugated to the linker moiety, wherein one or two TSH receptors, mutant TSH receptors, or fragments thereof, or one or two polypeptides comprising one or more epitopes of a TSH receptor are conjugated to one or each of the protein chains of the VHH moiety.

In a particular embodiment, the binding moiety is ABT301 (SEQ ID NO: 7).

In another embodiment, the cellular receptor-binding moiety comprises an ASGPR binding group according to the chemical structure:

[TBT101]

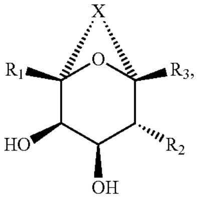

or

[TBT102]

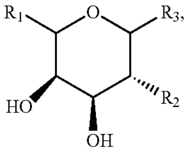

wherein the cellular receptor-binding moiety has additional elements described in this specification. Groups $R^1$, $R^2$, $R^3$, and X may be the same as described in International Patent Publication WO 2019/199634 and International Patent Publication WO 2019/199621.

In a specific embodiment, the cellular receptor-binding moiety is TBT301 or a conjugation reaction derivative thereof. See FIG. 4.

In another embodiment, the invention provides a method of making the composition of matter (agent).

In a specific embodiment, the method of making the composition of matter comprises the step of conjugating ABT301 (leucine rich domain (LRD)-Fc) and TBT301 to make the AGN301 composition of matter.

In another embodiment, the invention provides a method of removing anti-TSHR antibodies from a subject by administering the composition of matter (agent) to the subject. In yet another embodiment, the composition of matter is administered so that in vivo activity is as low as 0.1 mpk, based upon results shown in this specification.

In another embodiment, the invention provides a method of treating a disease state or condition associated with the upregulation of anti-TSH receptor autoantibody, such as Graves' disease, Graves orbitopathy (GO), or Thyroid Eye Disease (TED), in a patient by administering an effective amount of the agent to the patient.

In another embodiment, the invention provides a method of treating Graves' disease, Graves orbitopathy (GO), or Thyroid Eye Disease (TED), in a patient by administering an effective amount of the composition of matter (agent) to the patient.

In yet another embodiment, the invention provides a method of treating Graves' disease in a patient by administering an effective amount of a combination of the composition of matter (agent) and Compound 1, which is an IgG degrader to the patient. In still another embodiment, the composition of matter (agent) and Compound 1 are administered simultaneously. In still another embodiment, the composition of matter (agent) and Compound 1 are administered sequentially.

In another embodiment, the invention provides a method of treating Hashimoto thyroiditis in a patient or subject in need by administering an effective amount of the agent to the patient or subject.

In another embodiment, the invention provides a pharmaceutical composition including the agent and at least one pharmaceutically acceptable excipient.

In another embodiment, the invention provides a composition including the agent, and at least one additional agent comprising a moiety capable of binding to that forms the antibody-binding moiety of the first compound.

Several objects, features, aspects, and advantages of the invention will become more apparent from the following detailed description of embodiments of the invention, along with the accompanying drawings.

BRIEF DESCRIPTION OF THE DRAWINGS

For illustration, some embodiments of the invention are shown in the drawings described below. Like numerals in the drawings indicate like elements throughout. The invention is not limited to the precise arrangements, dimensions, and instruments shown.

FIG. 15 is a sequence comparison of the constant heavy chains of human IgG1, IgG2, and IgG4, which can be therapeutic antibodies. Sequence differences in IgG2 and IgG4 from IgG1 are noted. The hinge and lower hinge regions, with the N-glycosylation site, N297, are noted. Numbering is according to the EU numbering scheme. Sequences important for FcgR binding, C1q, and FcRn are noted by shading. Some increased ADCC mutants are shown above or below the sequences, as noted: Xencor's S239D, A330L, I332E; Genentech's S298A, E333A, K334A; and Eli Lilly/AME's P247I, A339D/Q. Examples of FcRn-binding mutants for prolongation of half-life are also shown, as noted: MedImmune's YTE mutant (M252Y, S254T, T256E), PDL's T250Q, M428L mutant, Sally Ward's H433K mutant, N434Y mutant, and Genentech's N434A mutant are shown.

DETAILED DESCRIPTION OF THE INVENTION

Figure 1:
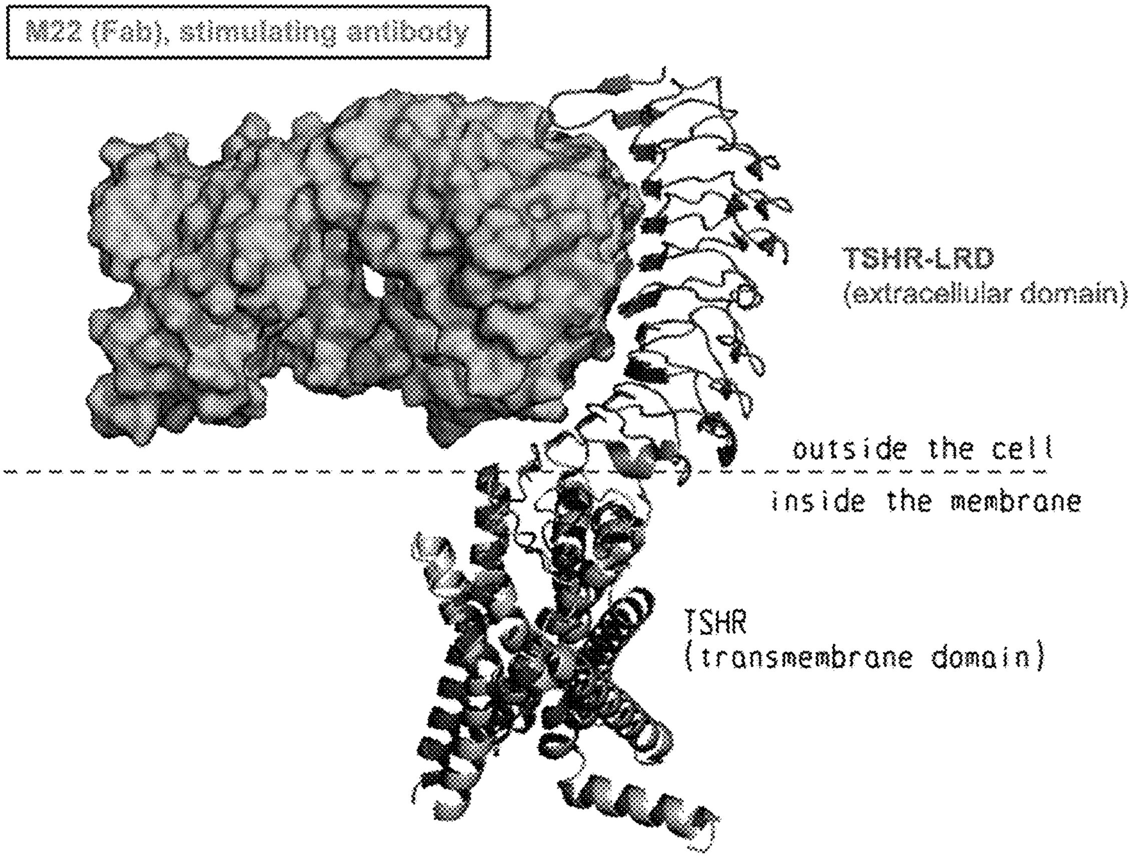
FIG. 1 illustrates the leucine-rich domain (LRD, residues 22 to 260) domain of the TSHR that binds agonistic autoantibodies according to an embodiment of the present invention (PDB: 7T9N; Faust et al, Nature, 2022)
Figure 2:
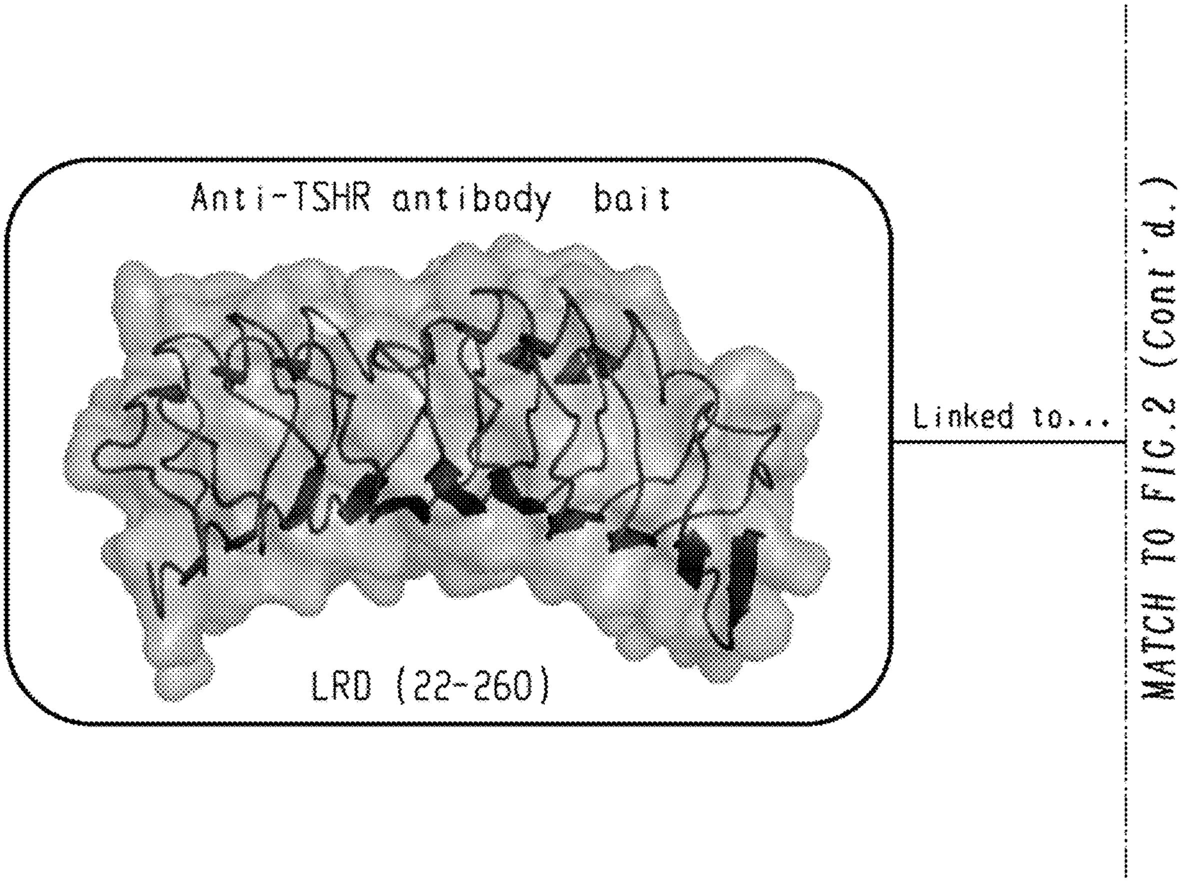
FIG. 2 illustrates a concept of incorporating the LRD domain of the TSHR into a degrader molecule according to an embodiment of the present invention.
Figure 2:
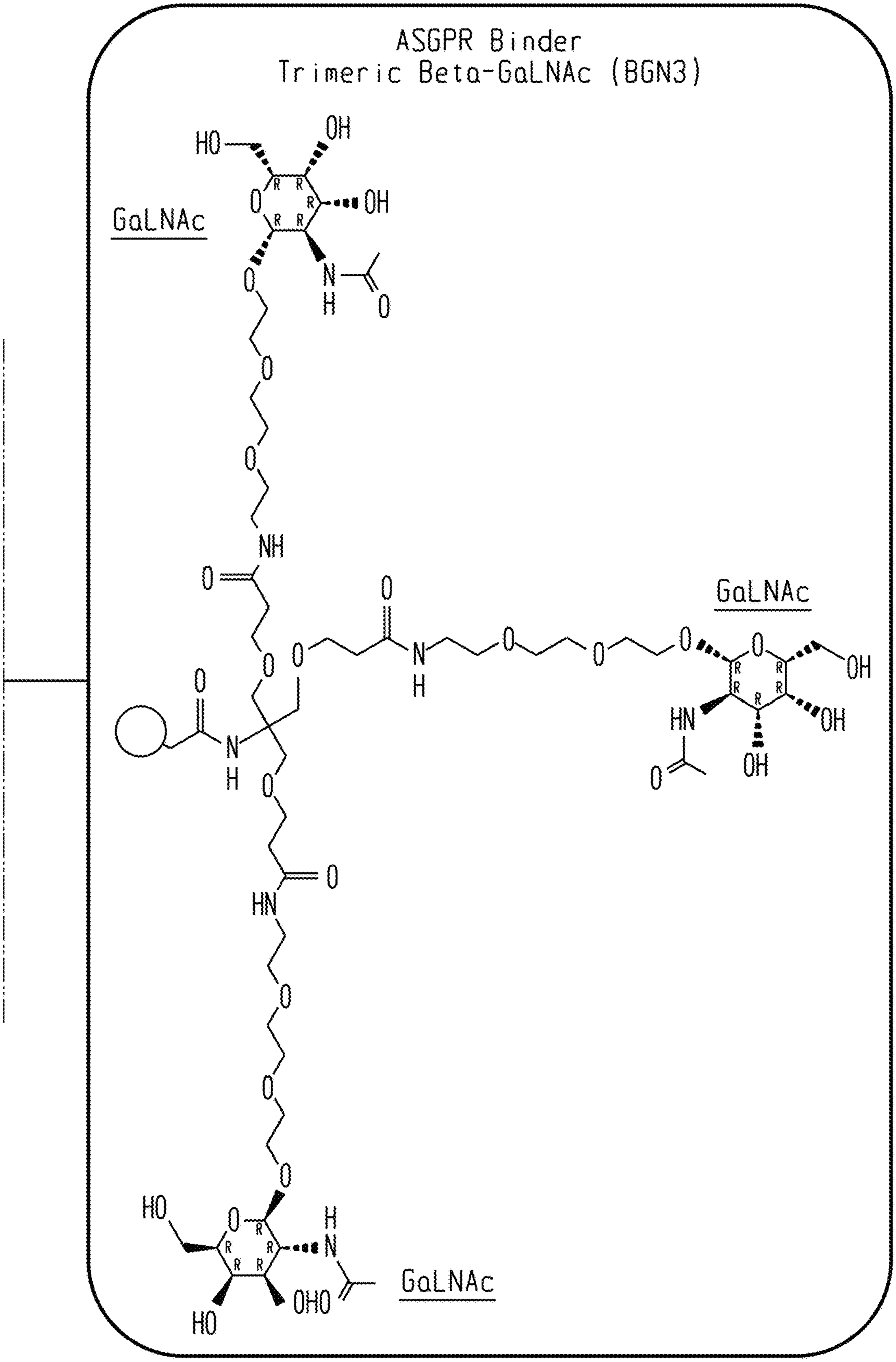
Figure 3:
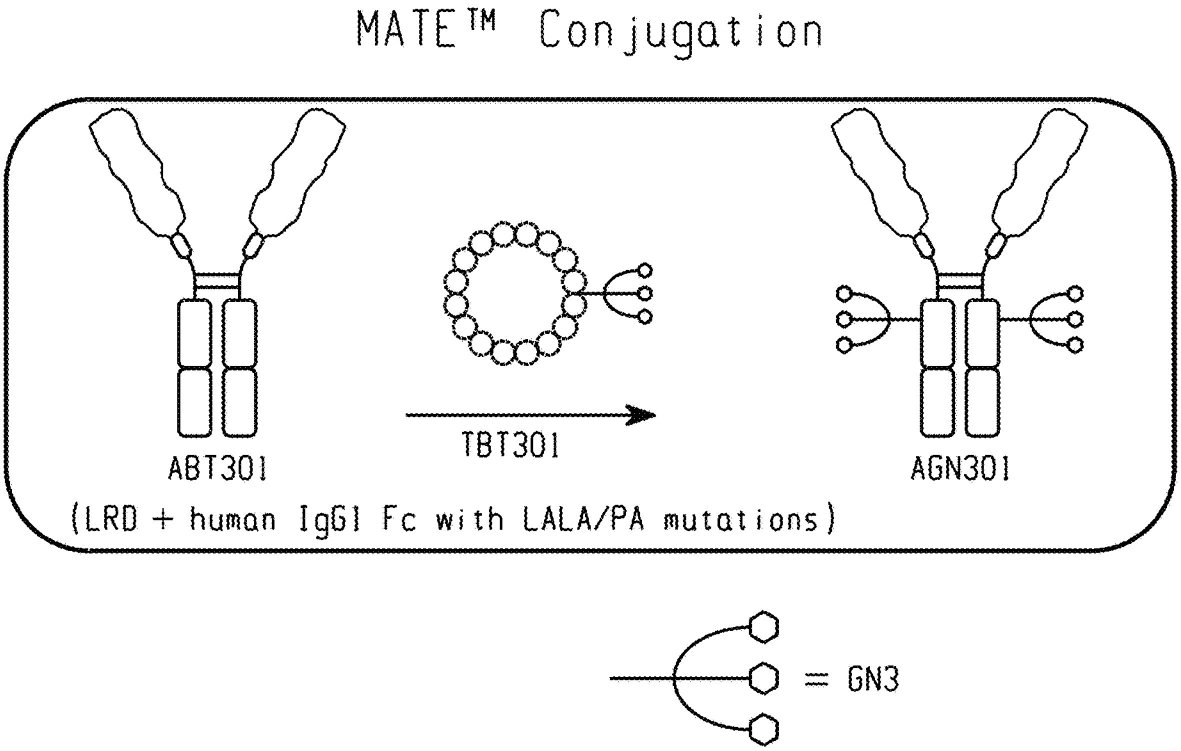
FIG. 3 illustrates site-specific conjugation of the degrader portion to the Fc domain of the protein using MATE™ technology according to an embodiment of the present invention.
Figure 4:
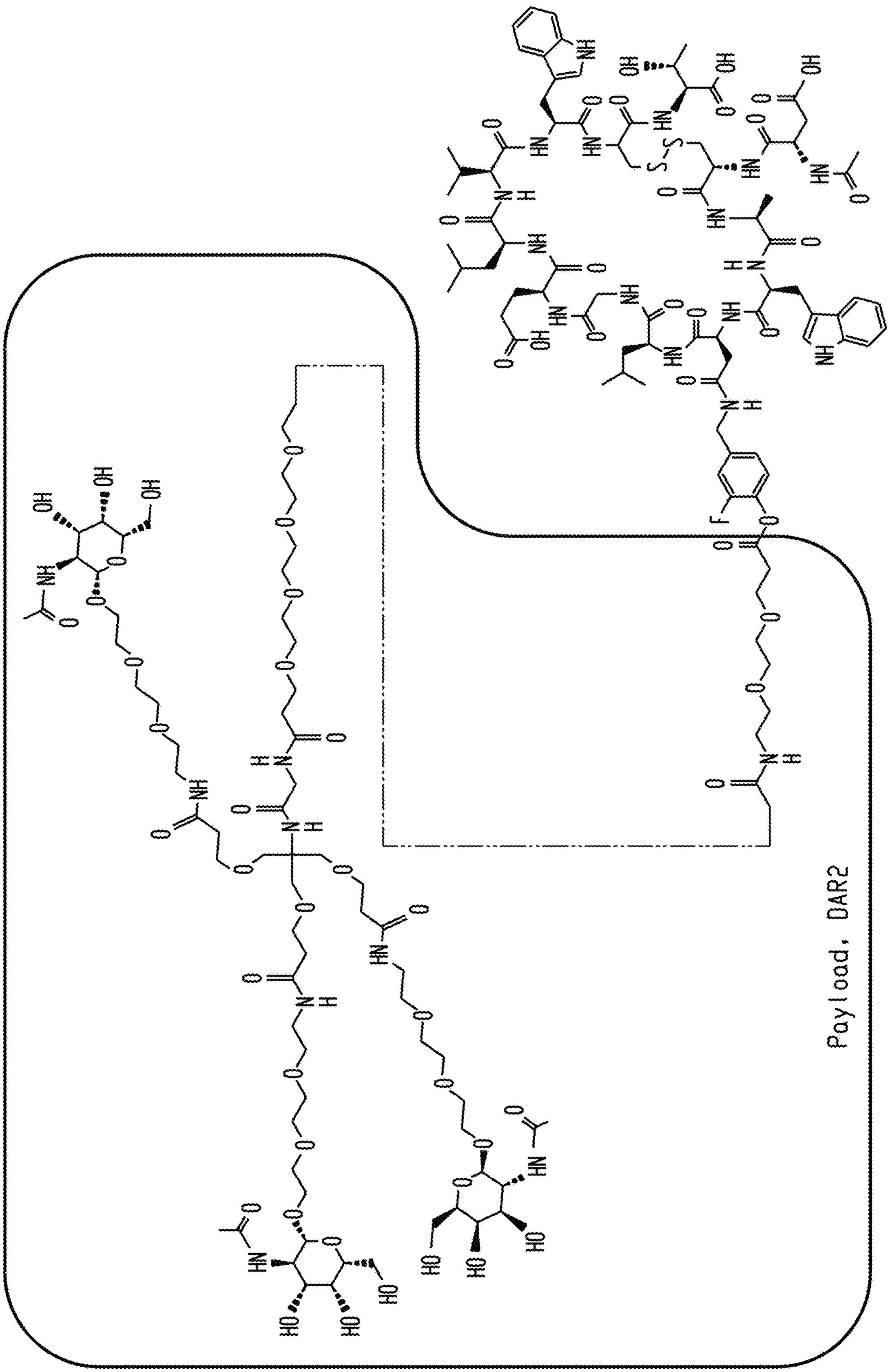
FIG. 4 shows the structure of reagent TBT301 according to an embodiment of the present invention.

The following detailed description is provided to aid persons having ordinary skill in the biomedical art. Exemplary embodiments are described, but these embodiments are only exemplary. This disclosure is not limited thereto but is defined by the scope of the appended claims. Persons having ordinary skill in the biomedical art may make modifications and variations in the embodiments described in this specification without departing from the spirit or scope of this disclosure.

INDUSTRIAL APPLICABILITY

The invention provides a medically useful composition of matter (agent) for treating or slowing down the progression of Graves' disease, Graves orbitopathy (GO), Thyroid Eye Disease (TED), or other diseases associated with autoantibodies that bind the TSHR receptor. Autoimmune thyroid disease is one of the most common autoimmune conditions. See Pokhrel & Bhusal, Graves' Disease. In: StatPearls [Internet] (Treasure Island (FL), StatPearls Publishing, January 2024). Early diagnosis and management of Graves' disease can also prevent severe cardiac complications such as atrial flutter, atrial fibrillation, and high-output cardiac failure.

In other embodiments, the invention provides a medically useful composition of matter (agent) for treating or slowing down the progression of Hashimoto thyroiditis. To determine the antigen to which the Hashimoto makes autoantibodies, a physician can order one or more blood tests to check for hypothyroidism and its causes. Examples include tests for the thyroid hormones T4 (thyroxine) and T3 (triiodothyronine), thyroid-stimulating hormone (TSH), and thyroid peroxidase antibodies (TPO). Persons having ordinary skill in the biomedical art can make or physicians can select a composition of matter (agent) where the autoantibody binding moiety is, as appropriate, selected from a member of the Markush group consisting of T4 (thyroxine), T3 (triiodothyronine), thyroid-stimulating hormone (TSH) or an antigenic fragment thereof, thyroid peroxidase (TPO) or an antigenic fragment thereof; and thyroglobulin or an antigenic fragment thereof.

Definitions

For convenience, the meaning of some terms and phrases used in the specification, examples, and appended claims are listed below. Unless stated otherwise or implicit from context, these terms and phrases shall have the meanings below. These definitions aid in describing embodiments but are not intended to limit the claimed invention.

As used in this application, except as otherwise expressly provided in this specification, each of these terms shall have the meaning set forth below. Additional definitions are set forth throughout the application. Where a term is not specifically defined in this specification, that term is given a biomedical art-recognized meaning, applying that term in context to its use in describing the invention.

The articles "a" and "an" have the plain meaning of one or more than one, i.e., at least one, of the grammatical object of the article unless the context indicates otherwise. For example, "an element" means one element or more than one element.

The term "active Ingredient" has the United States Food & Drug Administration-provided meaning of any component that provides pharmacological activity or other direct effect in the diagnosis, cure, mitigation, treatment, or prevention of disease or to affect the structure or any function of a human body or an animal body.

The term "agent" has the biomedical art-recognized meaning of a composition of matter useful for performing a function. Several biomedically useful functions are described in this specification.

The term "alleviate" has the biomedical art-recognized meaning of a process by which the severity of a sign or symptom of a disorder is decreased. A sign or symptom can be alleviated without being eliminated. The administration of compositions or pharmaceutical compositions of the invention may or can lead to the elimination of a sign or symptom. However, elimination is not required. Effective dosages should be expected to decrease the severity of a sign or symptom.

The term "asialoglycoprotein receptor (ASGPR) binding group" has the biomedical art-recognized meaning of a binding group that binds to a hepatocyte asialoglycoprotein receptor. The ASGPR binding group selectively binds to hepatocyte asialoglycoprotein receptors on the surface of hepatocytes. In several embodiments of this specification, an ASGPR binding group is a component of a bifunctional agent as a cellular receptor-binding moiety covalently bound to the antibody-binding moiety through a linker group or directly. Bifunctional agents complexed with a circulating protein, e.g., bind to hepatocytes, through this ASGPR moiety. After the bifunctional agent complexed with a circulating protein is bound to a hepatocyte or other cell, the circulating protein is taken into the hepatocyte or other cell via an endocytosis mechanism, wherein the circulating protein is degraded through lysosomal degradation.

The term "asialoglycoprotein receptor (ASGPR) has the biomedical art-recognized meaning of lectins, which bind asialoglycoprotein and glycoproteins from which a sialic acid has been removed to expose galactose residues. These cellular receptors are located on mammalian hepatocytes and other cells, such as glandular cells of the gallbladder and the stomach.

The term "at least one of," when preceding a list of elements, modifies the entire list of elements and does not modify the individual elements of the list.

The term "AT" or "ABT" means a binding moiety that binds to or is bound by an anti-TSH receptor autoantibody.

The term "autoantibody" has the biomedical art-recognized meaning. TSH receptor autoantibodies (TRAbs) bind to the TSH receptor. TSH receptor autoantibodies with stimulating activity are responsible for hyperthyroidism in Graves' disease. TSH receptor autoantibodies with blocking activity may cause hypothyroidism. Rees Smith, Mclachlan, & Furmaniak, Endocrine Reviews, 9, 106-121 (1988); Rapoport et al., Endocrine Reviews. 19, 673-716 (1988); Furmaniak et al., Clinical Endocrinology, 96, 878-887 (2022). In a first example of an autoantibody, K1-70™ IgG1 lambda is a blocking type human monoclonal autoantibody to the TSH receptor obtained from the peripheral blood lymphocytes of a patient with hypothyroidism. See Intl. Pat. Publ. WO 2010/073012; Evans et al, Clinical Endocrinology 73:404-412 (2010). K1-70™ is a powerful inhibitor of TSH action. Núñez Miguel et al., Structure of full-length TSH receptor in complex with antibody K1-70™. Journal of Molecular Endocrinology, 70, e220120 (2022). K1-70™ IgG can be purified from heterohybridoma culture supernatants. Fab can be manufactured using mercuripapain. Sanders et al., Journal of Molecular Endocrinology, 46, 81-99 (2011). The K1-70™ Fab structure consists of K1-70™ heavy chain (HC) residues Gln1 to Ser229 and light chain (LC) residues Ser2 to Ala212 and is the structure of a typical Fab fragment. K1-70™ IgG1 lambda is commercially available from RSR limited (Order Code K170/FR/1.0). In a second example of an autoantibody, human monoclonal TSH receptor autoantibody M22™ IgG1 lambda is a powerful stimulator of the TSH receptor. See European Pat. No. EP1565493B1. M22™ is commercially available from RSR Limited (Order Code M22/FR/1.0). In a third example of an autoantibody, mouse monoclonal TSH receptor antibody 14C4 binds to a conformational epitope within amino acids 22-260 of the TSH receptor distinct from the K1-70™ binding site. A fourth example is K1-18™ IgG1 kappa, which is commercially available from RSR limited (Order Code K118/FR/1.0).

The term "autoimmunity" has the biomedical art-recognized meaning of the system of immune responses of an organism against its own healthy cells, tissues and other normal body constituents. Autoimmunity means the presence of antibodies or T cells that react with self-protein. Self-reactivity can lead to tissue damage. A disease resulting from this type of immune response is an "autoimmune disease".

The term "binding moiety" has the biomedical art-recognized meaning of a moiety on a binding protein, e.g., an antibody, an antibody variant, or an antigen-binding fragment thereof, that binds to the anti-TSH receptor autoantibody.

The term "cellular receptor-binding moiety" has the biomedical art-recognized meaning. In several embodiments of this specification, the cellular receptor-binding moiety is an asialoglycoprotein receptor (ASGPR) binding group.

The term "cellular receptor" has the biomedical art-recognized meaning of a protein on the surface of a cell that binds to a compound, e.g., a ligand, e.g., a protein, in solution or on another cell. Generally, ligand-receptor binding induces one or more biological responses. In this specification, an asialoglycoprotein receptor (ASGPR) is a cellular receptor on the surface of hepatocytes or other cells that binds to an asialoglycoprotein or a derivative thereof.

The term "chimerized" has a biomedical art-recognized meaning. Chimeric antibodies are made by fusing variable domains from one species, such as a mouse, with constant domains from another species, such as a human being. Through these biotechnical manipulations, chimeric antibodies retain the foreign antibody's antigen specificity and affinity.

The term "drug to antibody ratio" (DAR) has biomedical art-recognized meaning when used in making antibody conjugates.

The term "epitope of a TSH receptor" has the biomedical art-recognized meaning and includes epitopes that are recognized by anti-TSH receptor antibodies. A first epitope: K1-70™ binds to the TSH receptor well clear of the lipid bilayer. K1-70™ Fab binding is principally to the concave surface of the TSH receptor leucine rich domain (LRD) which has no glycans attached. K1-70™ Fab HC and LC bind to the N-terminal leucine-rich repeats (LRR) of the TSH receptor from amino acid Glu35 in the TSH receptor N-cap to Lys183 in the 7th LRR. There is a mixture of an extensive hydrogen bonding and salt bridge network (twenty hydrogen bonds and salt bridges), five ion pairs, thirteen polar interactions, and thirteen hydrophobic/aromatic contacts. Differences in some of the interactions seen in the cryo-EM structure of the full-length TSH receptor bound to K1-70™ Fab compared to the crystal structure of the TSH receptor leucine rich domain in complex with K1-70™ Fab are most likely due to side chain flexibility in the interacting amino acids. There are no interactions between the K1-70™ Fab and either the HR or the TMD. A second epitope: M22™ binds to the TSH receptor at a region where it would clash with the bilayer unless the TSH receptor HR rotates upwards as part of the M22™ binding process. M22™ interacts with TSH receptor amino acids more C-terminal than those that interact with K1-70™. Sanders et al., Journal of Molecular Endocrinology, 46, 81-99 (2011). This 'push' process may explain the observations of Chazenbalk et al., Journal of Clinical Investigation 110 209-217 (2002), who noted that thyroid-stimulating antibodies, but not thyroid-blocking antibodies were partially sterically hindered when binding to the full-length TSH receptor compared to the TSH receptor ECD alone. A partial obstruction of the thyroid-stimulating autoantibody binding site may lead to a torsion effect on the TSH receptor ECD, on antibody binding, which may explain how thyroid-stimulating autoantibodies were able to activate the TSH receptor. Núñez Miguel et al., Journal of Molecular Endocrinology, 70, e220120 (2022).

The term "Graves' disease," also known as toxic diffuse goiter or Basedow's disease, has the biomedical art-recognized meaning of an autoimmune disease characterized by the presence of anti-TSHR auto antibodies that lead to a generalized overactivity of the thyroid gland (hyperthyroidism). Classic symptoms of Graves' disease include exophthalmos, eyelid retraction, insomnia, muscle weakness, tremor, oligomenorrhea, dyspnea, arrhythmia, and fatigue. Persons having ordinary skill in the biomedical art diagnose Graves' disease using methods such as blood tests assaying body levels of anti-TSHR antibodies, thyroid-stimulating hormone (TSH), thyroid hormones, radioactive iodine uptake assays.

The term "Graves' ophthalmopathy" (GO; or Thyroid Eye Disease, TED), has biomedical art-recognized meaning of an autoimmune disorder affecting the tissues around the eyes.

The term "Hashimoto thyroiditis" has the biomedical art-related meaning of an autoimmune thyroiditis when the autoantibodies that attack the thyroid cells. Many Hashimoto thyroiditis patients have hypothyroidism. See Choe, Durgannavar, & Chung, Materials (Basel), 9 (12), 994 (Dec. 8, 2016).

The term "hepatocyte" has the biomedical art-recognized meaning of a cell of the main parenchymal tissue of the liver. Hepatocytes make up 55-65% of the liver's mass.

The term "humanized" has the biomedical art-recognized meaning that a protein, e.g., an antibody, is genetically engineered to closely resemble the polypeptide structure of the human homologue. A variable domain of an antibody of rodent origin can be fused to a constant domain of human origin, thus retaining the specificity of the rodent antibody. The human origin domain need not originate directly from a human when it is first synthesized in a human. Human domains can be generated in rodents whose genome incorporates human immunoglobulin genes. The antibody can be partially or completely humanized. In one approach, four general steps are used to humanize a monoclonal antibody. These steps are (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

The term "$IC_{50}$" has the biomedical art-recognized meaning of an amount, concentration, or dosage of a particular test compound that achieves a 50% inhibition of a maximal response in an assay that measures such response.

The term "IgG" antibody has the biomedical art-recognized meaning. Each IgG molecule consists of the basic four-chain immunoglobulin structure—two γ (gamma) heavy chains and two identical light chains (either kappa or lambda)—and carries two identical antigen-binding sites. There are four subclasses of IgG, each with minor differences in its H chains but with distinct biological properties.

The term "IgG1" antibody has the biomedical art-recognized meaning of an IgG antibody where the Ig gamma-1 chain C region is a protein encoded by the IGHG1 gene in humans.

The term "IgG2" antibody has the biomedical art-recognized meaning of an IgG antibody where the Ig gamma-2 chain C region is a protein encoded by the IGHG2 gene in humans.

The term "IgG4" antibody has the biomedical art-recognized meaning of an IgG antibody where the Ig gamma-4 chain C region is a protein encoded by the IGHG4 gene in humans. IgG4 has little effector function. IgG4 cannot fix complement.

The term "IVIG" has the biomedical art-recognized meaning of administering intravenous immunoglobulin (IVIG).

The term "$K_D$" has the biomedical art-recognized meaning of the measured equilibrium dissociation constant between a compound or ligand and a protein or binding domain of a protein.

The term "leucine rich domain" (LRD) has biomedical art-recognized meaning of amino acids 22-260 of the extracellular portion of the TSH receptor. The leucine rich domain is described further in this specification.

The term "linker moiety" has the biomedical art-recognized meaning of a moiety of a chemical compound that links one moiety of the chemical compound to another moiety of the same compound.

The term "MODE" has the proprietary meaning of molecular degraders. See International Pat. Publ. WO 2019/199634 (Yale University) and International Pat. Publ. WO 2019/199621 (Yale University).

The term "moiety" has the biomedical meaning of a defined chemical group or entity with a particular structure or activity. A moiety generally refers to a part of a molecule. In some embodiments, a binding moiety maintains one or more desired structural features, properties, functions, or properties, e.g., 3-dimension structure, antigen specificity, antigen-binding capacity, or immunological functions, etc., comparable to its corresponding binding protein, e.g., an antibody. In some embodiments, a moiety is monovalent. In some embodiments, a moiety is bivalent. In other embodiments, a moiety is polyvalent.

The term "monotherapy" is a biomedical art-recognized term for administering a single active or therapeutic compound to a subject or patient in need. Monotherapy usually involves administering a therapeutically effective amount of an active composition.

The term "Multimodal Antibody Therapy Enhancers (MATE or MATES)" has the proprietary meaning. See International Pat. Publ. WO 2021/102052 (Kleo Pharmaceuticals).

The term "on" has the plain meaning. When an element is referred to as being on another element, it can be directly in contact with the other element, or intervening elements may be present therebetween. When an element is referred to as being "directly on" another element, no intervening elements are present.

The term "or" as used in this specification, means "or." The term "or" as used in this specification, includes all combinations of one or more of the associated listed items.

The term "other degrading cells" has the biomedical art-recognized meaning. Asialoglycoprotein receptors (ASGPRs) are found on hepatocytes and the glandular cells of the gallbladder and stomach.

The term "partially humanized" has the biomedical art-recognized meaning that a protein, e.g., an antibody, is genetically engineered to resemble the polypeptide structure of the human homologue more closely. A variable domain of an antibody of rodent origin can be fused to a constant domain of human origin, thus retaining the specificity of the rodent antibody. The domain of human origin need not originate directly from a human in that it is first synthesized in a human. Human domains can be generated in rodents whose genome incorporates human immunoglobulin genes. The antibody can be partially or completely humanized.

The term "pharmaceutically acceptable excipient" has the biomedical art-recognized meaning of an excipient that is useful in preparing a pharmaceutical composition that is generally safe, non-toxic, and neither biologically nor otherwise undesirable, and includes excipient that is acceptable for veterinary use and human pharmaceutical use. A "pharmaceutically acceptable excipient," as used in the specification and claims, includes both one and more than one such excipient. A thorough discussion of pharmaceutically acceptable excipients is available in Remington's Pharmaceutical Sciences 23rd edition (Elsevier, 2020).

The term "pharmaceutically acceptable" has the biomedical art-recognized meaning of those compounds, anions, cations, materials, compositions, carriers, or dosage forms that are, within the scope of sound medical judgment, suitable for contact with the tissues of humans and animals without excessive toxicity, irritation, allergic response, or other problem or complication, commensurate with a reasonable benefit/risk ratio.

The term "protein-binding moiety" has the biomedical art-recognized meaning of a region of a chemical composition, e.g., a polypeptide region of a chemical composition, that specifically binds to a protein, e.g., a specific protein.

The term "rIgG" has the biomedical art-recognized meaning of recombinant human IgG.

The term "ROC" has the biomedical art-recognized meaning of the receiver operating characteristic curve.

The term "TRAP" has the meaning described in this specification of an agent for the targeted removal of aberrant protein. A TRAP™ is a bifunctional degrader.

The term "TBT" has the biomedical art-recognized meaning of a cellular receptor-binding moiety. In some embodiments of this specification, the TBT binds to ASGPR.

The term "thyroglobulin" (Tg) has the biomedical art-recognized meaning. Thyroglobulin autoantibodies (TgAbs) are serological markers of thyroid autoimmunity disease, including Hashimoto's thyroiditis, Graves' disease, a postpartum thyroiditis (PPT), and other autoimmune diseases. Rees Smith et al., Thyroid, 17, 923-938 (2007); Choe, Durgannavar, & Chung, Materials (Basel), 9 (12), 994 (Dec. 8, 2016).

The term "thyroid peroxidase" (TPO) has the biomedical art-recognized meaning. Thyroid peroxidase autoantibodies are serological markers of thyroid autoimmunity disease, including Hashimoto thyroiditis, Graves' disease, a post-partum thyroiditis (PPT), and other autoimmune diseases. Rees Smith et al., Thyroid, 17, 923-938 (2007); Choe, Durgannavar, & Chung, Materials (Basel), 9 (12), 994 (Dec. 8, 2016).

The term "thyroid stimulating hormone (TSH) receptor" (TSHR) has the biomedical art-recognized meaning of a G-protein coupled receptor (GPCR) that regulates thyroid function. TSH receptors are present on the basal membrane of thyroid follicular epithelial cells. Binding of thyroid stimulating hormone (TSH) to the TSH receptor starts the activation of the TSH receptor signaling cascade which involves binding of G-proteins to the TSH receptor followed by stimulation of the cyclic AMP pathway. Sanders et al., Ballière's Clinical Endocrinology and Metabolism, 11, 451-479 (London, Balliere Tindall, 1997); Latif et al., Endocrinology and Metabolism Clinics of North America, 38, 319-341 (2009). The TSH receptor is a major thyroid autoantigen. The TSH receptor can be a human wildtype TSH receptor having the sequence shown in SEQ ID NO: 4 or a functional fragment thereof. In one embodiment, the TSH receptor is a mutated human TSH receptor or a functional fragment thereof. International Pat. Publ. WO 2015/189543 describes mutated human TSH receptor functional fragments comprising residues 22-260 of the TSH receptor as shown in SEQ ID NO 5, wherein the mutant or fragment thereof comprises one, two, three, four, five or six mutations within residues 22-260 selected from P28E, L59F, T62V, H63C, L64Y, R112P, P142I, D143P, D151E, S166T, I167F, P168Y, V169R, N170W, T179C, I253R and R255Y, wherein the mutant TSH receptor fragment thereof has increased thermostability with respect to the equivalent wild type TSH receptor. A thyroid-stimulating hormone receptor protein has a leucine-rich domain (LRD), a hinge region (HR), and a transmembrane domain (TMD). The TSH receptor extracellular domain (ECD) is composed of the leucine rich domain and hinge region. TSH receptor is composed of three domains, the ECD (amino acids 22-409) consisting of the leucine rich domain (amino acids 22-279) and hinge region (hinge region; amino acids 280-409), the TMD and the intracellular C-terminus (amino acids 410-764). The structure of the ECD, formed by the leucine-rich domain and HR, is that of a typical leucine-rich-repeat (LRR) structure with eleven repeats in the leucine-rich domain and one repeat in the HR. Each LRR consists of a parallel β-strand on its concave surface while the N-terminal cap (N-cap) has an additional β-strand antiparallel to the β-strand of the first repeat. The leucine-rich domain and the HR form a continuum structure with the N-cap, with two disulfide bonds, and a C-terminal cap (C-cap) with three disulfide bonds and an alpha helix. One of the two N-terminal disulfide bonds between Cys31 and Cys41 is visible in the structure while the other one between Cys24 and Cys29 is not. All three intra-domain disulfide bonds which form the C-cap are visible in the structure between Cys283 and Cys398, Cys284 and Cys408, and Cys301 and Cys390. The first 21 amino acids of the TSH receptor make up the cleaved signal peptide. See also Choe, Durgannavar, & Chung, Materials (Basel), 9 (12), 994 (Dec. 8, 2016). There is a high sequence consensus of mouse, rat, and cynomolgus monkey TSHR to human TSHR, with at least 86.3% sequence identity with full-length TSHR and 87.9% sequence identity with the leucine-rich domain (amino acids 22-260).

The term "thyroid-stimulating hormone" (TSH, thyrotropin, thyrotropic hormone) has biomedical art-recognized meaning of the pituitary hormone that stimulates the thyroid gland to produce thyroxine (T4), and then triiodothyronine (T3) which affects almost every tissue in the body.

The term "TSHR260" has the biomedical art-recognized meaning of a subdomain of TSH receptor consisting of residues 22-260 and encompassing most of the leucine-rich domain (LRD). Sanders et al., Thyroid, 17, 395-410 (2007). TSHR260 shows similar binding to TR antibodies as the full-length TSH receptor. See Rees Smith et al., Hormone and Metabolic Research, 41, 448-455 (2009) and International Patent Publication WO 2010/073012 (RSR Limited). The structure of TSHR260 remained essentially unchanged upon ligand binding. Miller-Gallacher et al., Journal of Molecular Endocrinology, 62, 117-128 (2019). TSHR260 is commercially available from RSR Limited (TSHR260 STABL™, Order Code STABL/FR/1.0). TSHR260-JMG55™ maintains select properties of the native domain.

The term "universal antibody-binding moiety" has the biomedical art-recognized meaning of a polypeptide region of an antibody-binding protein that binds a class of antibodies rather than a specific set of antibodies.

The term "VHH" has the biomedical art-recognized meaning. VHH has 9 beta-sheets forming a cylindric structure.

The terms "an effective amount" and "a therapeutically effective amount" have the biomedical art-recognized meaning of an amount effective to achieve its intended purpose. The effect can be detected by any assay method known in the art. The precise effective amount for a subject depends on the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In embodiments, the disease or condition to be treated is tendinopathy.

The terms "combination therapy" and "co-therapy" have the biomedical art-recognized meaning of the administration of a composition described in this specification and at least a second agent as part of a specific treatment regimen intended to provide the beneficial effect from the co-action of these therapeutic agents. The beneficial effect of the combination may include but is not limited to pharmacokinetic or pharmacodynamic co-action resulting from the combination of therapeutic agents. These therapeutic agents are typically administered in combination over a defined time, usually minutes, hours, days, or weeks, depending on the combination selected. The term combination therapy" includes the administration of the therapeutic agents described above in combination with other biologically active ingredients and non-drug therapies, e.g., surgery or radiation treatment. Where the combination therapy further comprises a non-drug treatment, the non-drug treatment may be conducted at any suitable time if a beneficial effect from the co-action of the combination of the therapeutic agents is achieved. For example, in appropriate cases, the beneficial effect is still achieved when the non-drug treatment is temporally removed from the administration of the therapeutic agents, perhaps by days or even weeks.

The terms "comprises," "comprising," "includes," and "including" specify the presence of stated features, regions, integers, steps, operations, elements, or components but do not preclude the presence or addition of one or more other features, regions, integers, steps, operations, elements, components, or groups thereof.

The terms "first," "second," "third," etc., have the plain meaning of describing several elements, components, regions, layers, or sections. These terms should not limit these elements, components, regions, layers, or sections. These terms are only used to distinguish one element, component, region, layer, or section from another element, component, region, layer, or section. A first element, component, region, layer, or section could be called a second element, component, region, layer, or section without departing from the teachings of the present embodiments.

The terms "subject" and "patient" have the biomedical art-recognized meanings. The term "patient" includes human and other mammalian subjects receiving prophylactic or therapeutic treatment.

The terms "treating" and "treat" have the biomedical art-recognized meaning of managing and caring for a patient to combat a disease, condition, or disorder. Treating includes administering a composition described in this specification to alleviate the symptoms or complications of a disease, condition, or disorder or to eliminate the disease, condition, or disorder.

Some embodiments are described below by referring to structures and schemes to explain aspects of the description.

Unless otherwise defined, all technical and scientific terms used in this specification have the same meaning as commonly understood by persons having ordinary skill in the biomedical art.

This specification does not concern a process for cloning humans, methods for modifying the germ line genetic identity of humans, uses of human embryos for industrial or commercial purposes, or procedures for modifying the genetic identity of animals likely to cause them suffering with no substantial medical benefit to humans or animals resulting from these processes.

Methods of Removal of Autoantibodies from a Subject or Patient.

How to administer. The best mode of administration depends on where treatment is taking place, whether a hospital or outpatient. In one embodiment, the method of administration is by subcutaneous administration to a patient or subject of 50 mg/ml of the composition of matter (agent).

After the bifunctional degrader and the bound anti-TSH receptor autoantibody protein are endocytosed, they are released from the ASGPR through calcium depletion from the endosome and changes in binding site amino acid protonation due to decreased pH. The ASGPR is recycled back to the hepatocyte surface. Endocytosed proteins are trafficked to late endosomes, which are fused with lysosomes. Lysosomal proteases then degrade endocytosed proteins, permanently removing them from circulation.

Anti-TSHR autoantibody presence can be measured by methods known to persons having ordinary skill in the art. The inventors tested samples tested in the KRONUS TRAb ELISA. Samples were marked as positive when above the suggested diagnostic threshold of 1 U/L.

Several types of assays are used by persons having ordinary skill in the biomedical art to measure TSH receptor autoantibodies. See European Pat. No EP1021721B1 and Intl. Pat. Publ. WO 2015/189543.

The 4E31 antibody is a mouse monoclonal antibody to residues 603-764 of the C-terminus of the TSH receptor (C-TSHR), which can be used to immobilize the full-length TSH receptor onto ELISA plate wells. See EP1021721B1 (RSR Ltd.) and Bolton et al., Clin Chem., 45, 2285-2287 (1999). The 4E31 antibody can be prepared by immunization with electroeluted C-TSHR/GST fusion protein. See Intl. Pat. Publ. WO 2015/189543. 4E31 is available for purchase from RSR Ltd, Cambridge, UK.

The Chemical Structure of the Composition of Matter (Agent, TRAP).

In one embodiment, the invention provides a composition of matter (agent) comprising:

- a binding moiety that can bind to anti-TSH receptor autoantibody,
- a cellular receptor-binding moiety that binds to hepatocytes or other degrading cells through asialoglycoprotein receptors (ASGPR) of hepatocytes or other cell receptors on the surface of degrading cells in a patient or subject, and
- a linker moiety linking the binding moiety that can bind to anti-TSH receptor autoantibody and the cellular receptor-binding moiety.

In some embodiments, the invention provides a composition of matter (an agent) having a structure selected from the Markush group of structures consisting of:

[AGN101]

$R^{CN}$—(Xaa)y—$R^{CC}$, 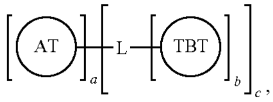 ,

[AGN102]

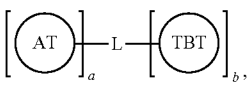 , or a pharmaceutically acceptable salt thereof. In these structures, a, b, and c may independently be an integer of 1 or greater. In some embodiments, each cellular receptor-binding moiety independently has the structure of —($R^{CN}$—(Xaa)γ-$R^{CC}$) or salt form thereof.

In some embodiments, the agent has the structure of formula AGN101:

[AGN101]

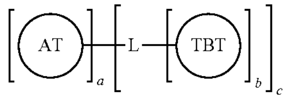

or a pharmaceutically acceptable salt thereof, wherein:
each of a, b, and c is independently 1-200;
each AT is independently a binding moiety;
L is a linker moiety; and
each TBT is independently a cellular receptor-binding moiety,
wherein the anti-TSH receptor autoantibody-binding moiety is an antigen protein, an antigen protein variant, or a fragment thereof.

In some embodiments, the agent has the structure of formula AGN102:

[AGN102]

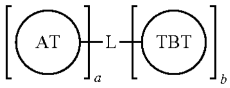

or a pharmaceutically acceptable salt thereof, wherein:
each of a and b is independently 1-200;
each AT is independently a binding moiety;
L is a linker moiety; and
each TBT is independently a cellular receptor-binding moiety, wherein the anti-TSH receptor autoantibody-binding moiety is an antigen protein, an antigen protein variant, or a fragment thereof.

In some embodiments, an agent comprises one and no more than one binding moiety. In some embodiments, one or no more than one binding moiety is bound to a linker moiety. In some embodiments, a is 1. In some embodiments, a is 2 or more. In some embodiments, one and no more than one cellular receptor-binding moiety is bonded to a linker moiety. In some embodiments, b is 1. In some embodiments, two or more cellular receptor-binding moieties are bonded to a single linker moiety. In some embodiments, b is 2 or more. In some embodiments, an agent comprises one and no more than one cellular receptor-binding moiety. In some embodiments, c is 1. In some embodiments, b is 1 and c is 1. In some embodiments, a is 1, b is 1 and c is 1. In some embodiments, an agent comprises two or more anti-TSH receptor autoantibody-binding moieties. In some embodiments, b is 2 or more and c is 1. In some embodiments, b is 2 or more and c is 2 or more. In some embodiments, b is 1, and c is 2 or more.

In some embodiments, c is 1-20, e.g., 1, 2, 3, 4, 5, 6, 7, 8, 9, 10, 11, 12, 13, 14, 15, 16, 17, 18, 19, or 20. In some embodiments, c is selected from the Markush group of size ranges, where c is 1-15, c is 1-10, c is 1-9, c is 1-8, c is 1-7, c is 1-6, c is 1-5, c is 1-4, c is 1-3, and c is 1-2. In some embodiments, c is a size selected from the Markush group of sizes consisting of 1, 2, 3, 4, 5, 6, 7, 8, and 9.

In some embodiments, each cellular receptor-binding moiety in an agent is the same. In some embodiments, each linker moiety connecting a cellular receptor-binding moiety to an antibody moiety is the same. In some embodiments, the TBT in agents is the same. In some embodiments, the $-L-(TBT)_b$ are the same.

In some embodiments, b is 1. In some embodiments, c is 1. In some embodiments, c is two or more. In some embodiments, c is 2. Persons having ordinary skill in the biomedical art know that several technologies can be used to conjugate antibody moieties with anti-TSH receptor autoantibody-binding moieties, e.g., certain technologies used for preparing antibody-drug conjugates in accordance with this specification. In some embodiments, anti-TSH receptor autoantibody-binding moieties are connected to antibody moieties through certain types of groups or amino acid residues. In some embodiments, anti-TSH receptor autoantibody-binding moieties are connected to lysine residues optionally through linker moieties. In some embodiments, anti-TSH receptor autoantibody-binding moieties are connected to cysteine residues optionally through linker moieties. In some embodiments, anti-TSH receptor autoantibody-binding moieties are connected to unnatural amino acid residues optionally through linker moieties. In some embodiments, the invention provides technologies for selectively linking anti-TSH receptor autoantibody-binding moieties to certain amino acid residues optionally through linker moieties. In some embodiments, provided technologies selectively connect anti-TSH receptor autoantibody-binding moieties to certain types of amino acid residues, e.g., lysine residues, optionally through linker moieties. In some embodiments, provided technologies selectively connect anti-TSH receptor autoantibody-binding moieties to sites of antibody moieties optionally through linker moieties. In some embodiments, provided technologies selectively connect anti-TSH receptor autoantibody-binding moieties to certain types of amino acid residues at sites optionally through linker moieties. In some embodiments, anti-TSH receptor autoantibody-binding moieties are connected to K246 and K248 of an IgG1 heavy chain and amino acid residues corresponding thereto optionally through linker moieties. In some embodiments, anti-TSH receptor autoantibody-binding moieties are connected to K251 and K253 of an IgG2 heavy chain and amino acid residues corresponding thereto optionally through linker moieties. In some embodiments, anti-TSH receptor autoantibody-binding moieties are connected to K239 and K241 of a heavy chain and amino acid residues corresponding thereto optionally through linker moieties. In some embodiments, a cellular receptor-binding moiety is connected to a particular amino acid residue or site optionally through a linker. In some embodiments, each cellular receptor-binding moiety is independently connected to a particular amino acid residue or site optionally through a linker.

As known by persons having ordinary skill in the biomedical art, an antibody agent may comprise more than one site, e.g., one on each of the more than one chain, e.g., one or each heavy chain. In some embodiments, an antibody moiety comprises two heavy chains. One or both amino acid residues or amino acid residues corresponding thereto are each independently connected to a cellular receptor-binding moiety optionally through a linker. In some embodiments, one and no more than one is connected. In some embodiments, c is 1. In some embodiments, both are connected. In some embodiments, c is 2. In some embodiments, both anti-TSH receptor autoantibody-binding moieties or both linker moieties (if any) are the same.

In some embodiments, an agent comprises one and no more than one binding moiety. In some embodiments, one or no more than one binding moiety is bound to a linker moiety. In some embodiments, a is 1. In some embodiments, an agent comprises two or more moieties. In some embodiments, two or more moieties are bound to a single linker moiety. In some embodiments, a is 2 or more. In some embodiments, one and no more than one cellular receptor-binding moiety is bonded to a linker moiety. In some embodiments, b is 1. In some embodiments, two or more cellular receptor-binding moieties are bonded to a single linker moiety. In some embodiments, b is 2 or more. In some embodiments, an agent comprises one and no more than one cellular receptor-binding moiety. In some embodiments, c is 1. In some embodiments, b is 1 and c is 1. In some embodiments, a is 1, b is 1, and c is 1. In some embodiments, an agent comprises two or more anti-TSH receptor autoantibody-binding moieties. In some embodiments, b is 2 or more and c is 1. In some embodiments, b is 2 or more and c is 2 or more. In some embodiments, b is 1 and c is 2 or more.

In some embodiments, c is 1-20, e.g., 1, 2, 3, 4, 5, 6, 7, 8, 9, 10, 11, 12, 13, 14, 15, 16, 17, 18, 19, or 20. In some embodiments, c is selected from the Markush group of size ranges, where c is 1-15, c is 1-10, c is 1-9, c is 1-8, c is 1-7, c is 1-6, c is 1-5, c is 1-4, c is 1-3, and c is 1-2. In some embodiments, c is a size selected from the Markush group of sizes consisting of 1, 2, 3, 4, 5, 6, 7, 8, and 9.

In some embodiments, each cellular receptor-binding moiety in an agent is the same. In some embodiments, each linker moiety connecting a cellular receptor-binding moiety to an antibody moiety is the same. In some embodiments, the TBT in agents is the same. In some embodiments, $-L-(TBT)_b$ is the same.

In some embodiments, b is 1. In some embodiments, c is 1. In some embodiments, c is two or more. In some embodiments, c is 2. Persons having ordinary skill in the biomedical art know that several technologies can be used to conjugate antibody moieties with anti-TSH receptor autoantibody-binding moieties, e.g., certain technologies used for preparing antibody-drug conjugates in accordance with this specification. In some embodiments, anti-TSH receptor autoantibody-binding moieties are connected to antibody moieties through certain types of groups or amino acid residues. In some embodiments, anti-TSH receptor autoantibody-binding moieties are connected to lysine residues optionally through linker moieties. In some embodiments, anti-TSH receptor autoantibody-binding moieties are connected to cysteine residues optionally through linker moieties. In some embodiments, anti-TSH receptor autoantibody-binding moieties are connected to unnatural amino acid residues optionally through linker moieties. In some embodiments, the invention provides technologies for selectively linking anti-TSH receptor autoantibody-binding moieties to certain amino acid residues optionally through linker moieties. In some embodiments, provided technologies selectively connect anti-TSH receptor autoantibody-binding moieties to certain types of amino acid residues, e.g., lysine residues, optionally through linker moieties. In some embodiments, provided technologies selectively connect anti-TSH receptor autoantibody-binding moieties to sites of antibody moieties optionally through linker moieties. In some embodiments, provided technologies selectively connect anti-TSH receptor autoantibody-binding moieties to certain types of amino acid residues at sites optionally through linker moieties. In some embodiments, anti-TSH receptor autoantibody-binding moieties are connected to K246 and K248 of an IgG1 heavy chain and amino acid residues corresponding thereto optionally through linker moieties. In some embodiments, anti-TSH receptor autoantibody-binding moieties are connected to K251 and K253 of an IgG2 heavy chain and amino acid residues corresponding thereto optionally through linker moieties. In some embodiments, anti-TSH receptor autoantibody-binding moieties are connected to K239 and K241 of a heavy chain and amino acid residues corresponding thereto optionally through linker moieties. In some embodiments, a cellular receptor-binding moiety is connected to a particular amino acid residue or site optionally through a linker. In some embodiments, each cellular receptor-binding moiety is independently connected to a particular amino acid residue or site optionally through a linker.

As known by persons having ordinary skill in the biomedical art, an antibody agent may comprise more than one site, e.g., one on each of the more than one chain, e.g., one or each heavy chain. In some embodiments, an antibody moiety comprises two heavy chains. One or both amino acid residues or amino acid residues corresponding thereto are each independently connected to a cellular receptor-binding moiety optionally through a linker. In some embodiments, one and no more than one is connected. In some embodiments, c is 1. In some embodiments, both are connected. In some embodiments, c is 2. In some embodiments, both anti-TSH receptor autoantibody-binding moieties or both linker moieties (if any) are the same.

In some embodiments, the composition of matter has the structure of:

Formula (I)

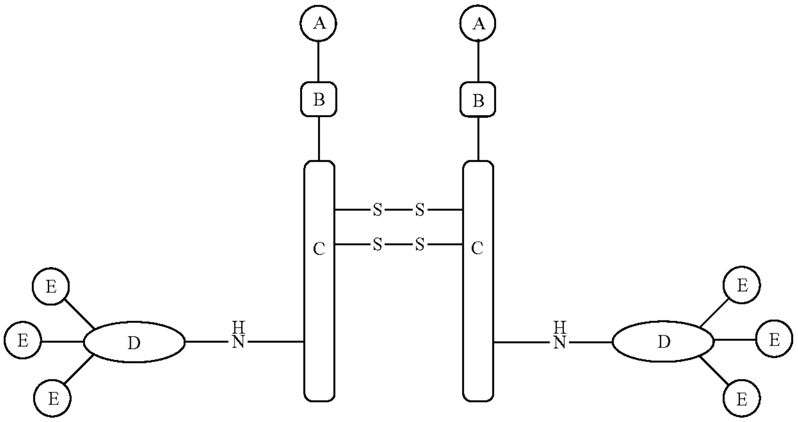, wherein, each 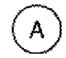 is a moiety having the peptide sequence of SEQ ID NO: 7 or a sequence having 95% sequence identity therewith;

each 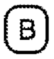 is a means for connecting 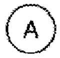 and

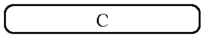;

each

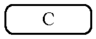

is a peptide moiety having SEQ ID NO: 8, wherein the moieties

are linked together via two disulfide bridges

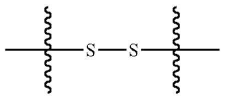 [SMILES: *SS*]

as shown in Formula (II), wherein one disulfide bridge links cysteine residues located in position 11 of SEQ ID NO: 8 of each moiety

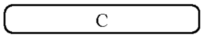 , and wherein the other disulfide bridge links cysteine residues located in position 14 of SEQ ID NO: 8 of each moiety

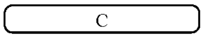 ;

each

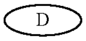

is a means for connecting

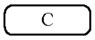

and 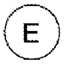, wherein each

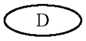

is connected to

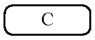

via a side chain amino group of a lysine residue of

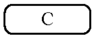

to form

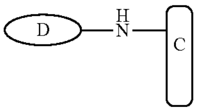 ;

and each 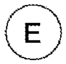 is an asialoglycoprotein receptor ("ASGPR") binding moiety comprising an N-acetyl-D-galactosamine ("GalNAc") group having Formula (II):

Formula (II)

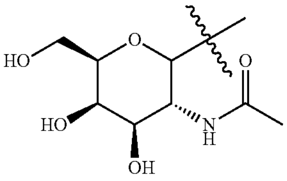 .

In another embodiment, each  has the peptide sequence of SEQ ID NO: 7.

In another embodiment, 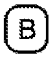 is a single bond or a peptide connecting moiety comprising an amino acid selected from the group consisting of glycine (G), glutamate (E), leucine (L), proline (P), glutamine (Q), serine(S), and threonine (T).

In another embodiment, each 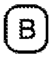 has the peptide sequence of SEQ ID NO: 9.

In another embodiment, each

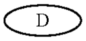

comprises a moiety selected from the Markush group consisting of:

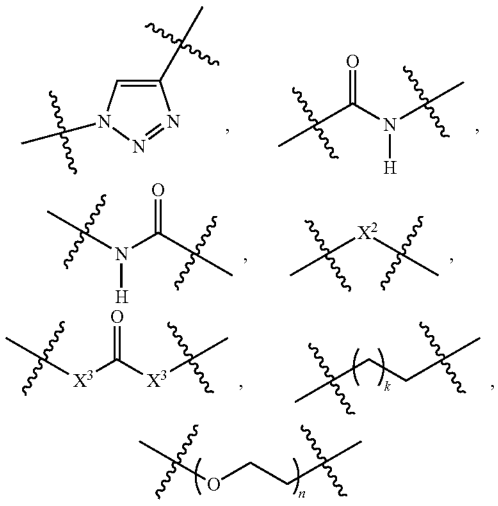

wherein, $X^2$ are independently $CH_2$, O, S, $NR^4$, C(O), S(O), $S(O)_2$, $S(O)_2O$, $OS(O)_2$, or $OS(O)_2O$;

$X^3$ are independently O, S, $NR^4$, wherein $R^4$ is H or a $C_1$-$C_3$ alkyl; and k and n are independently 1 to 25.

In another embodiment, each 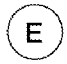 further comprises a moiety selected from the group consisting of:

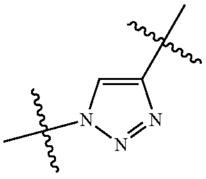,
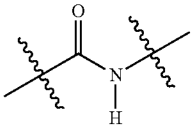,
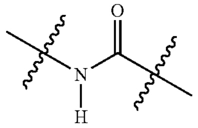,
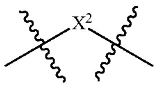,
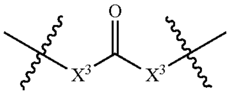,
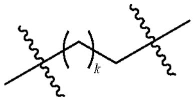,
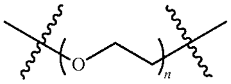

wherein, $X^2$ are independently $CH_2$, O, S, $NR^4$, C(O), S(O), $S(O)_2$, $S(O)_2O$, $OS(O)_2$, or $OS(O)_2O$;

$X^3$ are independently O, S, $NR^4$, wherein $R^4$ is H or a $C_1$-$C_3$ alkyl;

k and n are independently 1 to 25.

In another embodiment, each

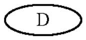

comprises one or more —(O)C—$[(CH_2)_nO]_m(CH_2)_n$NH—, —$[(CH_2)_nO]_m(CH_2)_n$NHC(O)$[(CH_2)_nO]_m$—, and —$[(CH_2)_n\ O]_m(CH_2)_n\{NHC(O)[(CH_2)_nO]_m\}_p(CH_2)_n$C(O)NH—, wherein each m and n are independently 1 to 10.

In another embodiment, each

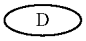

comprises one or more —$[(CH_2)_n$—$O]_m$—, wherein each m and n are independently 1 to 10.

In another embodiment, each

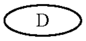

comprises —$(CH_2)_n$—O—$(CH_2CH_2O)_n$—$(CH_2)_n$—, wherein each n is independently 1 to 10.

In another embodiment, each 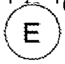 comprises a group having by Formula (IIa):

Formula (IIa)

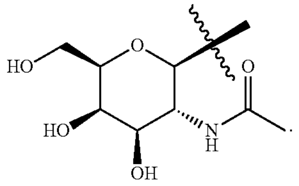

In another embodiment, each

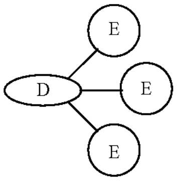

comprises a group having Formula (III):

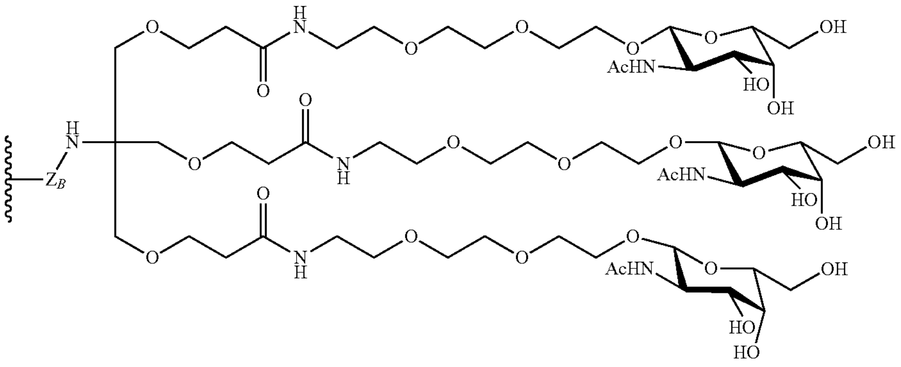

wherein, $Z_B$ is absent, —$(CH_2)_{IM}$—, —C(═O)—$(CH_2)_{IM}$—, or —C(═O)—$(CH_2)_{IM}$—$NR^M$—;

$R^M$ is H or $C_1$-$C_3$ alkyl; and each occurrence of IM is independently 1, 2, or 3.

In another embodiment, each
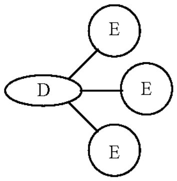
comprises a group having Formula (IV) or Formula (V):
Formula (IV)
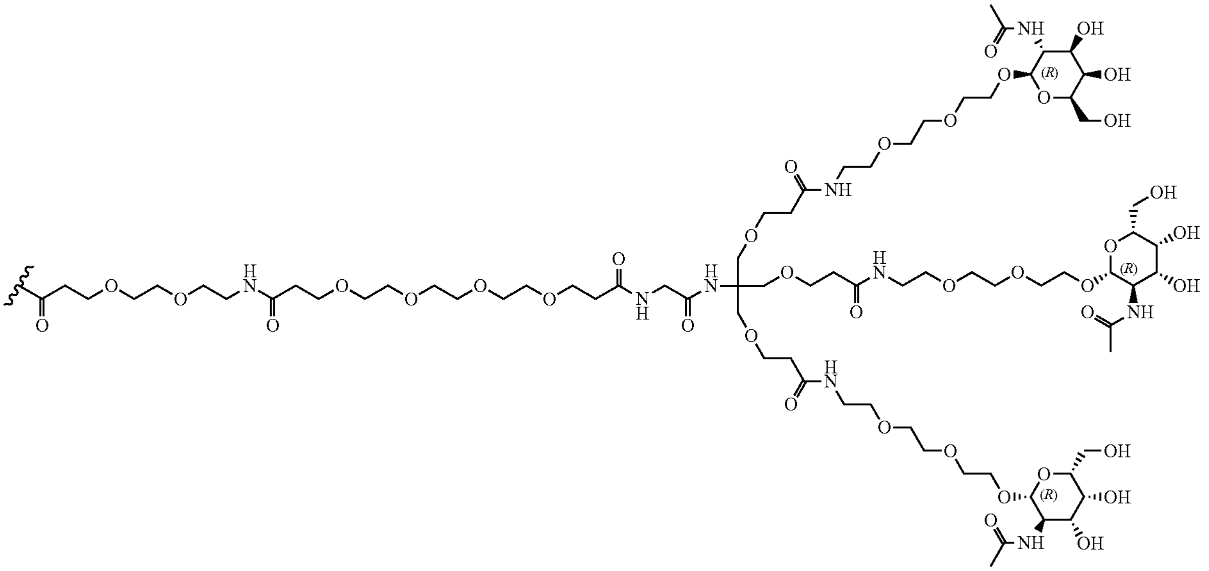
Formula (V)
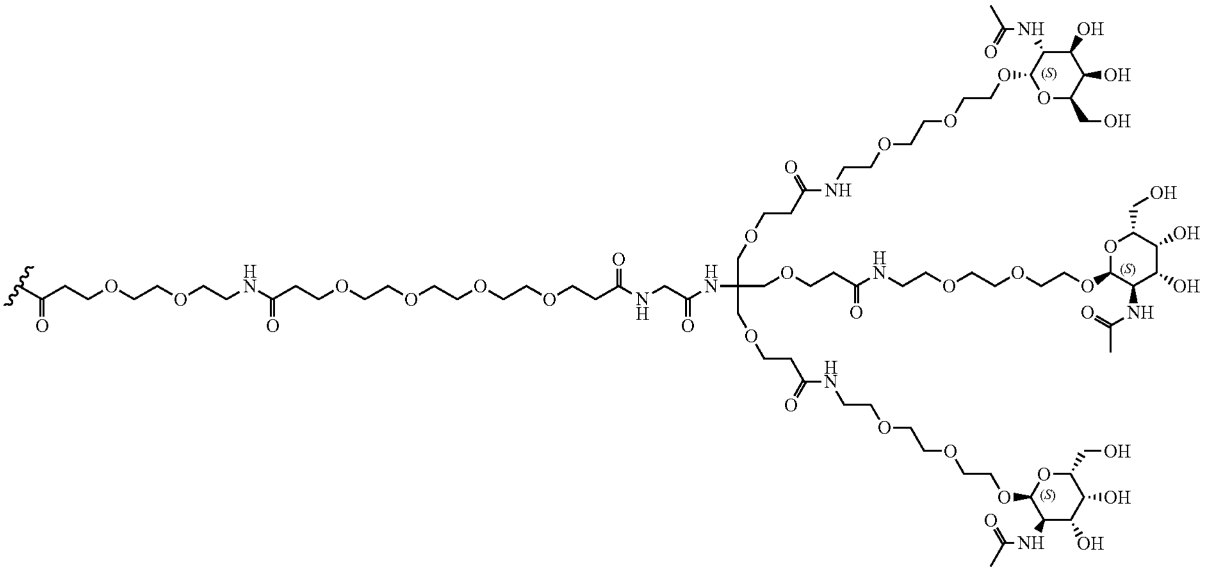

In another embodiment, the lysine residue of

C is located in position 31 or position 33 of SEQ ID NO: 8.

In another embodiment, the cysteine residues in positions 46 and 106 of SEQ ID NO: 8 are connected to form a disulfide bridge, and wherein the cysteine residues in positions 152 and 210 of SEQ ID NO: 8 are connected to form a disulfide bridge.

In a specific embodiment, the composition of matter is AGN301.

Anti-TSH Receptor Autoantibody Binding Moiety Ⓐ

In an embodiment, the anti-TSH receptor (anti-TSHR) binding moiety Ⓐ may be a moiety derived from the TSH receptor. The thyroid-stimulating hormone (TSH) receptor (TSHR) is involved in the control of thyroid function and is a major autoantigen in autoimmune thyroid diseases. The TSHR is a member of the G-protein coupled receptor (GPCR) family and consists of three domains: the extracellular leucine-rich repeat domain (LRD), the hinge region and a transmembrane domain (TMD) with an intracellular C-terminus (Nunez Miguel R et al (2004) Thyroid 14:991-1011). TSHR260 is a subdomain of TSHR consisting of residues 22-260 and encompassing most of the LRD (Sanders J et al (2007) Thyroid 17:395-410. The TSHR260 shows similar binding to TRAbs as the full-length TSHR (Rees Smith B er a/(2009) Hormone and Metabolic Research 41:448-455 and International Patent Publication WO 2010/073012).

Proteins such as TSHR and TSHR260 have poor stability and are denatured during purification. Accordingly, more thermostable proteins, for example more thermostable TSHR260 and full length TSHR have been created and described. See, for example, EP 3155011 A2, which is incorporated herein in its entirety by reference.

In an embodiment, a mutant TSHR or fragment thereof may include a single point mutation. Such mutation may be P28E, L59F, T62V, H63C, L64Y, R112P, P142I, D143P, D151E, S166T, I167F, P168Y, V169R, N170W, T179C, I253R, or R255Y.

In another embodiment, Ⓐ may be a mutant TSHR or fragment thereof containing two point mutations. One of these mutations may be I253R, and the second mutation may be P28E, L59F, T62V, H63C, L64Y, R112P, P142I, D143P, D151E, S166T, I167F, P168Y, V169R, N170W, T179C, or R255Y. In another aspect, a mutant TSHR or fragment thereof may contain three point mutations. One of these mutations may be I253R, the second mutation may be D143P, and the third mutation may be one of P28E, L59F, T62V, H63C, L64Y, R112P, P142I, D151E, S166T, P168Y, V169R, and N170W.

In another embodiment, Ⓐ may be a mutant TSHR or fragment thereof containing four point mutations. One of these mutations may be I253R, the second mutation may be D143P, the third mutation may be R112P, and the fourth mutation may be one of L59F, H63C, D151E, S166T, V169R, and N170W.

In another embodiment, Ⓐ may be a mutant TSHR or fragment thereof containing five point mutations. One of these mutations may be I253R, the second mutation may be D143P, the third mutation may be R112P, the fourth mutation may be D151E or H63C, and a fifth mutation may be one of L59F, (H63C or D151E), S166T and V169R.

In another embodiment, Ⓐ may be a mutant TSHR or fragment thereof containing six mutations. One of these mutations may be I253R, the second mutation may be D143P, the third mutation may be R112P, the fourth mutation may be D151E, the fifth mutation may be H63C, and the sixth mutation may be either S166T or V169R.

In another embodiment, Ⓐ may be a mutant TSHR or fragment thereof containing from one, two, three, four, five, or six point mutations selected from P28E, L59F, T62V, H63C, L64Y, R112P, P142I, D143P, D151E, S166T, I167F, P168Y, V169R, N170W, T179C, I253R, and R255Y.

In another embodiment, Ⓐ may be a mutant TSHR or fragment thereof including the subdomain TSHR260 of the TSHR receptor and preferably may also include one of the following set of mutations:

1) I253R;
2) I253R and one of the following: P28E, L59F, H63C, L64Y, R112P, D143P, D151E, S166T, P168Y, V169R, or N170W;
3) I253R and D143P and one of the following: L59F, H63C, R112P, D151E, S166T, or V169R;
4) I253R and D143P and R112P and one of the following: L59F, H63C, D151E, S166T, or V169R;
5) I253R and D143P and R112P and D151E and one of the following: L59F, H63C, S166T, or V169R;
6) I253R and D143P and R112P and D151E and H63C and one of the following: S166T or V169R; and
7) I253R and D143P and R112P and H63C and one of the following: S166T or V169R.

In another embodiment, Ⓐ may be the mutant TSHR or fragment thereof including the subdomain TSHR260 of the TSHR receptor and preferably may also include one of the following set of mutations:

1)

$$I253R;$$

2)

$$D143P+I253R;$$

3)

$$R112P+D143P+I253R;$$

4)

$$R112P+'O143P+D151E+I253R;$$

5)

$$R112P+D143P+D151E+V169R+I253R;$$

6)

$$H63C+R112P+D143P+D151E+V169R+I253R;$$

-continued

7)

$$H63C+R112P+D143P+V169R+I253R;\text{ or}$$

8)

$$H63C+R112P+D143P+S166T+I253R.$$

In another embodiment, A may be the TSHR260 mutant or fragment thereof that is stabilized by the introduction of six mutations (H63C, R112P, D143P, D151E, V169R and I253R) to form TSHR260-JMG55™, which is approximately 900 times more thermostable than wild-type TSHR260. Such TSHR260 mutant was described in Jennifer Miller-Gallacher et al. "Crystal structure of a ligand-free stable TSH receptor leucine-rich repeat domain" Journal of Molecular Endocrinology (2019)62, 117-128, which is incorporated herein in its entirety by reference.

In an embodiment, A may be the anti-TSH receptor autoantibody-binding moiety ABT301 (SEQ ID NO: 7) or a conjugation reaction derivative thereof. In another embodiment, A may be the anti-TSH receptor autoantibody-binding moiety including a sequence having 80% or greater sequence identity with SEQ ID NO: 7. For example, the sequence identity with SEQ ID NO: 7 may be 80% or greater, 85% or greater, 90% or greater, 95% or greater, 96% or greater, 97% or greater, 98% or greater, or 99% or greater Linking Moiety B Linking moiety B serves as a spacer structure connecting moieties A and

C.

A spacer is a structure that is located between different structural modules and can spatially separate the structural modules. The definition of spacer is not limited by whether it has a certain function or whether it can be cleaved or degraded in vivo. Examples of spacers include but are not limited to amino acids and non-amino acid structures, wherein non-amino acid structures can be, but are not limited to, amino acid derivatives or analogues. In an embodiment a spacer structure may include a spacer sequence. As used herein, "spacer sequence" refers to an amino acid sequence serving as a spacer, and examples thereof include but are not limited to a single amino acid, a sequence containing a plurality of amino acids, for example, a sequence containing two amino acids such as GA, etc., or, for example, GGGGS, GGGGSGGGGS, GGGGSGGGGSGGGGS, etc.

In Formula (I), B may be a single chemical bond or a polypeptide that provides separation between the TSHR binding moiety A and Fc polypeptide moiety

C.

In an embodiment, B may be a peptide connecting moiety comprising an amino acid selected from the group consisting of G, E, L, P, Q, S, and T.

In an embodiment, B may include a $(G4S)_4$ linker. For example, B may include a G4S polypeptide having sequence GGGGS. In another example, B may include a 2XG4S polypeptide having sequence GGGGGGGGS. In another example, B may include a 3XG4S polypeptide having sequence GGGGSGGGGSGGGGS. In another example, B may include a 4XG4S polypeptide having sequence GGGGSGGGGSGGGGSGGGGS. In another example, B may include a 5XG4S polypeptide having sequence GGGGSGGGGGGGGSGGGGSGGGGS.

In an embodiment, B may include a G4S polypeptide and further include one or more of the amino acids selected from the group consisting of E, P, K, and A. For example, B may be a polypeptide having the sequence GGGGSEPKSA.

Methods of connecting or fusing the TSHR binding moiety A and Fc polypeptide moiety

C are known in the art. Either one or both moieties may have a recognition sequence $G_n$ of a ligase acceptor substrate, which facilitates enzyme-catalyzed coupling of compound of formula (I) with the targeting molecule under the catalysis of the ligase. The targeting molecule optionally modified and comprises the corresponding recognition sequence of a ligase acceptor substrate. In an embodiment, A, B, and

C may be linked together to constitute a part of a continuous recombinant protein sequence.

In an embodiment, the ligase may be a transpeptidase. In an embodiment, the ligase may be selected from the group consisting of a natural transpeptidase, an unnatural transpeptidase, variants thereof, and the combination thereof. Unnatural transpeptidase enzymes can be, but are not limited to, those obtained by engineering of natural transpeptidase. In an embodiment, the ligase may be selected from the group consisting of a natural Sortase, an unnatural Sortase, and the combination thereof. The species of natural Sortase include Sortase A, Sortase B, Sortase C, Sortase D, Sortase *L. plantarum*, etc. (detailed description can be found in US20110321183 A1, which is incorporated herein by reference). The type of ligase corresponds to the ligase recognition sequence and is thereby used to achieve specific conjugation between different molecules or structural fragments.

In some embodiments, the ligase may be a Sortase selected from Sortase A, Sortase B, Sortase C, Sortase D and Sortase *L. plantarum*. In these embodiments, the recognition sequence of the ligase acceptor substrate may be selected from the group consisting of oligomeric Glycine, oligomeric alanine, and a mixture of oligomeric Glycine/alanine having a degree of polymerization of 3-10. In a particular embodiment, the recognition sequence of the ligase acceptor substrate may be $G_n$, wherein G is Glycine (Gly), and n is an integer of 2 to 10.

In another embodiment, the ligase may be Sortase A from *Staphylococcus aureus*. Accordingly, the ligase recognition sequence may be typical recognition sequence of the enzyme as LPXTG. In yet another particular embodiment, the recognition sequence of the ligase donor substrate may be LPXTGJ, and the recognition sequence of the ligase acceptor substrate may be $G_n$, wherein X can be any single amino acid that is natural or unnatural; J may be absent, or may be an amino acid fragment comprising 1-10 amino acids, optionally labeled. In an embodiment, J may be absent. In yet another embodiment, J may be an amino acid fragment comprising 1-10 amino acids, wherein each amino acid may be independently any natural or unnatural amino acid. In another embodiment, J may be $G_m$, wherein m may be an integer of 1 to 10. In yet another embodiment, the recognition sequence of the ligase donor substrate may be LPETG. In another particular embodiment, the recognition sequence of the ligase donor substrate may be LPETGG.

In an embodiment, the ligase may be Sortase B from *Staphylococcus aureus* and the corresponding donor substrate recognition sequence may be NPQTN. In another embodiment, the ligase may be Sortase B from *Bacillus anthracis* and the corresponding donor substrate recognition sequence may be NPKTG.

In yet another embodiment, the ligase may be Sortase A from *Streptococcus pyogenes* and the corresponding donor substrate recognition sequence may be LPXTGJ, wherein J may be as defined above. In another embodiment, the ligase may be Sortase subfamily 5 from *Streptomyces coelicolor*, and the corresponding donor substrate recognition sequence may be LAXTG.

In yet another embodiment, the ligase may be Sortase A from *Lactobacillus plantarum* and the corresponding donor substrate recognition sequence may be LPQTSEQ.

The ligase recognition sequence can also be other totally new recognition sequence for transpeptidase optimized by manual screening.

Polypeptide Moiety

C

In an embodiment, the polypeptide moiety

C may be a Fc fragment generated from the heavy chain constant region of an immunoglobulin, an Fc monomer, an Fc dimer, or fragments thereof (e.g., synthetic peptides). For example,

C may be an Fc-monomer. In some embodiments, the Fc fragment may be conjugated to a single variable domain on a heavy chain (VHH) antibody, a nanobody, a domain, or a fragment thereof, to form an VHH antigen fusion. In some embodiments, the Fc polypeptide may be conjugated to an antigen to form an Fc-antigen fusion. In various embodiments, the Fc fragment may be conjugated to the TSHR bonding moiety A through the linking polypeptide B.

In an embodiment, the polypeptide moiety

C may have SEQ ID NO: 8. In another embodiment, the polypeptide moiety

C may have a sequence having 80% or greater sequence identity with SEQ ID NO: 8. For example, the sequence identity with SEQ ID NO: 8 may be 80% or greater, 85% or greater, 90% or greater, 95% or greater, 96% or greater, 97% or greater, 98% or greater, or 99% or greater.

Linking Group

D

Various linkers described in the art may be used as the linking groups

D in Formula (I) according to embodiments of the present invention.

In an embodiment, each linking group

D in Formula (I) may include any of the linkers [LINKERS] and [CON] disclosed in International Patent Publication WO 2019/199634, which is incorporated herein in its entirety by reference.

In another embodiment, each linking group

D in Formula (I) may include any of the linkers [LinkerA], [LinkerB], [LinkerC], and [LinkerD] disclosed in International Patent Publication WO 2021/155317, which is incorporated herein in its entirety by reference.

In another embodiment, each linking group

in Formula (I) may include any of the linkers L disclosed in International Patent Publication WO 2024155750, which is incorporated herein in its entirety by reference.

In an embodiment, each in Formula (I) may include one or more —(O)C—$[(CH_2)_nO]_m(CH_2)_n$NH—, —$[(CH_2)_nO]_m(CH_2)_n$NHC(O)$[(CH_2)_nO]_m$—, and —$[(CH_2)_nO]_m(CH_2)_n${NHC(O)$[(CH_2)_nO]_m\}_p(CH_2)_n$C(O)NH—, wherein each m and n are independently 1 to 10.

In another embodiment, each

in Formula (I) may include one or more —$[(CH_2)_n$—$O]_m$—, wherein each m and n are independently 1 to 10.

In another embodiment, each

in Formula (I) may include —$(CH_2)_n$—O—$(CH_2CH_2O)_n$—$(CH_2)_n$—, wherein each n is independently 1 to 10.

In an embodiment, each

in Formula (I) may include a moiety selected from the group consisting of:

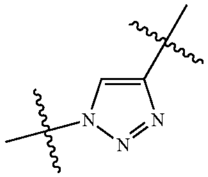
,
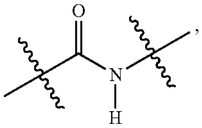
,
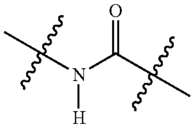
,
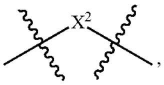
,
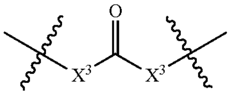
,
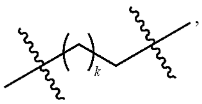
,
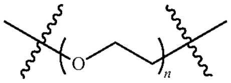

wherein, $X^2$ are independently $CH_2$, O, S, $NR^4$, C(O), S(O), $S(O)_2$, $S(O)_2O$, $OS(O)_2$, or $OS(O)_2O$;

$X^3$ are independently O, S, $NR^4$, wherein $R^4$ is H or a $C_1$-$C_3$ alkyl; and k and n are independently 1 to 25.

ASGPR Binding Moiety 

Various ASGPR binding moieties described in the art may be used as the ASGPR binding moieties  in Formula (I) according to embodiments of the present invention.

In an embodiment, each ASGPR binding moiety  in Formula (I) may include any of the moieties [CRBM] and [ASGPRBM] disclosed in International Patent Publication WO 2019/199634, which is incorporated herein in its entirety by reference.

In another embodiment, each ASGPR binding moiety  in Formula (I) may include any of the galactose and mannose ASGPR binding moieties disclosed in International Patent Publication WO 2021/155317, which is incorporated herein in its entirety by reference.

In another embodiment, each ASGPR binding moiety  in Formula (I) may include any of the lysosomal targeting moieties X disclosed in International Patent Publication WO 2024/155750, which is incorporated herein in its entirety by reference.

In an embodiment, each ASGPR binding moiety  in Formula (I) may include a group having by Formula (IIa):

Formula (IIa)

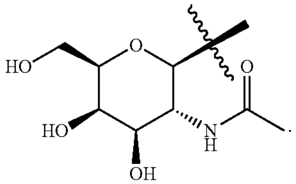
.

In an embodiment, each ASGPR binding moiety  selected from the group consisting of: may further include a moiety

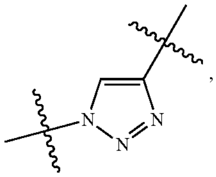
,
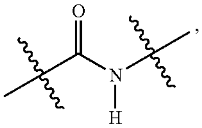
,

-continued

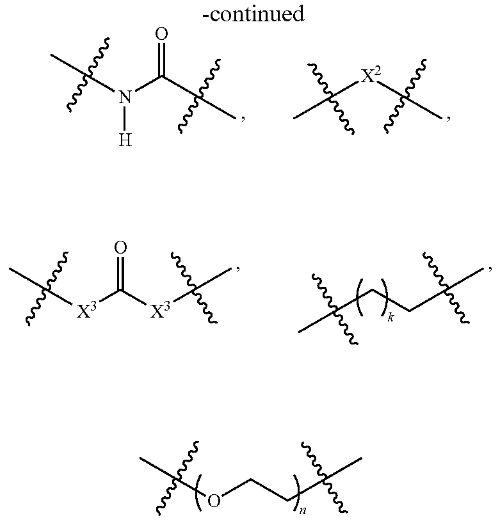

wherein, $X^2$ are independently $CH_2$, O, S, $NR^4$, C(O), S(O), $S(O)_2$, $S(O)_2O$, $OS(O)_2$, or $OS(O)_2O$;

$X^3$ are independently O, S, $NR^4$, wherein $R^4$ is H or a $C_1$-$C_3$ alkyl;

k and n are independently 1 to 25.

In an embodiment, each

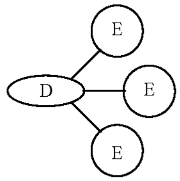

in Formula (I) may include a group having Formula (III):

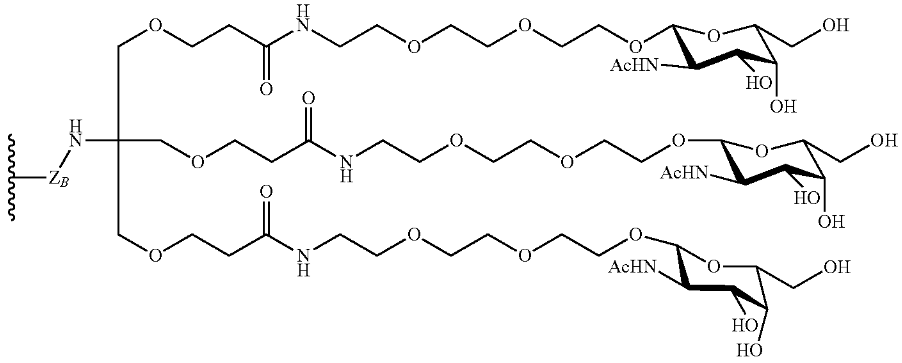

wherein, $Z_B$ is absent, $-(CH_2)_{IM}-$, $-C(=O)-(CH_2)_{IM}-$, or $-C(=O)-(CH_2)_{IM}-NR^M-$;

$R^M$ is H or $C_1$-$C_3$ alkyl; and each occurrence of IM is independently 1, 2, or 3.

In an embodiment, each

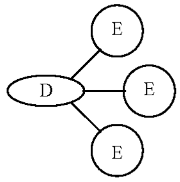

in Formula (I) may include a group having Formula (IV) or Formula (V):

Formula (IV)

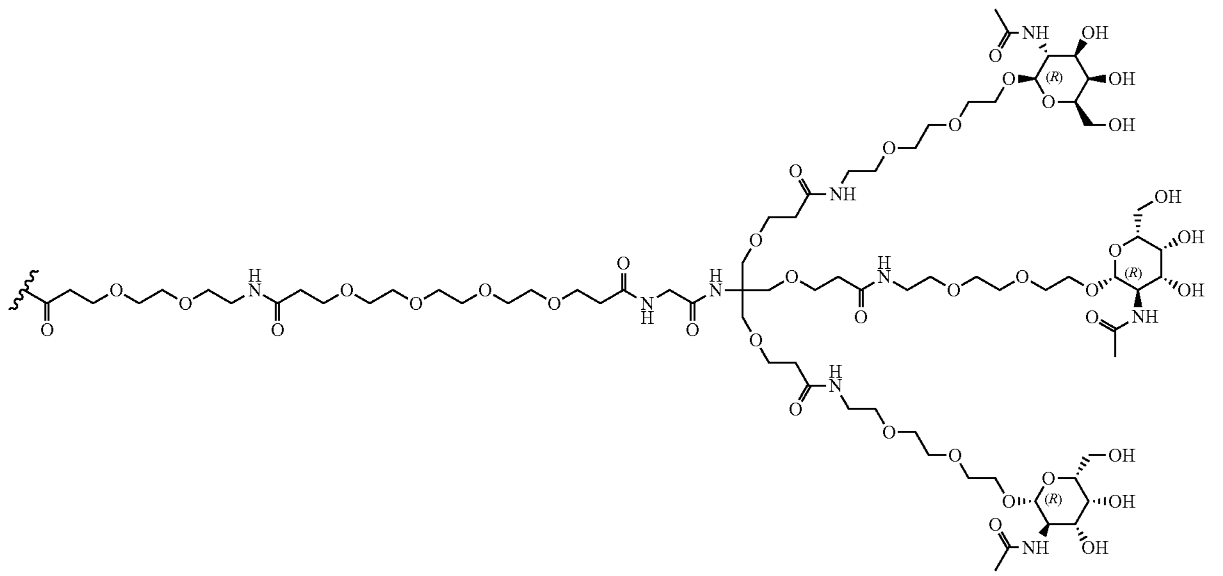

Formula (V)

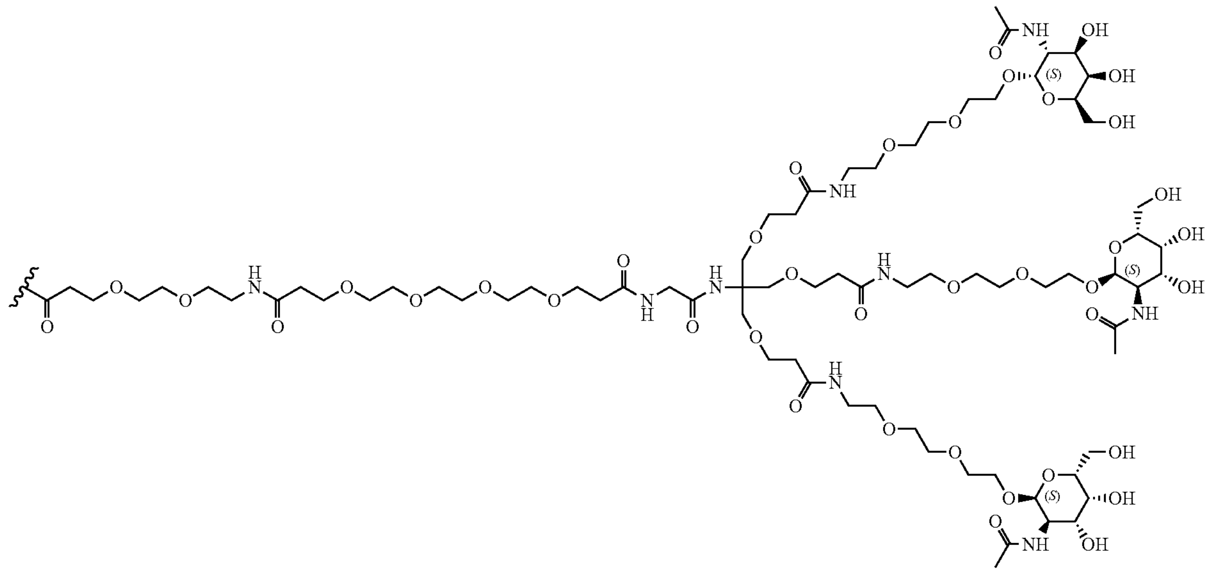

Antibody Fc Binding Moiety.

The composition of matter according to embodiments of the present invention may be prepared by site-specific (MATE™) conjugation of a reagent having binding specificity to the antibody Fc region as described in International Patent Publication WO 2021/102052, which is incorporated herein in its entirety by reference. This process provides attachment of the linking moiety

to Fc moiety

of the described composition of matter.

In some embodiments, the Fc-binding moiety comprises a moiety selected from the Markush group consisting of one or more amino acid residues, a peptide moiety, a cyclic peptide moiety, a peptide comprising one or more natural amino acid residues, and a peptide comprising one or more unnatural natural amino acid residues.

In some embodiments, each binding moiety in an agent is of the same binding moiety or a pharmaceutically acceptable salt thereof.

In some embodiments, the Fc-binding moiety comprises a moiety selected from the Markush group consisting of one or more amino acid residues, a peptide moiety, a cyclic peptide moiety, a peptide comprising one or more natural amino acid residues, and a peptide comprising one or more unnatural natural amino acid residues.

The Fc-binding moiety may comprise:

[ABT101]

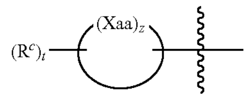

or a pharmaceutically acceptable salt form thereof.

In some embodiments, a binding moiety is or comprises $R^c$-(Xaa)z- or a salt form thereof, wherein each variable is as described in this specification. In some embodiments, a binding moiety comprises ABT101 or a salt form thereof, wherein each variable is as described in this specification.

In some embodiments, a protein-binding moiety is or comprises $R^c$-(Xaa)z- or a salt form thereof, wherein each variable is as described in this specification. In some embodiments, a protein-binding moiety is or comprises ABT101 or a salt form thereof, wherein each variable is as described in this specification.

In some embodiments, a binding moiety, e.g., a universal antibody-binding moiety, is or comprises $R^c$-(Xaa)z- or a salt form thereof, wherein each variable is as described in this specification. In some embodiments, a binding moiety, e.g., a universal antibody-binding moiety, is or comprises ABT101 or a salt form thereof, wherein each variable is as described in this specification. In some embodiments, a binding moiety, e.g., a universal antibody-binding moiety, is $R^c$-(Xaa)z- or ABT101, or a salt form thereof, and is or comprises a peptide unit.

In some embodiments, -(Xaa)z- is or comprises a peptide unit.

In some embodiments, amino acid residues may form bridges, e.g., connections formed by side chains optionally through linker moieties, e.g., L); for example, as in many polypeptides, cysteine residues may form disulfide bridges.

In some embodiments, a peptide unit comprises an amino acid residue, e.g., at physiological pH about 7.4, positively charged amino acid residue, $Xaa^P$), e.g., a residue of an amino acid of formula LNK101 with a positively charged side chain. In some embodiments, a peptide unit comprises R. In some embodiments, at least one Xaa is R.

In some embodiments, ABT101 is a universal antibody-binding moiety. In some embodiments, ABT101 is a universal antibody-binding moiety that can bind to different Fab regions. In some embodiments, ABT101 is a universal antibody-binding moiety that binds to an Fc region, e.g., the Fc region that binds to an Fc receptor.

Several antibody-binding moieties, including universal antibody-binding moieties, can be used following the teachings of this specification. Certain antibody-binding moieties and technologies for identifying or assessing antibody-binding moieties are described in WO2019/023501 and WO2019/136442, each of which is incorporated in this specification in its entirety by reference. Persons having ordinary skill in the biomedical art know that additional technologies in the biomedical art may be suitable for identifying or assessing antibody-binding moieties in accordance with this specification. In some embodiments, an antibody-binding moiety comprises one or more amino acid residues, each independently natural or unnatural.

In some embodiments, a binding moiety, e.g., a protein-binding moiety, e.g., an antibody-binding moiety, e.g., a universal antibody-binding moiety, has the structure of ABT101 or a salt form thereof, wherein:

each of $R^1$, $R^3$ and $R^5$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or:

$R^1$ and $R^{1'}$ are optionally taken together with their intervening carbon atom to form a 3-8 membered optionally substituted saturated or partially unsaturated spirocyclic carbocyclic ring or a 3-8 membered saturated or partially unsaturated spirocyclic heterocyclic ring having 1-2 heteroatoms independently selected from nitrogen, oxygen, or sulfur;

$R^3$ and $R^{3'}$ are optionally taken together with their intervening carbon atom to form a 3-8 membered optionally substituted saturated or partially unsaturated spirocyclic carbocyclic ring or a 3-8 membered saturated or partially unsaturated spirocyclic heterocyclic ring having 1-2 heteroatoms independently selected from nitrogen, oxygen, or sulfur;

an $R^5$ group and the $R^{5'}$ group attached to the same carbon atom are optionally taken together with their intervening carbon atom to form a 3-8 membered optionally substituted saturated or partially unsaturated spirocyclic carbocyclic ring or a 3-8 membered saturated or partially unsaturated spirocyclic heterocyclic ring having 1-2 heteroatoms independently selected from nitrogen, oxygen, or sulfur; or two $R^5$ groups are optionally taken together with their intervening atoms to form a $C_{1-10}$ optionally substituted bivalent straight or branched saturated or unsaturated hydrocarbon chain wherein 1-3 methylene units of the chain are independently and optionally replaced with —S—, —SS—, —N(R)—, —O—, —C(O)—, —OC(O)—, —C(O)O—, —C(O)N(R)—, —N(R)C(O)—, —S(O)—, —$S(O)_2$—, or -$Cy^1$-, wherein each -$Cy^1$- is independently a 5-6 membered heteroarylenyl with 1-4 heteroatoms independently selected from nitrogen, oxygen or sulfur;

each of $R^{1'}$, $R^{3'}$ and $R^{5'}$ is independently hydrogen or optionally substituted $C_{1-3}$ aliphatic;

each of $R^2$, $R^4$ and $R^6$ is independently hydrogen, or optionally substituted $C_{1-4}$ aliphatic, or:

$R^2$ and $R^1$ are optionally taken together with their intervening atoms to form a 4-8 membered, optionally substituted saturated or partially unsaturated monocyclic heterocyclic ring having 1-2 heteroatoms independently selected from nitrogen, oxygen, or sulfur;

$R^4$ and $R^3$ are optionally taken together with their intervening atoms to form a 4-8 membered optionally substituted saturated or partially unsaturated monocyclic heterocyclic ring having 1-2 heteroatoms independently selected from nitrogen, oxygen, or sulfur; or an $R^6$ group and its adjacent $R^5$ group are optionally taken together with their intervening atoms to form a 4-8 membered optionally substituted saturated or partially unsaturated monocyclic heterocyclic ring having 1-2 heteroatoms independently selected from nitrogen, oxygen, or sulfur;

$L^1$ is a trivalent linker moiety; and each of m and n is independently 1, 2, 3, 4, 5, 6, 7, 8, 9, 10, 11, 12, 13, 14, 15, 16, 17, 18, 19, or 20.

In some embodiments, $L^1$ is an optionally substituted trivalent group selected from $C_1$-$C_{20}$ aliphatic or $C_1$-$C_{20}$ heteroaliphatic having 1-5 heteroatoms, wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments $L^1$ is —$(CH_2CH_2O)_{2-4}$— or —$(CH_2CH_2O)_2$—.

In some embodiments, a binding moiety, e.g., a protein-binding moiety, e.g., an antibody-binding moiety, e.g., a universal antibody-binding moiety, has the structure of ABT101 or a salt form thereof, wherein:

each of $R^7$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or:

an $R^7$ group and the $R^{7'}$ group attached to the same carbon atom are optionally taken together with their intervening carbon atom to form a 3-8 membered optionally substituted saturated or partially unsaturated spirocyclic carbocyclic ring or a 3-8 membered optionally substituted saturated or partially unsaturated spirocyclic heterocyclic ring having 1-2 heteroatoms independently selected from nitrogen, oxygen, or sulfur;

each of $R^{7'}$ is independently hydrogen or optionally substituted $C_{1-3}$ aliphatic;

each of $R^8$ is independently hydrogen, or optionally substituted $C_{1-4}$ aliphatic, or:

an $R^8$ group and its adjacent $R^7$ group are optionally taken together with their intervening atoms to form a 4-8 membered optionally substituted saturated or partially unsaturated monocyclic heterocyclic ring having 1-2 heteroatoms independently selected from nitrogen, oxygen, or sulfur; and $R^9$ is hydrogen, optionally substituted $C_{1-3}$ aliphatic, or —C(O)—.

In some embodiments, a binding moiety, e.g., a universal antibody-binding moiety, is or comprises a peptide moiety, e.g., a moiety having the structure of $R^c$-(Xaa)z- or a salt form thereof, wherein each of $R^c$, z, and Xaa is independently as described in this specification. One or more Xaa may be independently an unnatural amino acid residue. Side chains of two or more amino acid residues may be linked together to form bridges. Side chains of two cysteine residues may form a disulfide bridge comprising —S—S—.

In some embodiments, a binding moiety, e.g., a protein-binding moiety, e.g., an antibody-binding moiety, e.g., a universal antibody-binding moiety, is or comprises a cyclic peptide moiety, e.g., a moiety having the structure of ABT101 or a salt form thereof, wherein:

each Xaa is independently a residue of an amino acid or an amino acid analog;

t is 0-50;

z is 1-50;

each $R^c$ is independently -$L^a$-R';

each $L^a$ is independently a covalent bond, or an optionally substituted bivalent group selected from $C_1$-$C_{20}$ aliphatic or $C_1$-$C_{20}$ heteroaliphatic having 1-5 heteroatoms, wherein one or more methylene units of the group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;

each -Cy- is independently an optionally substituted bivalent monocyclic, bicyclic, or polycyclic group wherein each monocyclic ring is independently selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus, and silicon, and a 3-20 membered heterocyclyl ring having 1-10 heteroatoms independently selected from oxygen, nitrogen, sulfur, phosphorus, and silicon;

each R' is independently —R, —C(O)R, —$CO_2$R, or —$SO_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus, and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus, and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic, or polycyclic ring having, in addition to the atom, 0-10 heteroatoms independently selected from oxygen, nitrogen, sulfur, phosphorus, and silicon; or two or more R groups on two or more atoms are optionally and independently taken together with their intervening atoms to form an optionally substituted, 3-30 membered, monocyclic, bicyclic, or polycyclic ring having, in addition to the intervening atoms, 0-10 heteroatoms.

In some embodiments, a peptide unit comprises a functional group in an amino acid residue that can react with a functional group of another amino acid residue. In some embodiments, a peptide unit comprises an amino acid residue with a side chain which comprises a functional group that can react with another functional group of the side chain of another amino acid residue to form a linkage, e.g., see moieties described in TABLE 2 of International Patent Publication WO 2024/228935 (Biohaven Therapeutics, Ltd.). In some embodiments, one functional group of one amino acid residue is connected to a functional group of another amino acid residue to form a linkage (or bridge). Linkages are bonded to backbone atoms of peptide units and comprise no backbone atoms. In some embodiments, a peptide unit comprises a linkage formed by two side chains of non-neighboring amino acid residues. In some embodiments, a linkage is bonded to two backbone atoms of two non-neighboring amino acid residues. In some embodiments, both backbone atoms bonded to a linkage are carbon atoms.

Persons having ordinary skill in the biomedical art know that an amino acid residue may be replaced by another amino acid residue having similar properties, e.g., one $Xaa^H$, e.g., Val, Leu, etc., may be replaced with another $Xaa^H$, e.g., Leu, Ile, Ala, etc., one $Xaa^A$ may be replaced with another $Xaa^A$, one $Xaa^P$ may be replaced with another $Xaa^P$, one $Xaa^N$ may be replaced with another $Xaa^N$, one $Xaa^L$ may be replaced with another $Xaa^L$, etc.

In some embodiments, antibody-binding moieties, e.g., antibody-binding moieties, and useful technologies for developing or assessing these moieties are described in, e.g., Alves, Langmuir, 28, 9640-9648 (2012), Choe et al., Materials, 9 (20), 994 (2016), Gupta et al., Nature Biomedical Engineering, 3, 917-929 (2019), Muguruma et al., ACS Omega, 4, 14390-14397 (2019), Yamada et al., Angewandte Chemie Int., Ed Engl.; 58 (17), 5592-5597 (Apr. 16, 2019), Kruljec et al., Bioconjugate Chem., 28 (8): 2009-2030 (2017), e.g., Fabsorbent, triazines, etc.; Kruljec et al., Bioconjugate Chem., 29 (8), 2763-2775 (2018), International Patent Publication WO 2012/017021, etc., the binding moieties, e.g., antibody-binding moieties of each of which is incorporated in this specification in its entirety by reference.

In some embodiments, an antibody-binding moiety, e.g., a protein-binding moiety, e.g., an antibody-binding moiety), is an affinity substance described in AU 2018259856 or International Patent Publication WO 2018199337, the affinity substance of each of which is incorporated in this specification by reference.

In some embodiments, an antibody-binding moiety comprises an adapter protein agent, e.g., as described by Hui et al., Bioconjugate Chem., 26, 1456-1460 (2015). In some embodiments, when used in accordance with this specification, adapter proteins do not require reactive residues, e.g., BPA, to achieve one or more advantages.

In some embodiments, an antibody-binding moiety, e.g., an antibody-binding moiety, is or comprises a triazine moiety, e.g., one described in US 2009/0286693. In some embodiments, an antibody-binding moiety, e.g., an antibody-binding moiety, is of such a structure that its corresponding compound is a compound described in US 2009/0286693, the compounds of which are independently incorporated in this specification by reference. In some embodiments, an antibody-binding moiety, e.g., an antibody-binding moiety, is ABT. In some embodiments, ABT is of such a structure that H-ABT is a compound described in US 2009/0286693, the compounds of which are independently incorporated in this specification by reference. In some embodiments, this compound can bind to an antibody. In some embodiments, this compound can bind to the Fc region of an antibody.

In some embodiments, an antibody-binding moiety, e.g., an antibody-binding moiety, is or comprises a triazine moiety, e.g., one described in Teng et al., J. Mol. Recognition, 12, 67-75 (1999). In some embodiments, an antibody-binding moiety, e.g., an antibody-binding moiety, is of such a structure that its corresponding compound is a compound described in Teng, the compounds of which are independently incorporated in this specification by reference. In some embodiments, an antibody-binding moiety, e.g., an antibody-binding moiety, is of such a structure that H-ABT is a compound described in Teng, the compounds of which are independently incorporated in this specification by reference. In some embodiments, this compound can bind to an antibody. In some embodiments, this compound can bind to the Fc region of an antibody.

In some embodiments, an antibody-binding moiety, e.g., an antibody-binding moiety, is a triazine moiety, e.g., one described by Uttamchandani et al., J. Comb. Chem., 6 (6), 862-8 (November-December 2004). In some embodiments, an antibody-binding moiety, e.g., an antibody-binding moiety, is of such a structure that its corresponding compound is a compound described in Uttamchandani, the compounds of which are independently incorporated in this specification by reference. In some embodiments, an antibody-binding moiety, e.g., an antibody-binding moiety, is of such a structure that H-ABT is a compound described by Uttamchandani, which is independently incorporated in this specification by reference. In some embodiments, this compound can bind to an antibody. In some embodiments, this compound can bind to the Fc region of an antibody.

In some embodiments, an antibody-binding moiety binds to one or more binding sites of a protein selected from the Markush group of proteins consisting of protein A, protein G, protein L, protein Z, protein LG, protein LA, and protein AG. In some embodiments, an antibody-binding moiety is described in Choe, Durgannavar, & Chung, Materials, 9 (12)(2016).

Other useful technologies are described in Mustafaoglu et al., Analyst, 141 (24), 6571-6582 (Nov. 28, 2016).

Several antibody-binding moieties, including universal antibody-binding moieties, can be used in accordance with the teachings of this specification. Some antibody-binding moieties and technologies for identifying or assessing antibody-binding moieties are described in International Patent Publications WO 2019/023501 and WO 2019/136442, each of which is incorporated in this specification in its entirety by reference. Persons having ordinary skill in the biomedical art know that additional technologies in the biomedical art may be suitable for identifying or assessing antibody-binding moieties in accordance with this specification. In some embodiments, an antibody-binding moiety comprises one or more amino acid residues, each independently natural or unnatural.

Linker Moiety.

In some embodiments, provided compounds and agents may comprise one or more amino acid moieties, e.g., antibody-binding moieties, linker moieties, etc. Amino acid moieties can either be those of natural amino acids or unnatural amino acids. In some embodiments, an amino acid has the structure of the formula LNK101:

$$NH(R^{a1})—L^{a1}—C(R^{a2})(R^{a3})—L^{a2}—COOH,$$

[LNK101] or a salt thereof, wherein:

each of $R^{a1}$, $R^{a2}$, and $R^{a3}$ is independently-$L^a$-R' or an amino acid side chain;

each of $L^{a1}$ and $L^{a2}$ is independently $L^a$;

each $L^a$ is independently a covalent bond, or an optionally substituted bivalent group selected from $C_1$-$C_{20}$ aliphatic or $C_1$-$C_{20}$ heteroaliphatic having 1-5 heteroatoms, wherein one or more methylene units of the group are optionally and independently replaced with —$C(R')_2$—, -Cy-, —O—, —S—, —S—S—, —N(R')—, —C(O)—, —C(S)—, —C(NR')—, —C(O)

$N(R')$—, —$N(R')C(O)N(R')$—, —$N(R')C(O)O$—, —$S(O)$—, —$S(O)_2$—, —$S(O)_2N(R')$—, —$C(O)S$—, or —$C(O)O$—;

each -Cy- is independently an optionally substituted bivalent monocyclic, bicyclic, or polycyclic group wherein each monocyclic ring is independently selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus, and silicon, and a 3-20 membered heterocyclyl ring having 1-10 heteroatoms independently selected from oxygen, nitrogen, sulfur, phosphorus, and silicon;

each R' is independently —R, —C(O)R, —$CO_2R$, or —$SO_2R$;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus, and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus, and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic, or polycyclic ring having, in addition to the atom, 0-10 heteroatoms independently selected from oxygen, nitrogen, sulfur, phosphorus, and silicon; or two or more R groups on two or more atoms are optionally and independently taken together with their intervening atoms to form an optionally substituted, 3-30 membered, monocyclic, bicyclic, or polycyclic ring having, in addition to the intervening atoms, 0-10 heteroatoms independently selected from oxygen, nitrogen, sulfur, phosphorus, and silicon.

In some embodiments, an amino acid residue, e.g., of an amino acid having the structure of formula LNK101, has the structure of —$N(R^{a1})$-$L^{a1}$-$C(R^{a2})(R^{a3})$-$L^{a2}$-CO—. In some embodiments, each amino acid residue in a peptide independently has the structure of —$N(R^{a1})$-$L^{a1}$-$C(R^{a2})(R^{a3})$-$L^{a2}$-CO—.

In some embodiments, the invention provides a derivative of an amino acid of formula LNK101 or a salt thereof. In some embodiments, a derivative is an ester. In some embodiments, the invention provides a composition of matter of formula $NH(R^{a1})$-$L^{a1}$-$C(R^{a2})(R^{a3})$-$L^{a2}$-$COOR^{CT}$ or salt thereof, wherein $R^{CT}$ is R' and each other variable is independently as described in this specification. In some embodiments, $R^{CT}$ is R. In some embodiments, $R^{CT}$ is optionally substituted aliphatic. In some embodiments, $R^{CT}$ is t-butyl.

In some embodiments, $L^{a1}$ is a covalent bond. In some embodiments, a composition of matter of formula LNK101 is of the structure $NH(R^{a1})$—$C(R^{a2})(R^{a3})$-$L^{a2}$-COOH. In some embodiments, $L^{a2}$ is —$CH_2SCH_2$—.

In some embodiments, $L^{a2}$ is a covalent bond. In some embodiments, a composition of matter of formula LNK101 is of the structure $NH(R^{a1})$-$L^{a1}$-$C(R^{a2})(R^{a3})$—COOH. In some embodiments, an amino acid residue has the structure of —$N(R^{a1})$-$L^{a1}$-$C(R^{a2})(R^{a3})$—CO—. In some embodiments, $L^{a1}$ is —$CH_2CH_2S$—. In some embodiments, $L^{a1}$ is —$CH_2CH_2S$—, wherein the $CH_2$ is bonded to $NH(R^{a1})$.

In some embodiments, $L^{a1}$ is a covalent bond, and $L^{a2}$ is a covalent bond. In some embodiments, a composition of matter of formula LNK101 is of the structure $NH(R^{a1})$—$C(R^{a2})(R^{a3})$—COOH. In some embodiments, a composition of matter of formula LNK101 is of the structure $NH(R^{a1})$—$CH(R^{a2})$—COOH. In some embodiments, a composition of matter of formula LNK101 has a structure selected from the Markush group of peptides consisting of $NH(R^{a1})$—$CH(R^{a3})$—COOH, $NH_2$—$CH(R^{a2})$—COOH, $NH_2$—$CH(R^{a3})$—COOH, —$N(R^{a1})$—$C(R^{a2})(R^{a3})$—CO—, —$N(R^{a1})$—$CH(R^{a2})$—CO—, —$N(R^{a1})$—$CH(R^{a3})$—CO—, —NH—$CH(R^{a2})$—CO—, and —NH—$CH(R^{a3})$—CO—.

In some embodiments, $L^a$ is a covalent bond. In some embodiments, $L^a$ is optionally substituted by $C_{1-6}$ bivalent aliphatic. In some embodiments, $L^a$ is optionally substituted for $C_{1-6}$ alkylene. In some embodiments, $L^a$ is —$CH_2$—. In some embodiments, $L^a$ is —$CH_2CH_2$—. In some embodiments, $L^a$ is —$CH_2CH_2CH_2$—.

In some embodiments, $L^a$ is bivalent optionally substituted $C_{1-20}$ aliphatic, wherein one or more methylene units are independently replaced with —C(O)—, —N(R')—, -Cy-, or —O—. In some embodiments, $L^a$ is bivalent optionally substituted $C_{1-20}$ aliphatic, wherein one or more methylene units are independently replaced with —C(O)N(R')—, -Cy-, and —O—. In some embodiments, $L^a$ is bivalent optionally substituted $C_{1-20}$ aliphatic, wherein two or more methylene units are independently replaced with —C(O)N(R')—, and -Cy- in addition to other optional replacements. In some embodiments, -Cy- is optionally substituted. In some embodiments, -Cy- is optionally substituted with an electron-withdrawing group as described in this specification. In some embodiments, -Cy- is substituted with one or more —F. In some embodiments, -Cy- is optionally substituted 1,3-phenylene. In some embodiments, -Cy- is optionally substituted 1,4-phenylene. In some embodiments, $L^a$ is or comprises a chemical group disclosed in International Patent Publication WO 2024/228935 (Biohaven Therapeutics, Ltd.), the contents of which are incorporated herein in their entireties by reference.

MATES

As used herein, the term "MATE" refers to Multimodal Antibody Therapy Enhancer. This next-generation antibody conjugation technology enables site-directed pairing with therapeutic monoclonal antibodies (mAbs), or therapeutic immunoglobulin (IG) pooled from donors. Persons having ordinary skill in the biomedical art can use MATES materials and methods as guidance to predictable results when making and using the invention.

This agent may be referred to as a MATE agent or MATE. The MATE agents are described, for example, in International Patent Publication WO 2021/102052, the content of which is incorporated in this specification in its entirety by reference. In some embodiments, an agent comprises an antibody-binding moiety, a cellular receptor-binding moiety, and a linker moiety linking an antibody-binding moiety and a cellular receptor-binding moiety.

Figure 14:
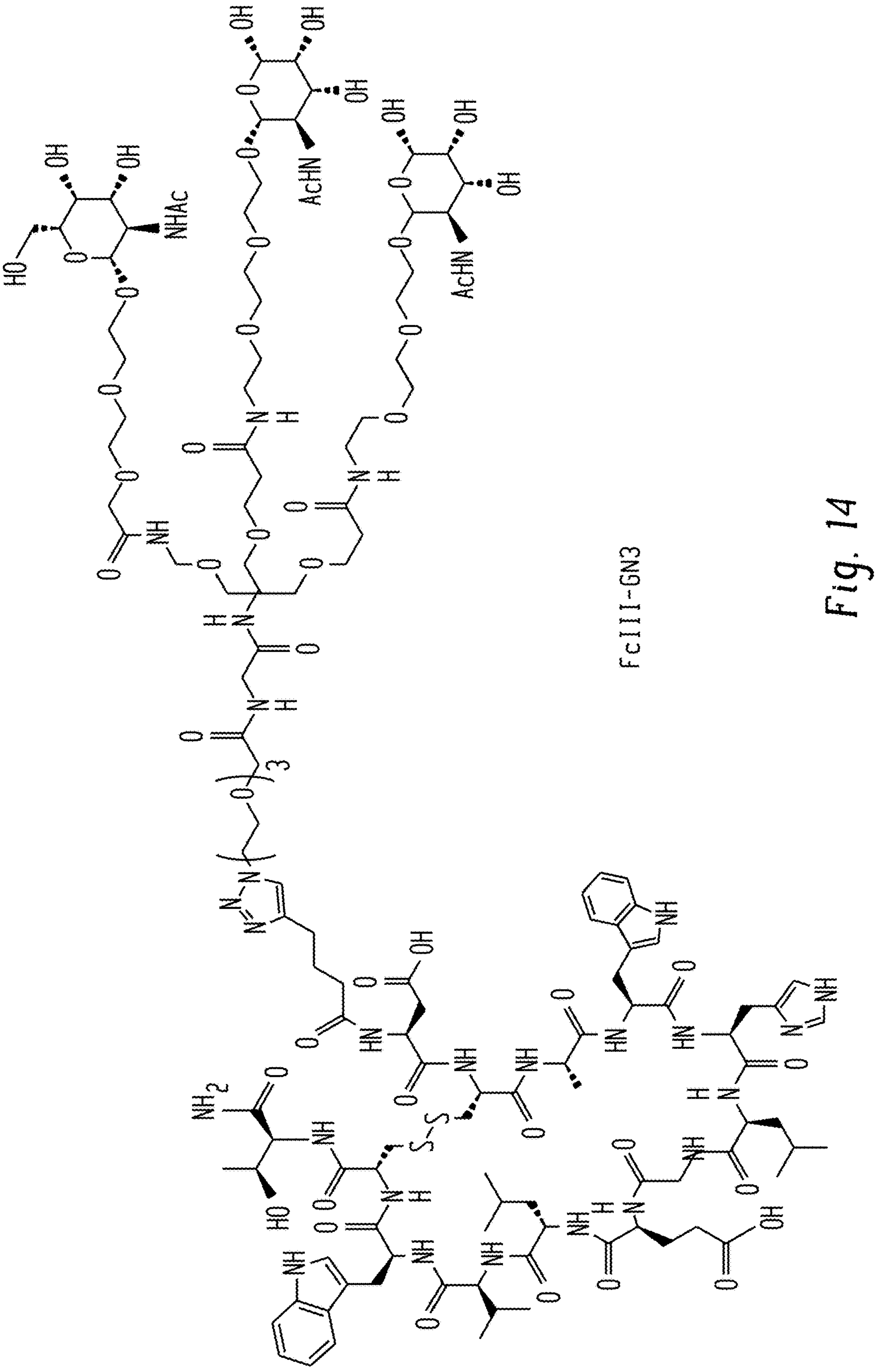
FIG. 14 shows the chemical structure of Compound FcIII-GN3, which is an IgG degrader.

In a specific embodiment, the cellular receptor-binding moiety is TBT301 or a conjugation reaction derivative thereof. See FIG. 14.

Second Agent.

In another embodiment, the invention provides a composition including the agent and at least one additional agent comprising a moiety capable of binding to the protein that forms the antibody-binding moiety of the first compound.

In some embodiments, a first composition comprises a first agent described in this specification. In some embodiments, second agents independently comprise second reactive groups. In some embodiments, a second composition comprises a plurality of agents as described in this specification, wherein each cellular receptor-binding moiety is independently a reactive group as described in this specification. In some embodiments, a second composition is an antibody composition, wherein antibodies in the composition are not chemically modified. In some embodiments, a second composition is an IVIG preparation. In some embodiments, a product composition comprises a plurality of agents as described in this specification, wherein each cellular receptor-binding moiety is independently a cellular receptor-binding moiety as described in this specification.

In some embodiments, a cellular receptor-binding moiety in a product agent is a cellular receptor-binding moiety in a first agent. In some embodiments, an antibody moiety in a product agent is an antibody moiety in a second agent. In some embodiments, a second agent is an antibody agent, e.g., a monoclonal antibody, an antibody in a polyclonal antibody, an antibody in an IVIG preparation, etc. In some embodiments, a second reactive group is a function group of an amino acid residue, e.g., —$NH_2$ of lysine, —SH of cysteine, etc. In some embodiments, a second reactive group is —$NH_2$ of a lysine residue, e.g., of a residue selected from K246 and K248 of IgG1 heavy chain amino acid residues corresponding thereto, K251 and K253 of an IgG2 heavy chain and amino acid residues corresponding thereto, and K239 and K241 of a heavy chain and amino acid residues corresponding thereto. In some embodiments, the invention provides selective reactions at amino acid residues of antibody moieties. In an embodiment, an antibody moiety may be an Fc moiety of an antibody.

In some embodiments, a second reactive group is installed to an antibody moiety optionally through a linker. In some embodiments, a second reactive group is installed to an antibody moiety through a linker. In some embodiments, a second reactive group is selectively linked to certain location(s) of an antibody moiety, e.g., certain location(s) selected from K246 and K248 of IgG1 heavy chain amino acid residues corresponding thereto, K251 and K253 of an IgG2 heavy chain and amino acid residues corresponding thereto, and K239 and K241 of a heavy chain and amino acid residues corresponding thereto. In some embodiments, the invention provides selective reactions at amino acid residues of antibody moieties.

In some embodiments, the invention provides agents, each independently comprising an antibody-binding moiety that binds to an antibody agent, a reactive group, a cellular receptor-binding moiety, and optionally one or more linker moieties linking these groups/moieties. In some embodiments, these agents are useful as reaction partners, e.g., first agents for conjugating moieties of interest, e.g., anti-TSH receptor autoantibody-binding moieties, reactive groups, e.g., second reactive groups to agents comprising antibody moieties, e.g., second agents. In some embodiments, the invention provides agents for conjugating moieties of interest to antibody moieties in several agents or antibody agents, e.g., monoclonal antibody agents, polyclonal antibody agents, antibody agents of IVIG preparations, etc. In some embodiments, provided agents each comprise a cellular receptor-binding moiety, a reactive group, an antibody-binding moiety, and optionally one or more linker moieties (linkers) linking these moieties. In some embodiments, an antibody-binding moiety is part of a leaving group that is released after contacting this agent, e.g., a first agent, with an antibody moiety, e.g., of a second agent, and reacting a reactive group of this agent, e.g., a first reactive group of a first agent, with a reactive group of an antibody moiety, e.g., a second reactive group of a second agent, such as —$NH_2$ of a Lys residue of an antibody protein. In some embodiments, provided technologies can provide improved conjugation efficiency, high selectivity, or fewer steps (in some cases, single steps) to conjugation product agents.

In some embodiments, anti-TSH receptor autoantibody-binding moieties may be conjugated to antibody moieties optionally through linker moieties using technologies described in Patent Publication US 2020/0190165.

In some embodiments, where a particular protecting group (PG), leaving group (LG), or transformation condition is depicted, persons having ordinary skill in the biomedical art know that other protecting groups, leaving groups, and transformation conditions are also suitable and are contemplated. These groups and transformations are described in Greene's Protecting Groups in Organic Synthesis, Wuts editor (John Wiley & Sons, 2014), the entirety of each of which is incorporated in this specification by reference.

In some embodiments, an oxygen-protecting group includes carbonyl and hydroxyl-protecting groups, etc. Hydroxyl-protecting groups and amino-protecting groups are well known in the biomedical art and include those described in Greene's Protecting Groups in Organic Synthesis, Wuts, editor (John Wiley & Sons, 2014), the entirety of which is incorporated in this specification by reference.

Persons having ordinary skill in the biomedical art know that provided agents may contain one or more stereocenters and may be present as a racemic or diastereomeric mixture. They know that there are many methods known in the biomedical art for the separation of isomers to obtain stereoenriched or stereopure isomers of those compounds, including but not limited to high performance liquid chromatography, chiral high performance liquid chromatography, fractional crystallization of diastereomeric salts, kinetic enzymatic resolution, e.g., by fungal-derived, bacterial-derived, or animal-derived lipases or esterases), and formation of covalent diastereomeric derivatives using an enantioenriched reagent.

Persons having ordinary skill in the biomedical art know that several functional groups present in compounds of this specification, such as aliphatic groups, alcohols, carboxylic acids, esters, amides, aldehydes, halogens, and nitriles, can be interconverted by techniques well known in the biomedical art including, but not limited to reduction, oxidation, esterification, hydrolysis, partial oxidation, partial reduction, halogenation, dehydration, partial hydration, and hydration. See Smith & March, March's Advanced Organic Chemistry: Reactions, Mechanisms, and Structure, $5^{th}$ edition (John Wiley & Sons, 2001), which is incorporated in this specification by reference.

As known by persons having ordinary skill in the biomedical art, reaction partners are generally contacted with each other under conditions and for a time sufficient for producing the desired results, e.g., formation of product agents and compositions thereof to desired extents. Many reaction conditions/reaction times may be assessed and used if they are suitable for desired purposes in accordance with this specification.

In some embodiments, the invention provides products of provided processes, which have low levels of damage to antibody moieties compared to processes comprising steps performed for antibody-binding moiety removal but not for substantial conjugation of moieties of interest, e.g., anti-TSH receptor autoantibody-binding moieties. In some embodiments, provided product agent compositions have high homogeneity, e.g., regarding the number of cellular receptor-binding moiety per antibody moiety or positions of amino acid residues in antibody moieties conjugated to moieties of interest) compared to reference product compositions, e.g., those from technologies without using antibody-binding moieties or using extra step(s) for antibody-binding moiety removal, e.g., not using reaction partners described in this specification which comprise a reactive group located between an antibody-binding moiety and a cellular receptor-binding moiety.

In some embodiments, the invention provides a product agent, which is an agent comprising an antibody moiety, a cellular receptor-binding moiety, and optionally a linker moiety linking an antibody-binding moiety and a cellular receptor-binding moiety. In some embodiments, the invention provides compositions of such agents.

Plurality of Agents.

In some embodiments, the invention provides a composition comprising a plurality of agents, wherein each agent independently comprises:

an antibody moiety, a cellular receptor-binding moiety, and optionally a linker moiety linking an antibody-binding moiety and a cellular receptor-binding moiety.

In some embodiments, product agents are MATE agents. In some embodiments, an antibody agent moiety comprises the IgG Fc region. In some embodiments, an antibody moiety is connected to a cellular receptor-binding moiety through an amino group, optionally through a linker. In some embodiments, it is through a lysine residue wherein the amino group of the side chain is connected to a cellular receptor-binding moiety optionally through a linker, e.g., forming —NH—C(O)— as part of an amide group, a carbamate group, etc.

In some embodiments, selected locations of antibody moieties are used for conjugation. In some embodiments, K246 or K248 of an antibody agent (EU numbering or corresponding residues) are conjugation locations. In some embodiments, a conjugation location is K246 of the heavy chain (unless otherwise specified, locations in this specification include corresponding residues in, e.g., modified sequence, e.g., longer, shorter, rearranged, etc., sequences. In some embodiments, a location is K248 of the heavy chain. In some embodiments, a location is K288 or K290 of heavy chain. In some embodiments, a location is K288 of the heavy chain. In some embodiments, a location is K290 of heavy chain. In some embodiments, a location is K317. In some embodiments, an antibody moiety is a moiety of an IgG1 antibody or a fragment thereof. In some embodiments, an antibody moiety is a moiety of an IgG2 antibody or a fragment thereof. In some embodiments, an antibody moiety is a moiety of an antibody or a fragment thereof. In some embodiments, a composition comprises a plurality of MATE agents, wherein antibody moieties of the plurality of MATE agents are independently an antibody moiety of an IgG1, IgG2, or IgG4 antibody, or a fragment thereof.

In some embodiments, antibody heavy chains are selectively conjugated/labeled over light chains.

In some embodiments, the invention provides a composition comprising a plurality of agents, each of which independently comprises:

an antibody moiety, a cellular receptor-binding moiety, and optionally a linker moiety linking the antibody moiety and the cellular receptor-binding moiety; wherein antibody moieties of agents of the plurality comprise a common amino acid sequence, and agents of the plurality share a common cellular receptor-binding moiety independently of at least one common amino acid residue of the common amino acid sequence; and wherein about 1%-100% of all agents that comprise an antibody moiety that comprises the common amino acid sequence and the cellular receptor-binding moiety are agents of the plurality.

In some embodiments, the invention provides a composition comprising a plurality of agents, each of which independently comprises:

an antibody moiety, a cellular receptor-binding moiety, and optionally a linker moiety linking an antibody moiety and a cellular receptor-binding moiety; wherein agents of the plurality share the same or substantially the same antibody moiety and a cellular receptor-binding moiety at least one common location; and wherein about 1%-100% of all agents that comprise the antibody moiety and the cellular receptor-binding moiety are agents of the plurality.

Reactive Group

In some embodiments, provided agents, compounds, e.g., those useful as reaction partners such as first agents, comprise reactive groups, e.g., RG. In some embodiments, reactive groups are located between antibody-binding moieties and moieties of interest. Reactive groups are optionally and independently linked to antibody-binding moieties and moieties of interest via linkers. In some embodiments, RG is a reaction group, as described in this specification.

In some embodiments, reactive groups, when used in agents that comprise no antibody-binding moieties, react slowly and provide a low level of, in some embodiments, substantially no conjugation of moieties of interest with target agents. As shown in this specification, a combination of reactive groups with antibody-binding moieties in the same agents, can promote reactions between reactive groups and target agents, enhance reaction efficiency, reduce side reactions, or improve reaction selectivity, e.g., in terms of target sites wherein conjugation of moieties of interest with target agents occurs.

Reactive groups in agents can react with several groups in target agents. In some embodiments, reactive groups in agents selectively react with amino groups of target agents, e.g., $—NH_2$ groups on side chains of lysine residues of proteins. In some embodiments, reactive groups when used in agents, selectively react with sites of target agents, e.g., as shown in examples in this specification, one or more of K246, K248, K288, K290, K317, etc. for IgG1, one or more of K251, K253, etc. for IgG2, and one or more of K239, K241 for IgG4. In some embodiments, a site is K246 or K248 of an antibody heavy chain. In some embodiments, sites are K246 or K248 of an antibody heavy chain. In some embodiments, a site is K246 of an antibody heavy chain. In some embodiments, a site is K248 of an antibody heavy chain. In some embodiments, a site is K288 or K290 of an antibody heavy chain. In some embodiments, a site is K288 of an antibody heavy chain. In some embodiments, a site is K290 of an antibody heavy chain. In some embodiments, a site is K317. In some embodiments, a site is K414 of an antibody heavy chain. In some embodiments, a site is K185 of an antibody light chain. In some embodiments, a site is K187 of an antibody light chain. In some embodiments, sites are K251 or K253 of an IgG2 heavy chain. In some embodiments, a site is K251 of an IgG2 heavy chain. In some embodiments, a site is K253 of an IgG2 heavy chain. In some embodiments, sites are K239 or K241 of an antibody heavy chain. In some embodiments, a site is K239 of an antibody heavy chain. In some embodiments, a site is K241 of an antibody heavy chain. In some embodiments, conjugation selectively occurs at one or more heavy chain sites over light chain sites. In some embodiments, for technologies without antibody-binding moieties, conjugation occurs at light chain sites more than heavy chain sites.

In some embodiments, a reactive group, e.g., RG, is or comprises an ester group. In some embodiments, a reactive group, e.g., RG, is or comprises an electrophilic group, e.g., a Michael acceptor.

In some embodiments, a reactive group, e.g., RG, is or comprises -$L^{RG1}$-$L^{RG2}$-, wherein each of $L^{RG1}$ and $L^{RG2}$ is independently L. In some embodiments, a reactive group, e.g., RG, is or comprises -$L^{G4}$-$L^{RG1}$-$L^{RG2}$-, wherein each variable is as described in this specification. In some embodiments, a reactive group, e.g., RG, is or comprises -$L^{LG3}$-$L^{LG4}$-$L^{RG1}$-$L^{RG2}$-, wherein each variable is as described in this specification. In some embodiments, a reactive group, e.g., RG, is or comprises -$L^{LG2}$-$L^{LG3}$-$L^{LG4}L^{RG1}$-$L^{RG2}$-, wherein each variable is as described in this specification. In some embodiments, a reactive group, e.g., RG, is or comprises -$L^{LG4}$-$L^{RG2}$-, wherein each variable is as described in this specification. In some embodiments, a reactive group, e.g., RG, is or comprises -$L^{LG3}$-$L^{LG4}$-$L^{RG2}$-, wherein each variable is as described in this specification. In some embodiments, a reactive group, e.g., RG, is or comprises -$L^{LG2}$-$L^{LG3}$-$L^{LG4}$-$L^{RG2}$-, wherein each variable is as described in this specification.

In some embodiments, $L^{LG4}$ is —O—. In some embodiments, $L^{LG4}$ is —N(R)—. In some embodiments, L'G4 is —NH—.

In some embodiments, $L^{LG3}$ is or comprises an optionally substituted aryl ring. In some embodiments, $L^{LG3}$ is or comprises a phenyl ring. In some embodiments, an aryl or phenyl ring is substituted. In some embodiments, a substituent is an electron-withdrawing group as described in this specification, e.g., —$NO_2$, —F, etc.

In some embodiments, $L^{RG1}$ is a covalent bond. In some embodiments, $L^{RG1}$ is not a covalent bond. In some embodiments, $L^{RG1}$ is —$S(O)_2$—.

In some embodiments, $L^{RG2}$ is —C(O)—. In some embodiments, a reactive group comprises $L^{LG4}$-C(O), wherein each variable is described in this specification. In some embodiments, a reactive group comprises -$L^{LG3}$-$L^{LG4}$-C(O)—, wherein each variable is as described in this specification. In some embodiments, a reactive group comprises -$L^{LG2}$-$L^{LG3}$-$L^{LG4}$-C(O)—, wherein each variable is as described in this specification.

In some embodiments, $L^{RG2}$ is -$L^{RG3}$-C(═$CR^{RG1}R^{RG2}$)—$CR^{RG3}R^{RG4}$—, wherein each of $R^{RG1}$, $R^{RG2}$, $R^{RG3}$ and $R^{RG4}$ is independently -L-R', and $L^{RG3}$ is —C(O)—, —C(O)O—, —C(O)N(R')—, —S(O)—, —$S(O)_2$—, —P(O)(OR')—, —P(O)(SR')—, or —P(O)(N$(R')_2$)—. In some embodiments, each of $R^{RG1}$, $R^{RG2}$, $R^{RG3}$, and $R^{RG4}$ is independently R'. In some embodiments, one or more of $R^{RG1}$, $R^{RG2}$, $R^{RG3}$ and $R^{RG4}$ is independently —H. In some embodiments, $L^{RG3}$ is —C(O)—. In some embodiments, $L^{RG3}$ is —C(O)O—. In some embodiments, —O—, —N(R')—, etc. of $L^{RG3}$ is bonded to LPM.

In some embodiments, $R^{RG1}$ is —H. In some embodiments, $R^{RG3}$ is —H.

In some embodiments, $L^{RG2}$ is optionally substituted -$L^{RG3}$-C(═$CHR^{RG2}$)—$CHR^{RG4}$—, wherein each variable is as described in this specification.

In some embodiments, $R^{RG2}$ and $R^{RG4}$ are taken together with their intervening atoms to form an optionally substituted ring as described in this specification. In some embodiments, a formed ring is an optionally substituted 3-10 membered monocyclic or bicyclic ring having 0-5 heteroatoms. In some embodiments, a formed ring is an optionally substituted 3-10-membered cycloaliphatic ring. In some embodiments, a formed ring is selected from the Markush group consisting of optionally substituted cycloaliphatic rings consisting of a 3-8 membered cycloaliphatic ring, a 5-8 membered cycloaliphatic ring., a 5-membered cycloaliphatic ring, a 6-membered cycloaliphatic ring, and a 7-membered cycloaliphatic ring. In some embodiments, a formed ring is substituted. In some embodiments, a formed ring is not substituted. In some embodiments, a formed ring contains no additional unsaturation besides the double bond in C(═$CHR^{RG2}$) or C(═$CR^{RG1}R^{RG2}$).

In some embodiments, —C(═$CHR^{RG2}$)—$CHR^{RG4}$ or —C(═$CR^{RG1}R^{RG2}$)—$CR^{RG3}R^{RG4}$ is optionally substituted

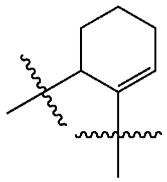 or is 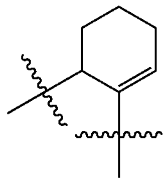 .

In some embodiments, —[C(═$CHR^{RG2}$)—$CHR^{RG4}$]-$L^{RG3}$- or —[C(═$CR^{RG1}R^{RG2}$)—$CR^{RG3}R^{RG4}$]-$L^{RG3}$- is optionally substituted

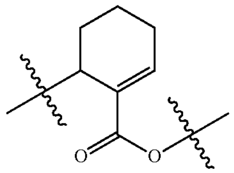 or is 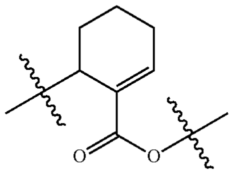 .

In some embodiments, -$L^{RG1}$-[C(═$CHR^{RG2}$)—$CHR^{RG4}$]-$L^{RG3}$- or -$L^{RG1}$-[C(═$CR^{RG1}R^{RG2}$)—$CR^{RG3}R^{RG4}$]-$L^{RG3}$- is optionally substituted

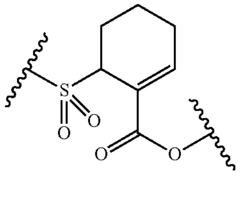 .

In some embodiments, -$L^{RG1}$-[C(═$CHR^{RG2}$)—$CHR^{RG4}$]-$L^{RG3}$- or -$L^{RG1}$-[C(═$CR^{RG1}R^{RG2}$)—$CR^{RG3}R^{RG4}$]-$L^{RG3}$- is optionally substituted.

In some embodiments, a reactive group, e.g., -$L^{LG2}$-$L^{LG3}$-$L^{LG4}$-$L^{RG1}$-$L^{RG2}$- or -$L^{LG2}$-$L^{LG3}$-$L^{LG4}$-$L^{RG1}$-, is a structure selected from TABLE 3 of International Patent Publication WO 2024/228935 (Biohaven Therapeutics, Ltd.).

In some embodiments, -$L^{G4}$-$L^{RG2}$- is —O—C(O)— or —S—C(O)—. In some embodiments, -$L^{LG4}$-$L^{RG1}$-$L^{RG2}$- is —S—C(O)—.

In some embodiments, -$L^{LG4}$-$L^{RG2}$- is —N(−)—C(O)—, wherein N is a ring atom of an optionally substituted heteroaryl ring. In some embodiments, -$L^{LG4}$-$L^{RG2}$- is —N(−)—C(O)—, wherein N is a ring atom of $L^{LG4}$, which is or comprises an optionally substituted heteroaryl ring. In some embodiments, -$L^{LG4}$-$L^{RG2}$- is —N(−)—C(O)—O—, wherein N is a ring atom of $L^{LG4}$, which is or comprises an optionally substituted heteroaryl ring.

In some embodiments, $L^{RG2}$ is optionally substituted —$CH_2$—C(O)—, wherein —$CH_2$— is bonded to an electron-withdrawing group comprising or connected to an antibody-binding moiety. In some embodiments, $L^{RG2}$ is optionally substituted —$CH_2$— bonded to an electron-withdrawing group comprising or connected to an antibody-binding moiety. In some embodiments, $L^{RG1}$ is an electron-withdrawing group. In some embodiments, $L^{RG1}$ is selected from the Markush group consisting of —C(O)—, —S(O)—, —$S(O)_2$—, —P(O(OR)—, —P(O(SR)—, —P(O(N(R)$_2$)—, —OP(O(OR)—, —OP(O(SR)—, and —OP(O(N(R)$_2$)—.

In some embodiments, $L^{RG2}$ is optionally substituted —$CH_2$—C(O)—, wherein —$CH_2$— is bonded to a leaving group comprising or connected to an antibody-binding moiety. In some embodiments, $L^{RG2}$ is optionally substituted —$CH_2$— bonded to a leaving group comprising or connected to an antibody-binding moiety. In some embodiments, $L^{RG1}$ is selected from the Markush group consisting of —O—C(O)—, —$OS(O)_2$—, —OP(O(OR)—, —OP(O(SR)—, and —OP(O(N(R)$_2$)—.

In some embodiments, a reactive group reacts with an amino group of a target agent. In some embodiments, an amino group is —$NH_2$ of the side chain of a lysine residue.

In some embodiments, a target agent is a protein agent. In some embodiments, a target agent is an antibody agent. In some embodiments, a reactive group reacts with an amino acid residue of this protein or antibody agent. In some embodiments, an amino acid residue is a lysine residue. In some embodiments, a reactive group reacts with —$NH_2$ of the side chain of a lysine residue. In some embodiments, a reactive group is or comprises —C(O)—O— reacts with —$NH_2$, e.g., of the side chain of a lysine residue) and forms an amide group —C(O)—O— with the —$NH_2$.

In some embodiments, reactive groups, e.g., a first reactive group, a second reactive group, etc., are located at terminal locations. In some embodiments, the first agents comprise the first reactive groups linked to anti-TSH receptor autoantibody-binding moieties optionally through linker moieties, and they do not contain antibody-binding moieties.

In some embodiments, the invention provides methods for preparing a composition comprising a plurality of agents, wherein each agent independently comprises:

- an antibody moiety,
- a cellular receptor-binding moiety, and
- optionally a linker moiety linking an antibody moiety and a cellular receptor-binding moiety;

which method comprises:

- contacting a plurality of agents, each independently comprising a reactive group with a plurality of antibody agents.

In some embodiments, an agent comprising a reactive group comprises an antibody-binding moiety, a cellular receptor-binding moiety, and optionally a linker. In some embodiments, agents comprising a reactive group share the same cellular receptor-binding moiety. In some embodiments, agents comprising a reactive group share the same structure. In some embodiments, antibody molecules are of such structures, properties, or activities to provide antibody moieties in agents described in this specification. In some embodiments, a plurality of antibody molecules comprises two or more IgG subclasses. In some embodiments, a plurality of antibody molecules comprises IgG1. In some embodiments, a plurality of antibody molecules comprises IgG2. In some embodiments, a plurality of antibody molecules comprises IgG4. In some embodiments, a plurality of antibody molecules comprises IgG1 and IgG2. In some embodiments, a plurality of antibody molecules comprises IgG1, IgG2, and IgG4. In some embodiments, a plurality of antibody molecules comprises IgG1, IgG2, IgG3 and IgG4. In some embodiments, a plurality of antibody molecules is IVIG antibody molecules.

In some embodiments, provided agents comprise a reactive group, e.g.,

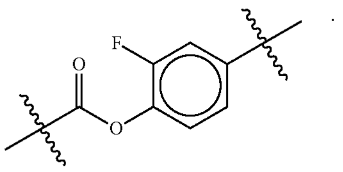

In some embodiments, —C(O)— is connected to a cellular receptor-binding moiety or a moiety comprising -(Xaa)y-, optionally through a linker, and the other end is connected to an antibody-binding moiety. In some embodiments,

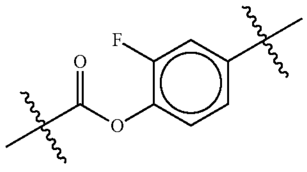

reacts with an amino group of another moiety, e.g., an antibody moiety, forming an amide group with the moiety and releasing a moiety comprising an antibody-binding moiety. In some embodiments, an amino group is —$NH_2$ of a lysine side chain. In some embodiments, —C(O)— is connected to a cellular receptor-binding moiety or a moiety comprising -(Xaa)y-, optionally through a linker, and the other end is connected to R' or an optional substituent. In some embodiments, provided agents comprise optionally substituted

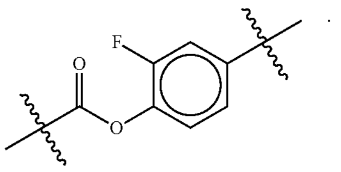

Such reactive groups may be useful for conjugation with detection, diagnosis, or therapeutic agents. Persons having ordinary skill in the biomedical art know that many agents and technologies, e.g., click chemistry, reactions based on functional groups such as amino groups, e.g., amide formation), hydroxyl groups, carboxyl groups, etc. can be used for conjugation in accordance with this specification.

In some embodiments, antibody-binding moieties bind to Fc regions of antibodies. In some embodiments, reactions occur at residues at Fc regions. In some embodiments, anti-TSH receptor autoantibody-binding moieties are conjugated to residues of Fc regions, optionally through linker moieties. In some embodiments, a residue is a Lys residue. In some embodiments, an antibody is or comprises IgG1. In some embodiments, an antibody is or comprises IgG2. In some embodiments, an antibody is or comprises IgG4. In some embodiments, an antibody composition used in a method comprises IgG1 and IgG2. In some embodiments, an antibody composition used in a method comprises IgG1, IgG2, and IgG4. In some embodiments, an antibody composition used in a method comprises IgG1, IgG2, IgG3, and IgG4.

In some embodiments, a product is or comprises IgG1. In some embodiments, a product is or comprises IgG2. In some embodiments, a product is or comprises IgG4. In some embodiments, a product composition comprises IgG1 and IgG2. In some embodiments, a product composition comprises IgG1, IgG2, and IgG4. In some embodiments, a product composition comprises IgG1, IgG2, IgG3, and IgG4.

In some embodiments, provided agents comprising antibody moieties provide one or more or substantially all antibody immune activities, e.g., recruiting one or more types of immune cells or providing short-term and long-term immune activities. In some embodiments, provided agents comprising antibody moieties do not significantly reduce one or more or substantially all relevant antibody immune activities. In some embodiments, provided agents comprising antibody moieties improve one or more or substantially all relevant antibody immune activities, e.g., compared to antibody moieties by themselves. In some embodiments, provided agents provide comparable or better stability than antibody moieties by themselves, e.g., residence time in blood. In some embodiments, antibody moieties in provided agents can bind to the FcRγ of immune cells, e.g., several FcRγ of immune effector cells for desired immune activities, typically at comparable or better levels. In some embodiments, antibody moieties in provided agents have comparable Fab/antigen binding capabilities. In some embodiments, antibody moieties in provided agents have comparable Fab/antigen binding capabilities. In some embodiments, antibody moieties in provided agents provide FcRn binding. In some embodiments, antibody moieties in provided agents provide FcRn binding, e.g., for antibody recycling or prolonged half-life. In some embodiments, provided technologies are useful for modifying blood-derived IgG products as provided technologies are suitable for and can use all IgG subclasses.

In some embodiments, a provided method comprises one of the steps described below. In some embodiments,

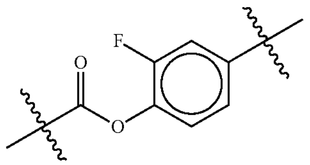

reacts with an amino group of a lysine side chain to form an amide bond with an antibody molecule and release it.

Linker Moieties

In some embodiments, moieties are optionally connected through linker moieties. In some embodiments, a reactive group, e.g., RG, is connected to a cellular receptor-binding moiety, e.g., TBT, through a linker, e.g., $L^{RM}$. In some embodiments, a moiety, e.g., LG, may also comprise one or more linkers, e.g., $L^{LG1}$, $L^{LG2}$, $L^{LG3}$, $L^{LG4}$, etc., to link several portions. In some embodiments, $L^{LG}$ is a linker moiety described in this specification. In some embodiments, $L^{LG1}$ is a linker moiety described in this specification. In some embodiments, $L^{LG2}$ is a linker moiety described in this specification. In some embodiments, $L^{LG3}$ is a linker moiety described in this specification. In some embodiments, $L^{LG4}$ is a linker moiety described in this specification. In some embodiments, $L^{RM}$ is a linker moiety described in this specification. In some embodiments, $L^{PM}$ is L. In some embodiments, $L^{PM}$ is a linker moiety described in this specification. In some embodiments, $L^{PM}$ is L.

Linker moieties of several types or for several purposes, e.g., those used in antibody-drug conjugates, etc., may be used in accordance with this specification.

Linker moieties can be bivalent or polyvalent, depending on how they are used. In some embodiments, a linker moiety is bivalent. In some embodiments, a polyvalent linker connects more than two moieties.

In some embodiments, a linker moiety, e.g., $L^z$, e.g., $L^{PM}$, $L^{RM}$, $L^{LG}$, $L^{LG1}$, etc., is or comprises L.

In some embodiments, L is a covalent bond, or a bivalent or polyvalent optionally substituted, linear or branched $C_{1-100}$ group comprising one or more aliphatic, aryl, heteroaliphatic having 1-20 heteroatoms, heteroaromatic having 1-20 heteroatoms, or any combinations thereof, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue, or —[(—O—C(R')$_2$—C(R')$_2$—)$_n$]—, wherein n is 1-20. The linker optionally contains a cyclic group, Cy, defined below, and a reactive group, RG, as defined below. In some embodiments, each amino acid residue is independently a residue of an amino acid having the structure of formula LNK101 or a salt thereof. In some embodiments, each amino acid residue independently has the structure of —N($R^{a1}$)-$L^{a1}$-C($R^{a2}$)($R^{a3}$)-$L^{a2}$-CO— or a salt form thereof.

In some embodiments, L is bivalent. In some embodiments, L is a covalent bond.

In some embodiments, L is a bivalent or optionally substituted linear or branched group, selected from $C_1$-$C_0$ aliphatic and $C_{1-100}$ heteroaliphatic having 1-50 heteroatoms, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue or —[(—O—C(R')$_2$—C(R')$_2$—)$_n$]—. In some embodiments, L is a bivalent or optionally substituted linear or branched group selected from $C_{1-20}$ aliphatic and $C_{1-20}$ heteroaliphatic having 1-10 heteroatoms, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue or —[(—O—C(R')$_2$—C(R')$_2$—)$_n$]—. In some embodiments, L is a bivalent or optionally substituted linear or branched group selected from $C_{1-20}$ aliphatic, wherein one or more methylene units of the group are optionally and independently replaced with —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, an amino acid residue or —[(—O—C(R')$_2$—C(R')$_2$—)$_n$]—. In some embodiments, L is a bivalent or optionally substituted, linear or branched $C_{1-20}$ aliphatic wherein one or more methylene units of the group are optionally and independently replaced with —C≡C—, -Cy-, —C(R')$_2$—, —O—, —S—, —S—S—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, an amino acid residue or —[(—O—C(R')$_2$—C(R')$_2$—)$_n$]—. In some embodiments, L is a bivalent or optionally substituted linear or branched group $C_{1-100}$ aliphatic, wherein one or more methylene units of the group are optionally and independently replaced with —C≡C—, -Cy-, —C(R')$_2$—, —O—, —N(R')—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, an amino acid residue or —[(—O—C(R')$_2$—C(R')$_2$—)$_n$]—. In some embodiments, L is a bivalent or optionally substituted linear or branched group $C_{1-50}$ aliphatic, wherein one or more methylene units of the group are optionally and independently replaced as described in this specification. In some embodiments, L is a bivalent or optionally substituted, linear, or branched group $C_{1-40}$ aliphatic, wherein one or more methylene units of the group are optionally and independently replaced as described in this specification. In some embodiments, L is a bivalent or optionally substituted, linear, or branched group $C_{1-20}$ aliphatic, wherein one or more methylene units of the group are optionally and independently replaced as described in this specification. In some embodiments, L is a bivalent or optionally substituted linear or branched group $C_{1-10}$ aliphatic, wherein one or more methylene units of the group are optionally and independently replaced as described in this specification. In some embodiments, L is a bivalent or optionally substituted linear or branched group $C_{1-100}$ alkylene, wherein one or more methylene units of the group are optionally and independently replaced as described in this specification. In some embodiments, L is a bivalent or optionally substituted linear or branched group $C_{1-50}$ alkylene, wherein one or more methylene units of the group are optionally and independently replaced as described in this specification. In some embodiments, L is a bivalent or optionally substituted linear or branched group $C_{1-40}$ alkylene, wherein one or more methylene units of the group are optionally and independently replaced as described in this specification. In some embodiments, L is a bivalent or optionally substituted linear or branched group $C_{1-20}$ alkylene, wherein one or more methylene units of the group are optionally and independently replaced as described in this specification. In some embodiments, L is a bivalent or optionally substituted linear or branched group $C_{1-10}$ alkylene, wherein one or more methylene units of the group are optionally and independently replaced as described in this specification.

In some embodiments, a linker moiety, e.g., L, $L^{PM}$, $L^{RM}$, etc., comprises an acidic group, e.g., —S(O)$_2$OH.

In some embodiments, L is or comprises —[(—O—C(R')$_2$—C(R')$_2$—)$_n$]—. In some embodiments, L is or comprises —[(—O—CH$_2$—CH$_2$—)$_n$]—. In some embodiments, L is —[(—CH$_2$—CH$_2$—O)$_6$]—CH$_2$—CH$_2$—. In some embodiments, L is —[(—CH$_2$—CH$_2$—O)$_8$]—CH$_2$—CH$_2$—. In some embodiments, —CH$_2$—CH$_2$—O— is bonded to an antibody-binding moiety at a —CH$_2$—. In some embodiments, —CH$_2$—CH$_2$—O— is bonded to a cellular receptor-binding moiety at a —CH$_2$—. In some embodiments, $L^{PM}$ is such L. In some embodiments, $L^{RM}$ is such L.

In some embodiments, a linker moiety comprises one or more —(CH$_2$)n-O—, wherein each n is independently 1-20. In some embodiments, it is or comprises one or more —[(CH$_2$)n-O]m-, wherein each n is independently 1-20, and m is 1-100. In some embodiments, it comprises two or more —[(CH$_2$)n-O]m-, wherein each n is independently 1-20, and each m is 1-100. In some embodiments, it is or comprises one or more —(O)C—[(CH$_2$)nO]m(CH$_2$)nNH—, —[(CH$_2$)nO]mNHC(O)[(CH$_2$)nO]mNH—, —[(CH$_2$)nO]m{NHC(O)[(CH$_2$)nO]m}pNH— wherein each n is independently 1-20, and each m is independently 1-100, and where each p is independently 1 to 10. In some embodiments, n is selected from the Markush group of numbers consisting of 1-10, 1-5, and 2. In some embodiments, m is 1-50. In some embodiments, m is 1-40. In some embodiments, m is selected from the Markush group of numbers consisting of 1-30, 1-20, 1-10, 1, 2, 3, 4, 5, 6, 7, 8, 9, 10, 11, 12, 13, 14, 15, 16, 17, 18, 19, and 20.

In some embodiments, a linker moiety, or L, is or comprises —(CH$_2$CH$_2$O)n-, wherein each —CH$_2$— is independently and optionally substituted, and n is 1-20. In some embodiments, a linker moiety, or L, is or comprises —(CH$_2$)n-O—(CH$_2$CH$_2$O)n-(CH$_2$)n-, wherein each n is independently 1-10, and each —CH$_2$— is independently and optionally substituted.

In some embodiments, a linker moiety is trivalent or polyvalent. In some embodiments, a linker moiety is L, where L is trivalent or polyvalent. In some embodiments, L is trivalent. In some embodiments, L is —CH$_2$—N(—CH$_2$—)—C(O)—.

In some embodiments, a linker moiety, e.g., L, comprises one or more amino acid residues or analogues.

In some embodiments, a linker moiety, e.g., L, $L^{RM}$, etc., is or comprises a reactive group as described in this specification. In some embodiments, an agent comprises an antibody-binding moiety and a cellular receptor-binding moiety linked through a linker comprising a reactive group. In some embodiments, a reactive group can react with a lysine residue of an antibody in an aqueous buffer. In some embodiments, a reactive group comprises —C(O)—O—. In some embodiments, a reactive group comprises —C(O)—O—, wherein —O— is bonded to an optionally substituted aryl group. In some embodiments, a reactive group comprises —C(O)—O—, wherein —O— is bonded to an aryl group substituted with one or more electron-withdrawing groups. In some embodiments, one or more of each electron-withdrawing group is independently selected from —$NO_2$ and —F. In some embodiments, an aryl group has the structure of

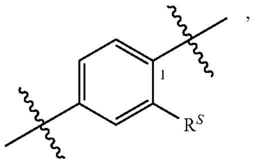

wherein $R^s$ is halogen, —$NO_2$, —F, -L-R', —C(O)-L-R', —S(O)-L-R', —$S(O)_2$-L-R', or —P(O)$(\text{-L-R}')_2$. In some embodiments, an aryl group has the structure of

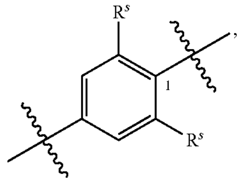

wherein each $R^s$ is independently halogen, —$NO_2$, —F, -L-R', —C(O)-L-R', —S(O)-L-R', —$S(O)_2$-L-R', or —P(O)$(\text{-L-R}')_2$. In some embodiments, an aryl group is

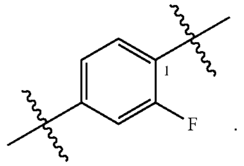 [SMILES: *c1ccc(*)c(F)c1]

In some embodiments, an aryl group is

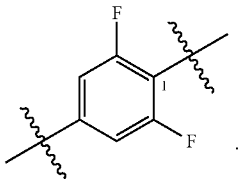 [SMILES: *c1cc(F)c(*)c(F)c1]

In some embodiments, C1 is bound to the —O— of —C(O)—O—. In some embodiments, a cellular receptor-binding moiety is at the side of —C(O)— and an antibody-binding moiety is at the side of —O—.

In some embodiments, a linker moiety, e.g., $L^{RM}$, comprises a reactive group, wherein upon contact with an antibody, the reactive group reacts with a group of the antibody and conjugates a cellular receptor-binding moiety, or a moiety comprising -(Xaa)y-, to the antibody optionally through a linker. In some embodiments, a reactive group is or comprises

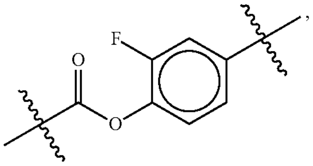

wherein the —C(O)— is connected to a cellular receptor-binding moiety or a moiety comprising -(Xaa)y-, optionally through a linker. In some embodiments, a reactive group is or comprises

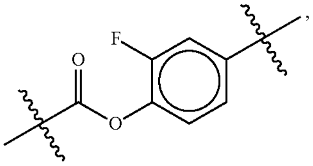

wherein the —C(O)— is connected to a cellular receptor-binding moiety, or a moiety comprising -(Xaa)y-, optionally through a linker and the other end of the reactive group is connected to an antibody-binding moiety.

In some embodiments, a linker moiety, e.g., L) is or comprises one or more, e.g., 1, 2, 3, 4, 5, 6, 7, 8, 9, 10, 11, 12, 13, 14, 15, 16, 17, 18, 19, 20 or more) polyethylene glycol units. In some embodiments, a linker moiety comprises —$(CH_2CH_2O)_n$—, wherein n is described in this specification. In some embodiments, one or more methylene units of L are independently replaced with —$(CH_2CH_2O)_n$—.

In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 19. In some embodiments, n is 20.

In some embodiments, a linker moiety, e.g., L) is or comprises one or more, e.g., 1, 2, 3, 4, 5, 6, 7, 8, 9, 10, 11, 12, 13, 14, 15, 16, 17, 18, 19, 20 or more) amino acid residues. As used in this specification, "one or more" can be 1-100, 1-50, 1-40, 1-30, 1-20, 1-10, 1-5, 1, 2, 3, 4, 5, 6, 7, 8, 9, 10, 11, 12, 13, 14, 15, 16, 17, 18, 19, or 20 or more. In some embodiments, one or more methylene units of L are independently replaced with an amino acid residue. In some embodiments, one or more methylene units of L are independently replaced with an amino acid residue, wherein the amino acid residue is of an amino acid of formula LNK101 or a salt thereof. In some embodiments, one or more methylene units of L are independently replaced with an amino acid residue, wherein each amino acid residue independently has the structure of —$N(R^{a1})$-$L^{a1}$-$C(R^{a2})(R^{a3})$-$L^{a2}$-CO— or a salt form thereof.

In some embodiments, a linker moiety comprises one or more moieties, e.g., amino, carbonyl, etc., that can be used for connection with other moieties. In some embodiments, a linker moiety comprises one or more —NR'—, wherein R' is described in this specification. In some embodiments, —NR'— improves solubility. In some embodiments, —NR'— serves as connection points to another moiety. In some embodiments, R' is —H. In some embodiments, one or more methylene units of L are independently replaced with —NR'—, wherein R' is as described in this specification.

In some embodiments, a linker moiety, e.g., L, comprises a —C(O)— group, which can be used for connections with a moiety. In some embodiments, one or more methylene units of L are independently replaced with —C(O)—.

In some embodiments, a linker moiety, e.g., L, comprises a —NR'— group, which can be used for connections with a moiety. In some embodiments, one or more methylene units of L are independently replaced with —N(R')—.

In some embodiments, a linker moiety, e.g., L, comprises a —C(O)NR'— group, which can be used for connections with a moiety. In some embodiments, one or more methylene units of L are independently replaced with —C(O)N(R')—.

In some embodiments, a linker moiety, e.g., L, comprises a —$C(R')_2$— group. In some embodiments, one or more methylene units of L are independently replaced with —$C(R')_2$—. In some embodiments, —$C(R')_2$— is —CHR'—. In some embodiments, R' is —$(CH_2)_2C(O)NH(CH_2)_{11}COOH$. In some embodiments, R' is —$(CH_2)_2COOH$. In some embodiments, R' is —COOH.

In some embodiments, a linker moiety is or comprises one or more ring moieties, e.g., one or more methylene units of L are replaced with -Cy-. In some embodiments, a linker moiety, e.g., L, comprises an aryl ring. In some embodiments, a linker moiety, e.g., L, comprises a heteroaryl ring. In some embodiments, a linker moiety, e.g., L, comprises an aliphatic ring. In some embodiments, a linker moiety, e.g., L, comprises a heterocyclyl ring. In some embodiments, a linker moiety, e.g., L, comprises a polycyclic ring. In some embodiments, a ring in a linker moiety, e.g., L, is 3-20 membered. In some embodiments, a ring is 5-membered. In some embodiments, a ring is 6-membered. In some embodiments, a ring in a linker is the product of a cycloaddition reaction, e.g., click chemistry, and variants thereof used to link different moieties together.

In some embodiments, a linker moiety, e.g., L, is or comprises

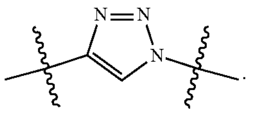 [SMILES: *c1cn(*)nn1]

In some embodiments, a methylene unit of L is replaced with

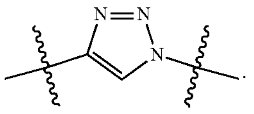 [SMILES: *c1cn(*)nn1]

In some embodiments, a methylene unit of L is replaced with -Cy-. In some embodiments, -Cy- is.

In some embodiments, a linker moiety, e.g., L) is or comprises —CO)y-. In some embodiments, L is or comprises —$[(CH_2)nO]mCy[(CH_2)nO]mNH$, or L is —$[(CH_2)nO]mCy[(CH_2)nO]mNHC(O)[(CH_2)nO]mNH$—, or L is —$[(CH_2)nO]mCy[(CH_2)nO]m\{NHC(O)[(CH_2)nO]m\}pNH$—, where n, m, and p are independently chosen at each occurrence from 1-20, from 1-12, or 2-10. In some embodiments, each n is 2, and m is independently chosen at each occurrence from an integer from 2-10. In some embodiments, m is independently chosen from an integer from 2-6, and Cy is

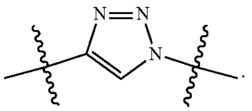

In some embodiments, a methylene unit of L is replaced with -Cy-. In some embodiments, -Cy- is

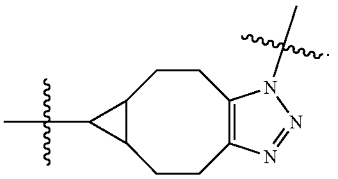 [SMILES: *C1C2CCc3nnn(*)c3CCC12]

In some embodiments, -Cy- is

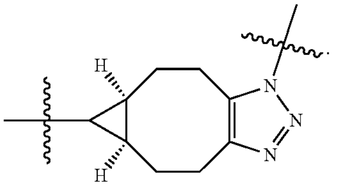 [SMILES: *C1[C@H]2CCc3c(nnn3*)CC[C@@H]12]

In some embodiments, -Cy- is

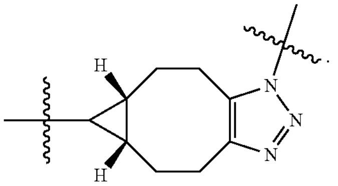 [SMILES: *C1[C@H]2CCc3nnn(*)c3CC[C@@H]12]

In some embodiments, $L^{RM}$ is a covalent bond. In some embodiments, $L^{RM}$ is not a covalent bond. In some embodiments, $L^{RM}$ is or comprises —$(CH_2CH_2O)n$-. In some embodiments, $L^{RM}$ is or comprises —$(CH_2)n$-O—$(CH_2CH_2O)n$-$(CH_2)n$-, wherein each n is independently as described in this specification, and each —$CH_2$— is independently optionally substituted. In some embodiments, $L^{RM}$ is —$(CH_2)n$-O—$(CH_2CH_2O)n$-$(CH_2)n$-, wherein each n is independently as described in this specification, and each —$CH_2$— is independently optionally substituted. In some embodiments, $L^{RM}$ is —$(CH_2)_2$—O—$(CH_2CH_2O)n$-$(CH_2)_2$—, wherein n is as described in this specification, and each —$CH_2$— is independently optionally substituted. In some embodiments, $L^{RM}$ is —$(CH_2)_2$—O—$(CH_2CH_2O)n$-$(CH_2)_2$—, wherein n is as described in this specification.

In some embodiments, $L^{PM}$ is a covalent bond. In some embodiments, $L^{PM}$ is not a covalent bond. In some embodiments, $L^{PM}$ is or comprises —$(CH_2CH_2O)n$-. In some embodiments, $L^{PM}$ is or comprises —$(CH_2)n$-O—$(CH_2CH_2O)n$-$(CH_2)n$-, wherein each n is independently as described in this specification, and each —$CH_2$— is independently optionally substituted. In some embodiments, $L^{PM}$ is —$(CH_2)$n-O—$(CH_2CH_2O)$n-$(CH_2)$n-, wherein each n is independently as described in this specification, and each —$CH_2$— is independently optionally substituted. In some embodiments, $L^{PM}$ is —$(CH_2)_2$—O—$(CH_2CH_2O)$n-$(CH_2)_2$—, wherein n is as described in this specification, and each —$CH_2$— is independently optionally substituted. In some embodiments, $L^{PM}$ is —$(CH_2)_2$—O—$(CH_2CH_2O)$n-$(CH_2)_2$—, wherein n is as described in this specification.

In some embodiments, $L^{PM}$, e.g., in a product of a first and a second agent, is or comprises a reaction product moiety formed by a first and second reactive moiety.

In some embodiments, a linker moiety, e.g., $L^{PM}$ in a product of a first and a second agent, is or comprises. In some embodiments, a methylene unit of a linker moiety, e.g., a linker moiety that can be L, e.g., $L^{RM}$ or $L^{PM}$, is replaced with -Cy-. In some embodiments, -Cy- is optionally substituted

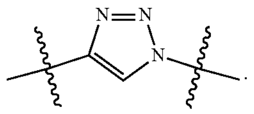

In some embodiments, -Cy- is

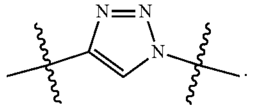 [SMILES: *c1cn(*)nn1]

In some embodiments L is —$[(CH_2)nO]mCH_2Cy[(CH_2)nO]m$. In some embodiments, -Cy- is

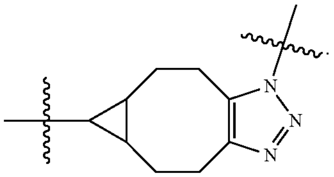 [SMILES: *C1C2CCc3nnn(*)c3CCC12]

In some embodiments, -Cy- is

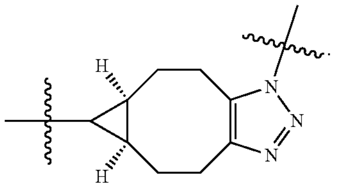 [SMILES: *C1[C@H]2CCc3c(nnn3*)CC[C@@H]12]

In some embodiments, -Cy- is

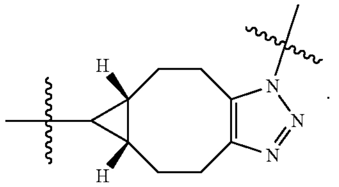 [SMILES: *C1[C@H]2CCc3nnn(*)c3CC[C@@H]12]

Cellular Receptor-Binding Moiety.

According to embodiments of the present invention, several receptor-binding moieties are described in International Patent Publications WO 2019/199621 (Yale University), WO2019/199634 (Yale University), and WO 2021/072246 (Yale University), each incorporated in this specification by reference.

In an embodiment, the cellular receptor-binding moiety may include an asialoglycoprotein receptor (ASGPR) binding group connected through an amine group to the linker moiety.

The amine group may be a primary alkyl amine group or a secondary alkyl amine group, each of which is optionally substituted on the amine group with a $C_1$-$C_3$ alkyl group.

The cellular receptor-binding moiety may include an ASGPR binding group according to the chemical structure disclosed in International Patent Publication WO 2019/199621 (Yale University).

The cellular receptor-binding moiety may have the following structure:

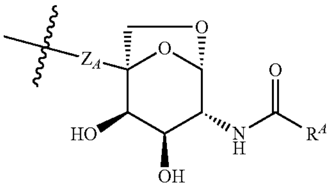

or

-continued

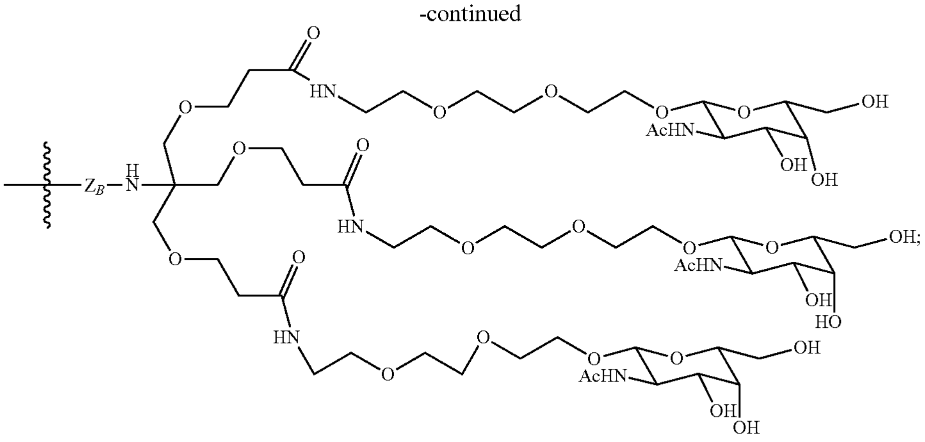

where $R^A$ is a $C_1$-$C_3$ alkyl group optionally substituted with 1-5 halo groups (preferably $R^A$ is a methyl or ethyl group optionally substituted with from 1-3 fluoro groups);

$Z_A$ is —$(CH_2)_{IM}$, —O—$(CH_2)_{IM}$, S—$(CH_2)_{IM}$, $NR_M$—$(CH_2)_{IM}$, C(O)—$(CH_2)_{IM}$—, a PEG group containing from 1 to 8 preferably 1-4 ethylene glycol residues or a —$C(O)(CH_2)_{IM}NR_M$ group (preferably a PEG containing group comprising from 1 to 8 ethylene glycol, preferably 2-4 ethylene glycol residues) where IM and RM are the same as above; and $Z_B$ is absent, $(CH_2)_{IM}$, C(O)—$(CH_2)_{IM}$— or C(O)—$(CH_2)_{IM}$—$NR_M$, where IM and $R_M$ are the same as above.

In an embodiment, $R^A$ may be a methyl or ethyl group optionally substituted with one to three fluoro groups.

In an embodiment, $Z_A$ is a PEG group containing 1 to 4 ethylene glycol residues.

In an embodiment, the methyl or ethyl group may be substituted with from 1-3 fluoro groups.

In an embodiment, the ASGPR binding group may be N-acetyl-D-galactosamine.

In an embodiment, the cellular receptor-binding moiety may be a low-density lipoprotein receptor-related protein 1 (LRP1), a low-density lipoprotein receptor (LDLR), a FcγRI binding group, a FcRn binding group, a transferrin receptor-binding group, or a macrophage scavenger receptor-binding group.

Pharmaceutically Acceptable Excipients.

Formulations suitable for parenteral administration, such as by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered by intravenous infusion, orally, topically, intraperitoneally, intravesically, or intrathecally. Parenteral, oral, and intravenous are the preferred administration methods. The formulations of compounds can be presented in unit-dose or multi-dose sealed containers, such as ampules and vials.

Solutions or suspensions used for parenteral, intradermal, or subcutaneous application can include these components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicities such as sodium chloride or dextrose. The pH can be adjusted with acids or bases, such as hydrochloric acid or sodium hydroxide. The parenteral preparation can be enclosed in ampoules, disposable syringes, or multiple dose vials made of glass or plastic.

Methods of Assessing the Chemical Structure and Function of the Agent.

Protein sequencing. In one protein sequencing method, eight digestions are prepared using five different enzymes (pepsin, Lys C, trypsin, chymotrypsin, Asp N). The digestions for the sample are processed with disulfide reduction, cysteine blocking, and then enzyme digestion. Digestions were analyzed by liquid chromatography-mass spectroscopy (LC-MS)/mass spectroscopy (MS) using a Thermo-Fisher Orbitrap Fusion™ mass spectrometer. Peptides are characterized from liquid chromatography-mass spectroscopy/mass spectroscopy data using de novo peptide sequencing and assembled into antibody sequences.

Total protein concentration can be determined by Bradford assay (Biorad). Núñez Miguel et al., Journal of Molecular Endocrinology, 70, e220120 (2022).

Statistical Analyses.

Normal distribution quantitative variables can be expressed as means and SDs and compared by an independent-sample t-test. The inventors used median and interquartile ranges for non-normally distributed variables and analyzed them with the Mann-Whitney U test. Categorical data was summarized by percentages. A two-sided p-value $<0.05$ was considered statistically significant. All statistical tests were performed using SPSS version 16.0.

GraphPad Prism (GraphPad Software, Inc., La Jolla, CA, USA) can be used to fit a dose-response curve using non-linear regression and calculate the $EC_{50}$ of each agonist. See Miller-Gallacher et al., Journal of Molecular Endocrinology, 62, 117-128 (2019).

Methods to Detect TSH Receptor Antibodies.

Measurements of TSH receptor autoantibodies are important in diagnosing and managing Graves' disease and other thyroid disorders. It is well documented in the biomedical art that patient TSH receptor autoantibodies bind to regions on the TSHR leucine-rich domain overlapping with each other and the TSH binding site. There are differences in the TSH receptor residues in contact with autoantibodies present in different sera. Persons having ordinary skill in the art can use any of four types of assay are used to measure TSH receptor autoantibodies described by International Patent Publication WO 2015/189543 (RSR Ltd.). (1) Competitive binding assays which measure the ability of patient serum TSH receptor autoantibodies to inhibit the binding of TSH or human monoclonal TSH receptor autoantibodies to preparations of TSH receptor. (2) Bioassays which measure the ability of TSH receptor autoantibodies to stimulate cells expressing the TSH receptor in culture. (3) Immunoprecipitation of labeled TSH receptor preparations with TSH receptor autoantibodies. (4) Bridge-type assays in which divalent TSH receptor autoantibodies bind to TSHR coated onto ELISA plate wells with one arm and to liquid phase TSHR260-alkaline phosphatase fusion protein with the other arm to form a bridge. An ELISA described in International Patent Publication WO 2010/07301 is based on the ability of divalent TSHR antibodies to bind with one antigen binding site to TSHR coated onto an ELISA plate well and with the other antigen binding site to TSHR260-AP in liquid phase, i.e., forming a bridge. The assay relies on the bivalent properties of human monoclonal stimulating type TSHR autoantibodies and the human monoclonal blocking type TSHR autoantibody to form a bridge between immobilized full-length wild type TSHR and alkaline phosphatase labeled TSHR260 mutants.

A suitable binding assay may comprise a plate having bound thereto a TSHR fragment to be tested and a labeled antibody or autoantibody to TSHR. The TSHR to be tested is suitably bound to the plate in such a way so as not to interfere with the binding of the antibody to the TSHR protein. The TSHR may be bound to the plate using any suitable antibody. One such antibody is mouse monoclonal TSH receptor antibody 14C4. See International Patent Publication WO 2015/189543 (RSR Ltd.). The amount of labeled antibody bound can be used to indicate the amount of active mutant protein.

The activity in the TSHR activity assay may be expressed in any suitable way, for example as the amount of activity per volume of sample, i.e., units per ml. The activity is the specific activity as measured in units of activity per quantity of protein—for example, units per mg. See International Patent Publication WO 2015/189543 (RSR Ltd.).

Characterizing Antibody-Binding Moieties.

Many technologies are available for identifying, assessing, or characterizing antibody-binding moieties, including protein-binding moieties, e.g., antibody-binding moieties such as universal antibody-binding moieties, or their use in provided technologies, e.g., those described in International Patent Publication WO 2019/023501, the technologies of which are incorporated in this specification by reference. In some embodiments, an antibody-binding moiety is a moiety, e.g., a small molecule, peptide, nucleic acid, etc., that can selectively bind to IgG and provide or stimulate ADCC or ADCP. In some embodiments, peptide display technologies, e.g., phase display, non-cellular display, etc., can identify antibody-binding moieties. In some embodiments, an antibody-binding moiety is a moiety, e.g., small molecule moiety, peptide moiety, nucleic acid moiety, etc., that can bind to IgG and optionally can compete with known antibody binders, e.g., protein A, protein G, protein L, etc.

Persons having ordinary skill in the biomedical art know that antibody-binding moieties described in this specification target antibodies with several properties and activities, e.g., antibodies recognizing different antigens, having optional modifications, etc. In some embodiments, these antibodies include antibodies administered to a subject, e.g., for therapeutic purposes. In some embodiments, antibody-binding moieties described in this specification may bind antibodies toward different antigens and are useful for conjugating moieties of interest with several antibodies.

In some embodiments, an antibody-binding moiety comprises a meditope agent moiety. A meditope agent is described in, e.g., Patent Publication US 2019/0111149.

In some embodiments, an antibody-binding moiety, e.g., an antibody-binding moiety, can bind to human IgG. In some embodiments, an antibody-binding moiety, e.g., an antibody-binding moiety, can bind to an antibody selected from the Markush group of antibodies consisting of rabbit IgG, IgG1, IgG2, IgG3, and IgG4. In some embodiments, an antibody-binding moiety, e.g., an antibody-binding moiety, binds to IgG1, IgG2, and IgG4.

Specific Mutation Strategies to Reduce FcγR and c1q Binding and Effector Functions and to Enhance FcRn Binding and Exposure of Antibodies.

Fc Mutation Strategies to Reduce FcγR and c1g Binding.

The inventors mutate an antibody, an antibody variant, or an antigen-binding fragment thereof in the Fc region to insert a LALA mutation using biomedical art-recognized methods first described by the Winter group in the 1990s. In this EXAMPLE, LALA=L234A/L235A.

The inventors mutate an antibody, an antibody variant, or an antigen-binding fragment thereof in the Fc region to insert a LALA mutation using biomedical-art recognized methods first described by the Winter group in the 1990s, then inserted P mutations, such as by the biomedical-art recognized methods introduced by Roche team in 2016, such as the technology for adding P329G and P329G combined with LALA: In this EXAMPLE, LALA/PA=L234A/L235A/P329A. LALA/PG=L234A/L235A/P329G. See Tilman et al., Protein Engineering, Design and Selection, Volume 29, Issue 10, pages 457-466 (October 2016), which shows that LALA abolishes c1q binding. P329A alone was tested. P329A abolishes c1q binding and reduces FcgR binding. They show that P329G/LALA further reduces FcγR binding beyond LALA alone.

Persons having ordinary skill in the biomedical art can also mutate an antibody, an antibody variant, or an antigen-binding fragment thereof in other regions. N297A/Q removes the natural N-linked glycosylation site in the hinge region.

Fc Mutation Strategies to Enhance FcRn Binding to Prolong Exposure.

There are many publicly available approaches and mutation sets to increase the binding of an Fc to FcRn. See TABLE 4. Strohl, Current Opinion in Biotechnology, 20 (6), 685-691 (2009), which provided an older summary.

TABLE 2

| Examples of Fc sequence engineering for modification of half-life. | | |
|---|---|---|
| Function | Company or source | Mutations or changes |
| Increased half-life | MedImmune | IgG1-M252Y, S254T, T256E |
| Increased half-life | Protein Design Labs | IgG1-T250Q, M428L |
| Increased half-life | Genentech | IgG1-N434A |
| Increased half-life | Sally Ward | IgG1-H4J3K, N434Y |
| Increased half-life | Deny Roopenian | IgG1-T307A, E380A, N434A |
| Increased half-life | Xeocor Xtend ™ technology | |
| Lowered endogenous IgG | Sally Ward | IgG1-M252 Y, S254T, T256E, H433K, N434F, 436H |
| Decreased half-life | Deny Roopenian | IgG1-1253A |
| Decreased half-life | Eli Lilly | IgG1-P2571, N434H or Q376V, N434H |

For an example of introducing a YTE region in a protein (M252Y/S254T/T256E), see Acqua et al., The Journal of Immunology 169 (9), 5171-5180 (2002). For a recent example combining LALA and YTE, see Cobb et al., bioRxiv, 2021-09 (2021). Additional references with details of engineering are also available.

For an example of introducing an LS region in a protein (M428L/N434S), see Zalevsky et al., Nature Biotechnology, 28 (2), 157-159 (2010).

Structure of Recombinant Ligand Constructs.

GN3 sortase reagent. Persons having ordinary skill in the biomedical art have access to commercially available protocols for sortase conjugation using the ASPGR binder for the C-terminal sortase tag (LPETGG) for conjugation (GN3/linker).

GN3-maleimide reagent (maleimide-GN3/linker), with a C-terminal cysteine for conjugation.

Methods of Making Agents.

Agents of this specification may be prepared or isolated by synthetic or semi-synthetic methods or recombinant methods in accordance with this specification. In some embodiments, polypeptide agents, e.g., cellular receptor-binding moiety peptide agents, may be prepared using biological expression systems. In some embodiments, provided agents are prepared synthetically. In some embodiments, provided agents are prepared using certain technologies described in WO 2019/023501, which is incorporated in this specification in its entirety by reference.

Several technologies, e.g., those for preparing antibody-drug conjugates, may be used in preparing MATE agents. In some embodiments, the invention provides technologies that can be used for selective conjugation of anti-TSH receptor autoantibody-binding moieties at amino acid residue sites.

In some embodiments, the invention provides a method of synthesis, comprising the steps of:

- contacting a first agent comprising a cellular receptor-binding moiety linked to a first reactive group optionally through a first linker with a second agent comprising an antibody moiety linked to a second reactive group optionally through a second linker, wherein the first reactive group reacts with a second reactive group, and
- forming a product agent comprising a cellular receptor-binding moiety and an antibody-binding moiety optionally through a linker.

In some embodiments, the invention provides a method of synthesis comprising the steps:

- contacting a first composition comprising a plurality of first agents, each independently comprising a cellular receptor-binding moiety linked to a first reactive group optionally through a first linker moiety, with a second composition comprising a plurality of second agents, each independently comprising an antibody moiety optionally linked to a second reactive group, optionally through a second linker moiety,
- wherein a product composition comprising a plurality of product agents, each independently comprising a cellular receptor-binding moiety and an antibody-binding moiety optionally through a linker, is formed.

Commercially Available Reagents Useful for Making Agents.

Anti-TSHR M22 (Fab), stimulating antibody (Cell Sciences, catalogue #FHD18110B), which binds to the leucine-rich domain of TSHR. The antibody binding overlaps with that of the native ligand, TSH.

Anti-human TSHR antibody K1-70 (Dima Biotech, BME100080).

Recombinant human TSHR ectodomain Fc-fusion chimera (Biotechne, catalogue #8950-TR).

Recombinant human TSHR extracellular domain, with C-terminal histidine (SinoBiological, catalogue #17299-H08B).

Recombinant Human TSHR leucine-rich domain, amino acids 22-260 with histidine tag (MyBioSource, catalogue #MBS355800).

Thyrotropic hormone from human pituitary (Millipore Sigma, catalogue #T9265).

Method of Assessing Agent for Administration

Persons having ordinary skill in the biomedical art can analyze an agent formulation for appearance, color, and achromicity using the criteria described by the United States Pharmacopeia-National Formulary in USP <631> or by the European Pharmacopoeia in Ph. Eur. 2.2.2.

Persons having ordinary skill in the biomedical art can analyze an agent formulation for appearance and clarity using the criteria described by the United States Pharmacopeia-National Formulary in USP <1061> or by the European Pharmacopoeia in Ph. Eur. 2.2.2.

Persons having ordinary skill in the biomedical art can analyze an agent formulation for pH using the criteria described by the United States Pharmacopeia-National Formulary in USP<<791> or by the European Pharmacopoeia in Ph. Eur. 2.2.3. A generally accepted criterion is +0.5 pH of the targeted pH.

Persons having ordinary skill in the biomedical art can analyze the drug product for osmolality using the criteria described by the United States Pharmacopeia-National Formulary in USP <785> or by the European Pharmacopoeia in Ph. Eur. 2.2.35.

Persons having ordinary skill in the biomedical art can quantify the concentration of an agent by UV-VIS spectroscopy, e.g., at A280 (280 nm). A generally accepted criterion is ±10% of the targeted concentration.

Persons having ordinary skill in the biomedical art can confirm the Identity of an agent by the charge variant peak retention time or pl as measured by imaged capillary isoelectric focusing (iCIEF), a high-resolution technique that separates proteins into groups based on their isoelectric point (pl).

Persons having ordinary skill in the biomedical art can confirm the purity of the agent by the HIC-HPLC method. For example, the persons having ordinary skill in the biomedical art can confirm the DAR of the agent. A generally accepted criterion is ±10% of the targeted concentration.

Persons having ordinary skill in the biomedical art can confirm the purity of an agent formulation by the SE-HPLC method. For example, the persons having ordinary skill in the biomedical art can confirm the percentage of a monomer, high molecular weight, and low molecular weight. A generally accepted criterion is a result of ≥90% or ≤5%.

Persons having ordinary skill in the biomedical art can confirm the purity of an agent formulation by the CE-SDS-NR method. For example, the persons having ordinary skill in the biomedical art can confirm the percentage of a main peak and fragment peaks. A generally accepted criterion is a result of ≥85%.

Persons having ordinary skill in the biomedical art can confirm the purity of an agent formulation by the CE-SDS-R method. For example, the persons having ordinary skill in the biomedical art can confirm the percentage of monomer and Minor species peaks. A generally accepted criterion is a result of ≥85%.

Persons having ordinary skill in the biomedical art can confirm the purity of an agent formulation by the iCIEF method. For example, the persons having ordinary skill in the biomedical art can confirm the percentage of charge variants.

Persons having ordinary skill in the biomedical art can confirm the potency of an agent for binding by the ELISA method. A generally accepted criterion is ± a defined percentage as compared to a reference standard.

Persons having ordinary skill in the biomedical art can detect a process impurity (HCP) in an agent formulation by the ELISA method. A generally accepted criterion is ≤100 ng/mg.

Persons having ordinary skill in the biomedical art can detect a process impurity (rProtein A) in an agent formulation by the ELISA method. A generally accepted criterion is ≤50 ng/mg.

Persons having ordinary skill in the biomedical art can detect an rDNA impurity in an agent formulation by the rtPCR method. A generally accepted criterion is <10 ng per dose.

Persons having ordinary skill in the biomedical art can confirm the purity of an agent formulation by the RP-HPLC method. For example, the persons having ordinary skill in the biomedical art can confirm the presence of residual free drug & free protein intermediates.

Persons having ordinary skill in the biomedical art can analyze an agent formulation for the presence of endotoxins using the criteria described by the United States Pharmacopeia-National Formulary in USP <85> or by the European Pharmacopoeia in Ph. 2.6.14. A generally accepted criterion is dose dependent based on <5 EU/kg.

Persons having ordinary skill in the biomedical art can analyze a drug substance for its bioburden using the criteria described by the United States Pharmacopeia-National Formulary in USP <61> or by the European Pharmacopoeia in Ph. 2.6.12. A generally accepted criterion is ≤1 CFU/10 mL.

Persons having ordinary skill in the biomedical art can analyze a drug product for its sterility using the criteria described by the United States Pharmacopeia-National Formulary in USP <71> or by the European Pharmacopoeia in Ph. 2.6.1. A generally accepted criterion is no growth.

Persons having ordinary skill in the biomedical art can analyze a drug product for the presence of excipients using the HPLC-ELSD method For example, the persons having ordinary skill in the biomedical art can measure the percentage of surfactants. A generally accepted criterion is ±50% of the targeted value.

Persons having ordinary skill in the biomedical art can analyze a drug product for the subvisible particles in a container using the criteria described by the United States Pharmacopeia-National Formulary in USP <787> or by the European Pharmacopoeia in Ph. 2.6.19. Several accepted criterion are known to persons having ordinary skill in the biomedical art.

Persons having ordinary skill in the biomedical art can analyze a drug product for the extractable volume using the criteria described by the United States Pharmacopeia-National Formulary in USP <697> or by the European Pharmacopoeia in Ph. 2.6.17.

Persons having ordinary skill in the biomedical art can analyze a drug product for Container Closure Integrity Test (CCIT), using the criteria described by the United States Pharmacopeia-National Formulary in USP <1207>. A bioburden test is usually performed at the final stability time only. A CCIT test is usually performed at repeated time intervals, e.g., annually.

EXAMPLES

The invention is further illustrated by non-limited EXAMPLES.

Example 1

Procedure for Preparation of Int-00027

Preparation of Intermediate 2

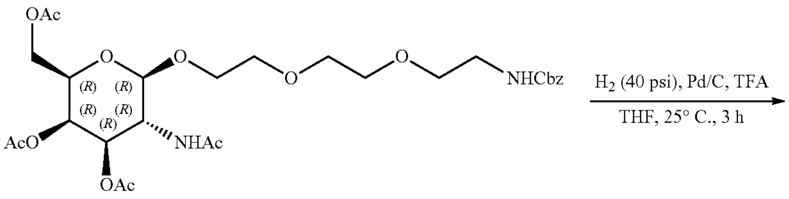

1

-continued

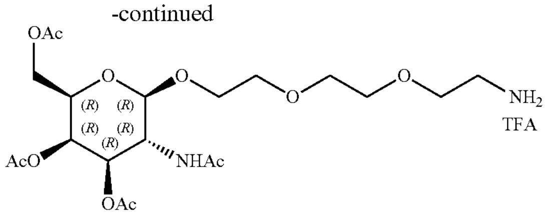

2

Pd/C (4.00 g, 10% purity) in reaction bottle (purged with argon gas for three times) was added tetrahydrofuran (40 mL) slowly, then a solution of trifluoroacetic acid (7.44 g, 65.2 mmol, 4.86 mL, one equivalent) and Intermediate 1 (40.0 g, 65.2 mmol, 1.00 equivalent) in tetrahydrofuran (360 mL) was added to the reaction slowly under nitrogen gas. The reaction was degassed and purged with argon gas and hydrogen gas for three times, then stirred at 25° C. for three hours under hydrogen gas atmosphere (40 psi). Thin-layer chromatography (DCM: methanol=10:1, $R_f$=0.20) indicated Intermediate 1 was consumed completely, and one major new spot with larger polarity was detected. The reaction mixture was dissolved in tetrahydrofuran (100 mL), filtered carefully through siliceous earth under nitrogen gas atmosphere, the cake was washed with tetrahydrofuran (100 mL*2), and the filtrate was concentrated under reduced pressure to get Intermediate 2 (38.7 g, 38.5 mmol, 59.0% yield, 59.0% purity, trifluoroacetic acid salt) as a white solid. liquid chromatography-mass spectroscopy: retention time is 0.428 minutes, MS calculated: 478.22, mass observed: $[M+Na]^+$=501.2. $^1$H NMR (400 MHz, dimethyl sulfoxide (DMSO)-$d_6$) δ ppm 7.79-7.91 (m, 3H), 5.16-5.28 (m, 1H), 4.97 (br dd, J=11.07, 2.81 Hz, 1H), 4.54 (br d, J=8.50 Hz, 1H), 4.03 (s, 2H), 3.77-3.93 (m, 2H), 3.53-3.62 (m, 8H), 2.98 (br d, J=5.00 Hz, 2H), 2.10 (s, 3H), 2.00 (s, 3H), 1.89 (s, 3H), 1.78 (s, 3H).

Preparation of Intermediate 4

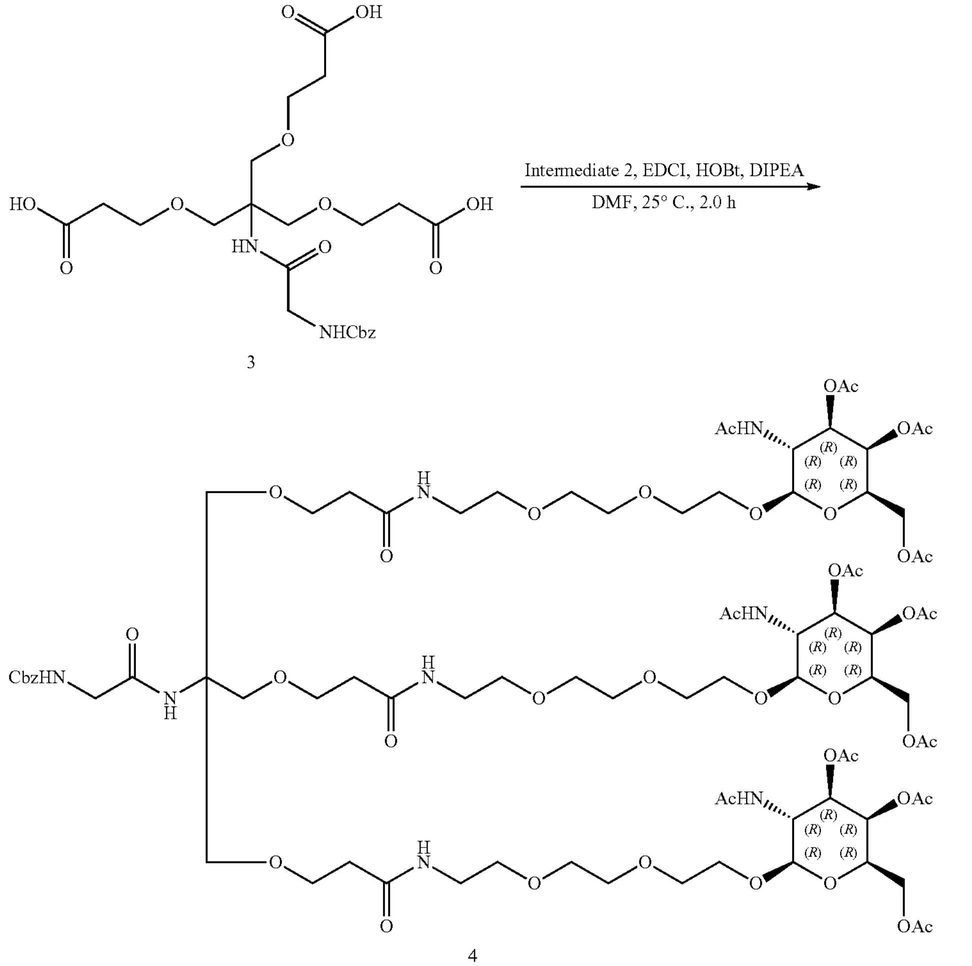

3

4

To a stirring solution of Intermediate 3 (8.50 g, 16.0 mmol, 1.00 equivalent) and Intermediate 2 (38.1 g, 64.3 mmol, 4.00 equivalents, trifluoroacetic acid salt) in DMF (17 mL) and DCM (340 mL) was added HOBT (8.69 g, 64.3 mmol, 4.00 equivalents), EDCl (12.3 g, 64.3 mmol, 4.00 equivalents) and DIEA (9.35 g, 72.3 mmol, 4.50 equivalents) successively. The reaction was stirred at 25° C. for two hours. Thin-layer chromatography (DCM: methanol=10:1, $R_f$=0.5) indicated Intermediate 3 was consumed completely, and one major new spot with larger polarity was detected. The reaction mixture was slowly poured into a stirring cold 1.0 mol/L HCl solution (350 mL) and stirred for ten minutes. White precipitate was formed and filtered. The aqueous phase was extracted with DCM (350 mL*2) twice. The combined organic layers were washed with saturated $NaHCO_3$ (350 mL), dried over $Na_2SO_4$, and concentrated under reduced pressure to get a residue. The residue was purified by column chromatography ($SiO_2$, DCM: methanol=100:1 to 15:1) to make Intermediate 4 (22.0 g, 10.6 mmol, 66.0% yield, 92.2% purity) as a white solid. $^1$H NMR (400 MHZ, DMSO-$d_6$) δ ppm 7.91 (br t, J=5.32 Hz, 3 H), 7.81 (d, J=9.26 Hz, 3H), 7.26-7.49 (m, 6H), 7.12 (s, 1H), 5.21 (d, J=3.25 Hz, 3H), 5.02 (s, 2H), 4.97 (dd, J=11.13, 3.25 Hz, 3H), 4.55 (d, J=8.38 Hz, 3H), 4.03 (s, 9H), 3.84-3.92 (m, 3H), 3.74-3.82 (m, 3 H), 3.47-3.65 (m, 38H), 3.39 (br s, 3H), 3.20 (q, J=5.42 Hz, 6H), 2.30 (br t, J=6.13 Hz, 6H), 2.10 (s, 9 H), 1.99 (s, 9H), 1.89 (s, 9H), 1.77 (s, 9H). liquid chromatography-mass spectroscopy: retention time is = 0.403 minutes, MS calculated: 1908.81, mass observed: $[M+2H]^{2+}$=1910.2.

Preparation of Intermediate 5

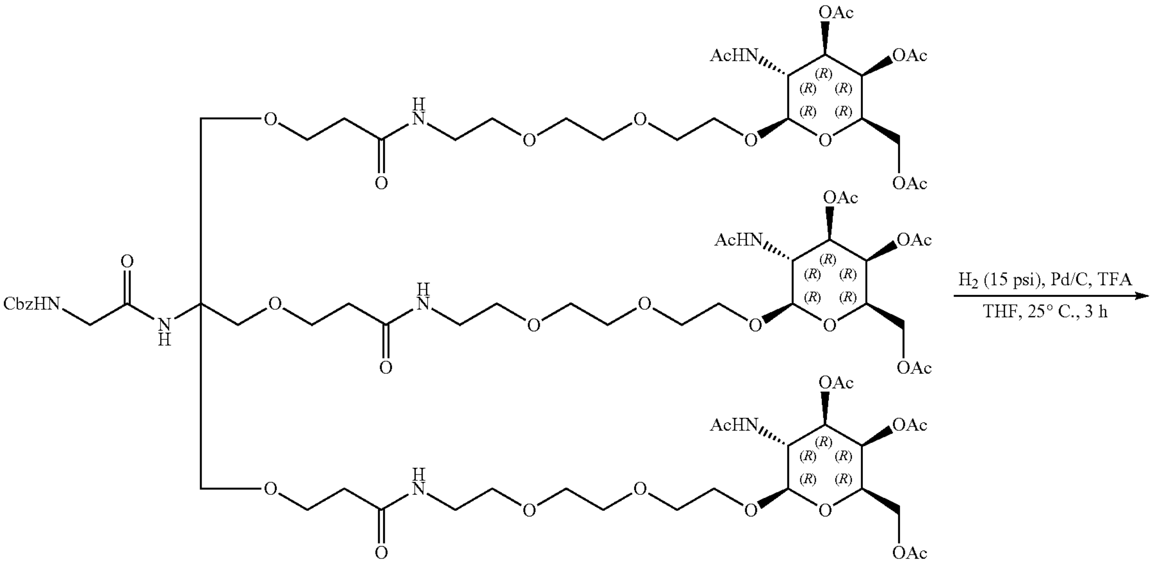

4

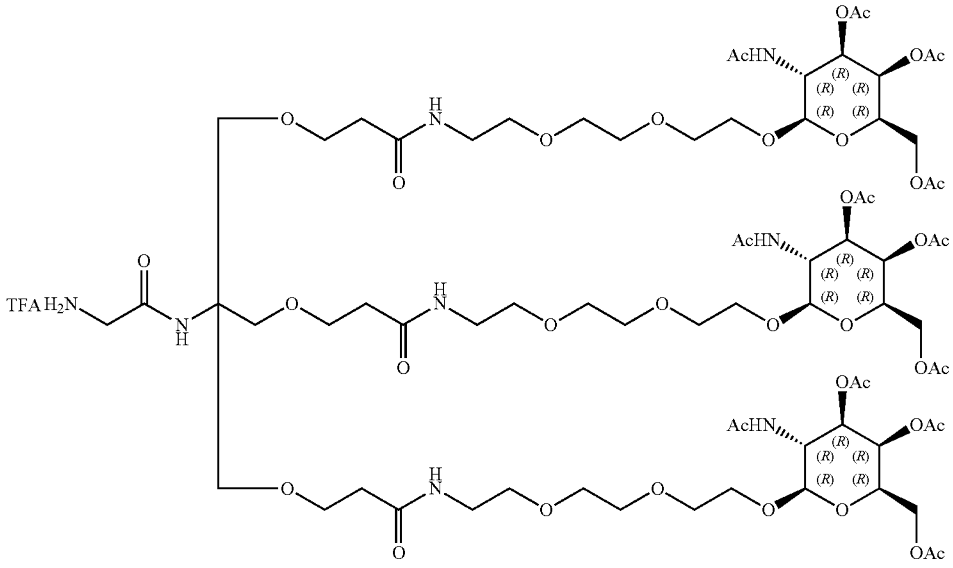

5

The 500 mL round-bottom flask was purged with argon gas for three times and added dry Pd/C (1.60 g, 1.50 mmol, 10% purity, 0.17 equivalents) carefully. Tetrahydrofuran (60.0 mL) was added to infiltrate the Pd/C completely, followed by the solution of Intermediate 4 (16.4 g, 8.59 mmol, 1.00 equivalent) and trifluoroacetic acid (979 mg, 8.59 mmol, 637.8 μL, 1.00 equivalent) in tetrahydrofuran (100 mL) slowly under argon gas atmosphere. The resulting mixture was degassed and purged with hydrogen gas for three times, and then the mixture was stirred at 25° C. for three hours under hydrogen gas atmosphere (15 psi). Thin-layer chromatography (DCM: methanol=10:1, $R_f$=0.6) indicated Intermediate 9 was consumed completely, and one major new spot was detected. The reaction mixture was filtered carefully through siliceous earth under nitrogen gas atmosphere, the cake was washed with tetrahydrofuran (50 mL*2). Then, the filter cake was added water immediately. The organic layer concentrated under reduced pressure to make Intermediate 5 (15.7 g, 6.78 mmol, 78.9% yield, 81.6% purity, trifluoroacetic acid salt) as a white solid. $^1$H NMR (400 MHZ, DMSO-$d_6$) δ ppm 7.91-7.98 (m, 5H), 7.82 (br d, J=9.13 Hz, 3H), 7.74 (s, 1H), 7.12-7.28 (m, 1H), 5.22 (br d, J=2.63 Hz, 3H), 4.97 (br dd, J=11.13, 2.75 Hz, 3H), 4.54 (d, J=8.51 Hz, 3H), 3.84-3.93 (m, 3H), 3.78 (br dd, J=10.13, 4.88 Hz, 3H), 3.53-3.62 (m, 22H), 3.33-3.45 (m, 22H), 3.18-3.25 (m, 6H), 2.31 (br t, J=6.13 Hz, 6H), 2.10 (s, 9H), 2.00 (s, 9H), 1.89 (s, 9H), 1.73-1.81 (m, 14H). liquid chromatography-mass spectroscopy: retention time is 0.341 minutes, MS calculated: 1774.7, found: $[M+2H]^{2+}$=1776.9.

Preparation of Intermediate Target A001A

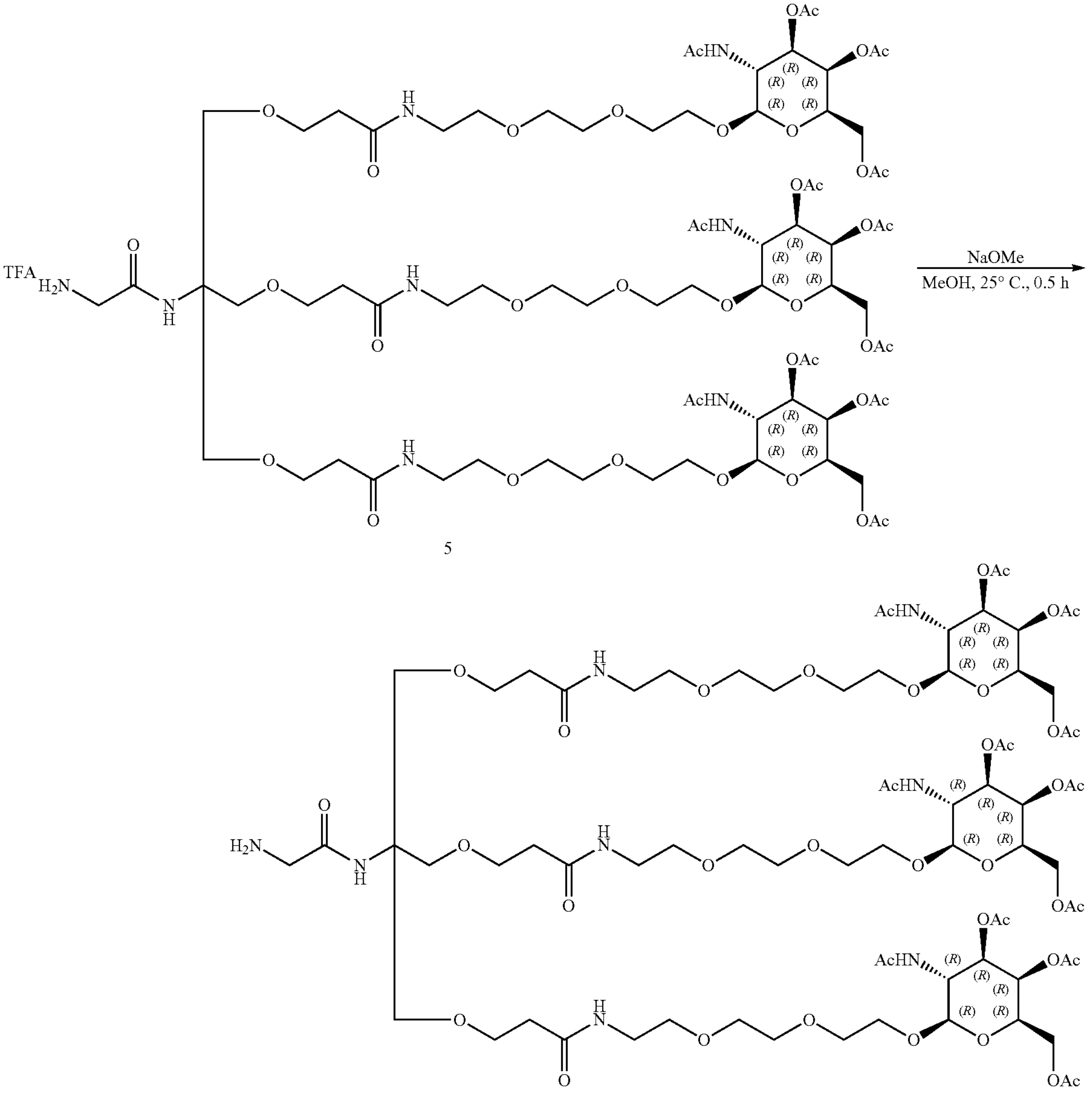

5

Target A001A

To a solution of Intermediate 5 (5.5 g, 2.91 mmol, 1.00 equivalent, trifluoroacetic acid) in methanol (50.0 mL) was added NaOMe (707 mg, 13.1 mmol, 4.50 equivalent) at 0° C. The mixture was stirred at 0° C. for 0.5 hours. The reaction was monitored by liquid chromatography-mass spectroscopy, which showed the desired mass (one main peak with desired was detected.). The reaction mixture was added with 1.0 M HCl solution till the pH=6. The mixture was diluted with water (75.0 mL) and extracted with DCM (120 mL*3). The mixture was freeze-dried to make Target A001A (4.1 g, 2.74 mmol, 94.1% yield, 93.4% purity, HCl) as a white solid. $^1$H NMR (400 MHZ, DMSO-$d_6$) δ ppm 7.94 (br t, J=5.50 Hz, 3H), 7.62 (d, J=9.01 Hz, 3H), 7.54 (s, 1H), 4.28 (d, J=8.50 Hz, 3H), 3.70-3.88 (m, 6H), 3.61-3.70 (m, 6H), 3.49-3.57 (m, 31H), 3.38-3.43 (m, 12H), 3.31 (br d, J=6.25 Hz, 4H), 3.17 (s, 6H), 3.09 (s, 2H), 2.30 (br t, J=6.32 Hz, 6H), 1.80 (s, 9H). liquid chromatography-mass spectroscopy: retention time is 0.22 minutes, MS calculated: 1396.6, found: $[M+H]^+$=1397.8.

Preparation of Intermediate Int-00027

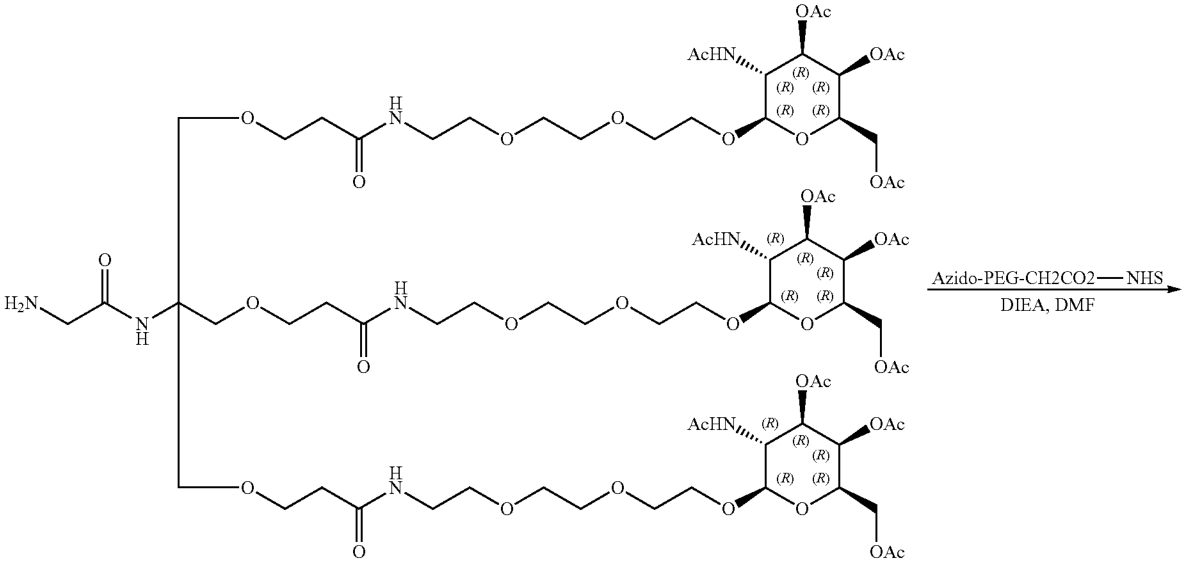

Target A001A

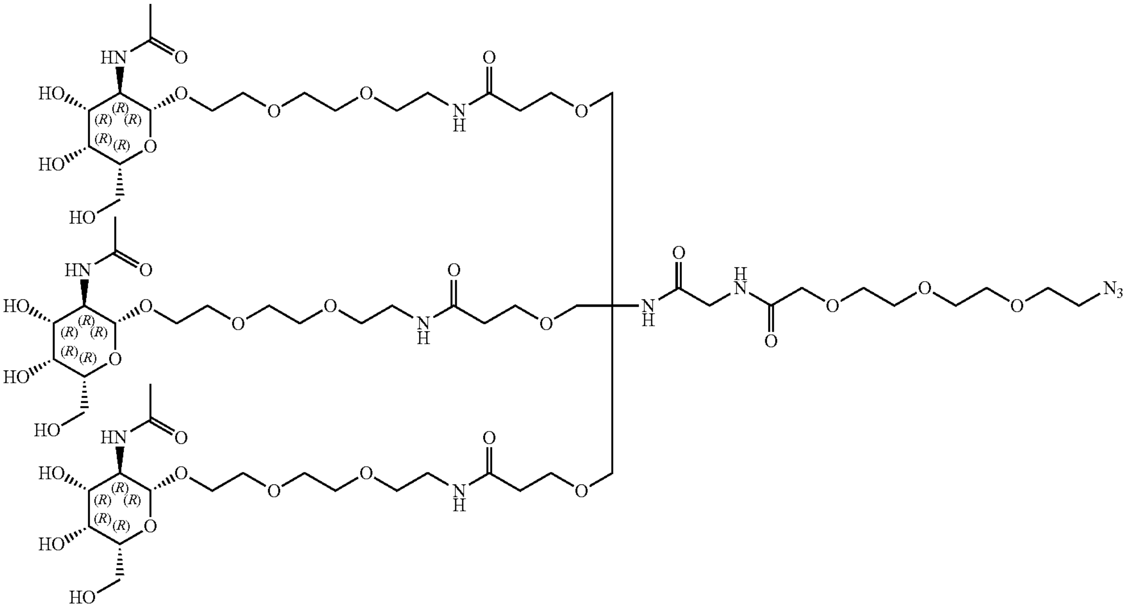

Int-00027

To a solution of Target A001A (2.00 g, 1.43 mmol, 1.00 equivalent) and Azido-PEG3-CH2CO2-NHS (567 mg, 1.71 mmol, 1.20 equivalents) in DMF (20 mL) was added DIEA (554 mg, 4.29 mmol, 709 μL, 3.00 equivalents) at 0° C. The mixture was stirred at 0° C. for two hours under nitrogen gas atmosphere. liquid chromatography-mass spectroscopy indicated Target A001A was consumed completely, one main peak with desired MS was detected. The residue was purified by prep-high performance liquid chromatography (AcOH condition) directly to make Int-00027 (1.75 g, 1.04 mmol, 73.2% yield, 96.5% purity) as a white solid. liquid chromatography-mass spectroscopy: Retention time is 0.286 minutes, MS calculated: $M_{av}$=1612.68, $[M+2H]^{2+}$=807.1, $[M-sugar+2H]^{2+}$=705.6.

Example 2

Preparation of Building Block #1

Preparation of Intermediate 2

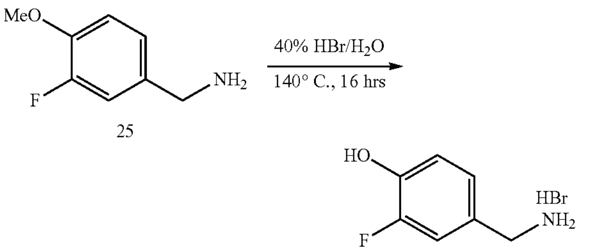

25

26

A mixture of Intermediate 25 (75.0 g, 64.4 mmol) in HBr/water (40% HBr, 1000 mL in total) was stirred at 140° C. for 16 h. The solvent was removed at 70° C. under reduced pressure. The residue was triturated in acetonitrile (50 mL) for ten minutes. After filtration, the solid was dried under lyophilization to make Intermediate 26 (100.0 g, 427.9 mmol, 88.4% yield, HBr salt) as a brown solid. 1H NMR (400 MHZ, DMSO-$d_6$) δ ppm 10.03 (s, 1H) 8.20 (s, 3H) 7.32 (dd, J=12.17, 1.88 Hz, 1H) 7.11 (dd, J=8.28, 1.51 Hz, 1H) 6.95-7.03 (m, 1H) 3.93 (q, J=5.27 Hz, 2H).

Preparation of Intermediate 27

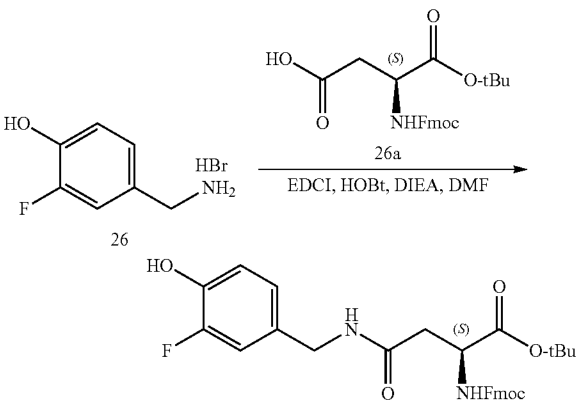

26

27

To a mixture of Intermediate 26 (60.0 g, 270.2 mmol, 1.00 equivalent, HBr salt), Reactant 26a (111.1 g, 270.2 mmol, 1.00 equivalent), DIEA (34.9 g, 270.2 mmol, 47.0 mL, 1.00 equivalent) and HOBt (54.7 g, 405.3 mmol, 1.50 equivalents) in DMF (1 L) was added EDCl (56.7 g, 297.2 mmol, 1.10 equivalents) at 20° C. The mixture was stirred at 20° C. for three hours. The mixture was precipitated with 0.5 M HCl (cold, 10 L). After filtration, the solid was dissolved in DCM (2 L), washed with 0.5 M HCl (800 mL), water (800 mL), brine (800 mL), dried over anhydrous $Na_2SO_4$ and concentrated under reduced pressure. The residue was purified by silica gel column (DCM/methanol=from 1/0 to 20/1) to make Intermediate 27 (120.0 g, 90% purity, containing a little DMF, 83.3% yield) as a white solid. $^1$H NMR (400 MHz, DMSO-$d_6$) δ ppm 9.70 (s, 1H) 8.34 (t, J=5.77 Hz, 1H) 7.90 (d, J=7.53 Hz, 2H) 7.71 (d, J=7.53 Hz, 2H) 7.61 (d, J=8.28 Hz, 1H) 7.39-7.47 (m, 2H) 7.29-7.36 (m, 2H) 7.02 (d, J=12.30 Hz, 1H) 6.85-6.92 (m, 2H) 4.20-4.39 (m, 4H) 4.11-4.19 (m, 2H) 1.36 (s, 9H).

Preparation of Building Block #1:

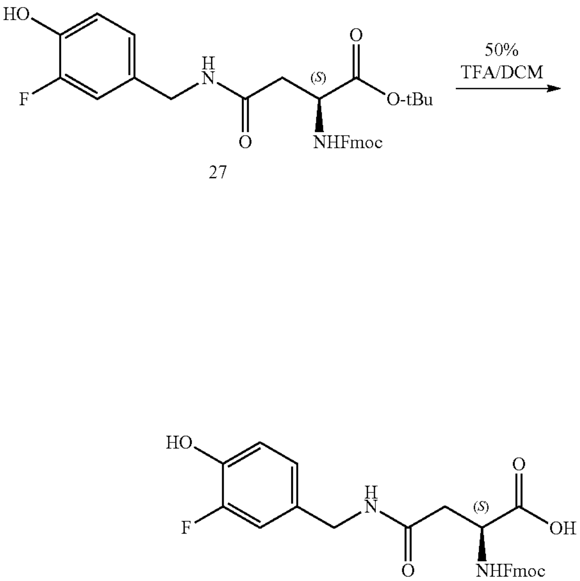

27

Molecular Weight: 478.47
Building block #1

A mixture of Intermediate 27 (120.0 g, 224.4 mmol, 1.00 equivalent) in trifluoroacetic acid (600 mL) and DCM (600 mL) was stirred at 20° C. for 0.5 h. The solvent was removed under reduced pressure. The residue was purified by silica gel column (DCM/methanol=from 1/0 to 10/1) to make Building block #1 (100.0 g, 93.5% purity, 93.1% yield) as a white solid. $^1$H NMR (400 MHZ, DMSO-$d_6$) δ ppm 9.69 (s, 1H) 8.34 (t, J=5.90 Hz, 1H) 7.90 (d, J=7.28 Hz, 2H) 7.71 (d, J=7.53 Hz, 2H) 7.54 (d, J=6.53 Hz, 1H) 7.42 (t, J=7.40 Hz, 2H) 7.27-7.37 (m, 1H) 7.27-7.37 (m, 1H) 7.02 (d, J=12.05 Hz, 1H) 6.82-6.93 (m, 2H) 4.35-4.43 (m, 1H) 4.20-4.31 (m, 3H) 4.13-4.19 (m, 2H).

Example 3

Procedure for Preparation of TBT301

Preparation of Intermediate 30: Peptide was synthesized using standard Fmoc chemistry (CTC resin).

Intermediate 30

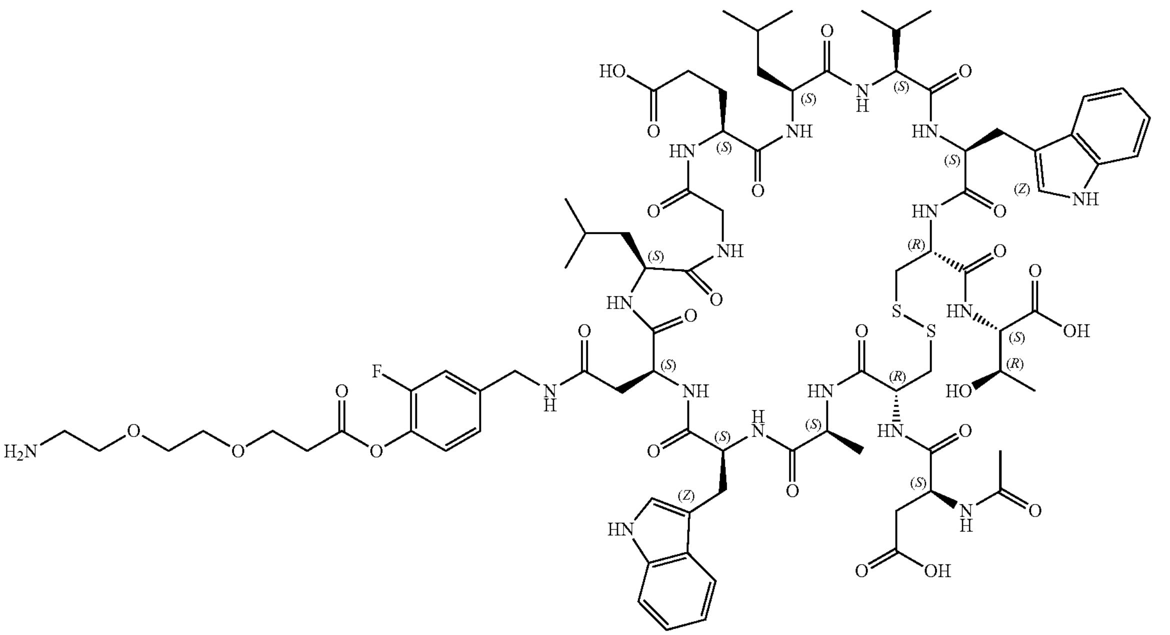

Molecular Weight: 1833.02

(1) Resin preparation: To the vessel containing CTC resin (2.0 g, 2.0 mmol, 1.00 mmol/g) and Fmoc-Thr(tBu)-OH (795 mg, 2.0 mmol, 1.00 equivalent) in DCM (50 mL) was added DIEA (4.00 equivalents) dropwise and mixed for two hours with nitrogen gas bubbling at 25° C. Then methanol (2 mL) was added and bubbled with nitrogen gas for another thirty minutes. The resin was washed with DMF (100 mL)*5, followed by the addition of 20% piperidine in DMF (100 mL) and bubbled with nitrogen gas for thirty minutes at 25° C. for Fmoc deprotection. The mixture was filtered. The resin was washed with DMF (100 mL)*5.

(2) Coupling: A solution of Fmoc-Cys(Trt)-OH (3.51 g, 6.0 mmol, 3.00 equivalents), HBTU (2.16 g, 5.7 mmol, 2.85 equivalents) in DMF (50 mL) was added to the resin with nitrogen gas bubbling. Then DIEA (6.00 equivalents) was added to the mixture dropwise and bubbled with nitrogen gas for thirty minutes at 25° C. The coupling reaction was monitored by ninhydrin test, if it showed colorless, the coupling was completed. The resin was then washed with DMF (100 mL)*5.

(3) Deprotection: 20% piperidine in DMF (100 mL) was added to the resin and the mixture was bubbled with nitrogen gas for thirty minutes at 25° C. The resin was then washed with DMF (100 mL)*5.

(4) Steps 2 and 3 were repeated for the following amino acids elongation: Number #3-15, TABLE 3 below.

(5) After all the steps were completed, the resin was washed with DMF (100 mL)*5, methanol (100 mL)*5, then dried under reduced pressure to make resin-bound peptide Intermediate 28 (CTC resin, 2.0 mmol).

TABLE 3

The list of amino acids and the corresponding reagents used on SPPS.

| # | Materials | Coupling reagents |
|---|---|---|
| 1 | Fmoc-Thr(tBu)-OH (3.00 equivalents) | DIEA (4.00 equiv.) |
| 2 | Fmoc-Cys(Trt)-OH (3.00 equivalents) | HBTU (2.85 equiv.) and DIEA (6.00 equiv.) |
| 3 | Fmoc-Trp-OH (3.00 equivalents) | HBTU (2.85 equiv.) and DIEA (6.00 equiv.) |
| 4 | Fmoc-Val-OH (3.00 equivalents) | HBTU (2.85 equiv.) and DIEA (6.00 equiv.) |
| 5 | Fmoc-Leu-OH (3.00 equivalents) | HBTU (2.85 equiv.) and DIEA (6.00 equiv.) |
| 6 | Fmoc-Glu(OtBu)-OH (3.00 equivalents) | HBTU (2.85 equiv.) and DIEA (6.00 equiv.) |
| 7 | Fmoc-Gly-OH (3.00 equivalents) | HBTU (2.85 equiv.) and DIEA (6.00 equiv.) |
| 8 | Fmoc-Leu-OH (3.00 equivalents) | HBTU (2.85 equiv.) and DIEA (6.00 equiv.) |
| 9 | Building block #1 (2.00 equivalents) | DIC (2.00 equiv.) and HOBt (2.00 equiv.) |
| 10 | Fmoc-Trp-OH (3.00 equivalents) | DIC (3.00 equiv.) and HOBt (3.00 equiv.) |
| 11 | Fmoc-Ala-OH (3.00 equivalents) | DIC (3.00 equiv.) and HOBt (3.00 equiv.) |
| 12 | Fmoc-Cys(Trt)-OH (3.00 equivalents) | DIC (3.00 equiv.) and HOBt (3.00 equiv.) |
| 13 | Fmoc-Asp(OtBu)-OH (3.00 equivalents) | DIC (3.00 equiv.) and HOBt (3.00 equiv.) |
| 14 | AC | $AC_2O$:NMM:DMF = 10:5:85 |
| 15 | Boc-$PEG_2$-OH (3.00 equivalents) | DIC:HOBt:DMAP = 3:3:3 |

Peptide Cleavage and Cyclization.

(1) Cleavage solution (trifluoroacetic acid/TIS/water, 95/2.5/2.5, v/v/v, 500 mL) was added to the flask containing the sidechain protected resin-bound peptide (CTC resin, 5 g, 2.0 mmol) at 25° C. and stirred for two hours.

(2) After filtration, the filtrate was collected.

(3) The filtrate was precipitated with cold isopropyl ether (2.5 L). After filtration, the solid was washed with isopropyl ether (2.5 L) twice, and the crude peptide was dried under reduced pressure for two hours to make Intermediate 29 (3.0 g, crude) as a white solid.

To the mixture of Intermediate 29 (3.0 g, crude) in HOAc/acetonitrile/water (4/3/3, v/v/v, 2 L) was added 0.1 M $I_2$/AcOH dropwise until a yellow color persisted, then the mixture was stirred at 25° C. for five minutes. The mixture was quenched by addition of 0.1 M aqueous $Na_2S203$ dropwise until the yellow color disappeared. After filtration, the filtrate was purified by prep-high performance liquid chromatograph (A: 0.075% trifluoroacetic acid/water, B: acetonitrile), followed by lyophilization to make Intermediate 30 (360 mg, 90.0% purity, 50.8% yield) as a white solid. liquid chromatography-mass spectroscopy: retention time is 0.907-0.960 minutes, MS calculated: $M_{av}$=1833.02, mass observed: $[M+2H]^{2+}$=917.00, $[M+H]^{+}$=1832.91.

Preparation of Intermediate 31

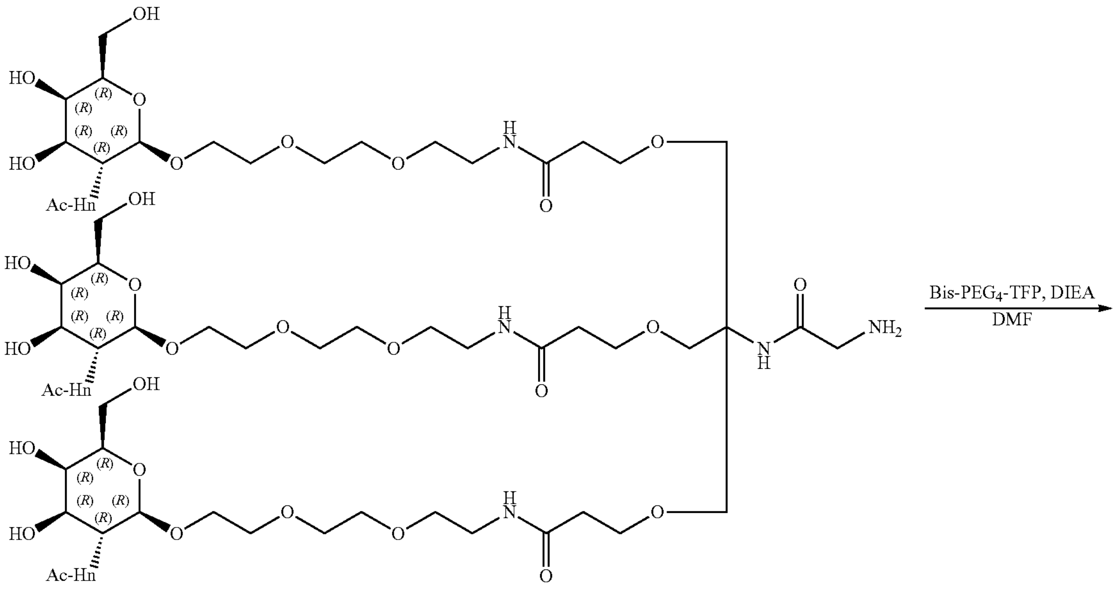

Target A001

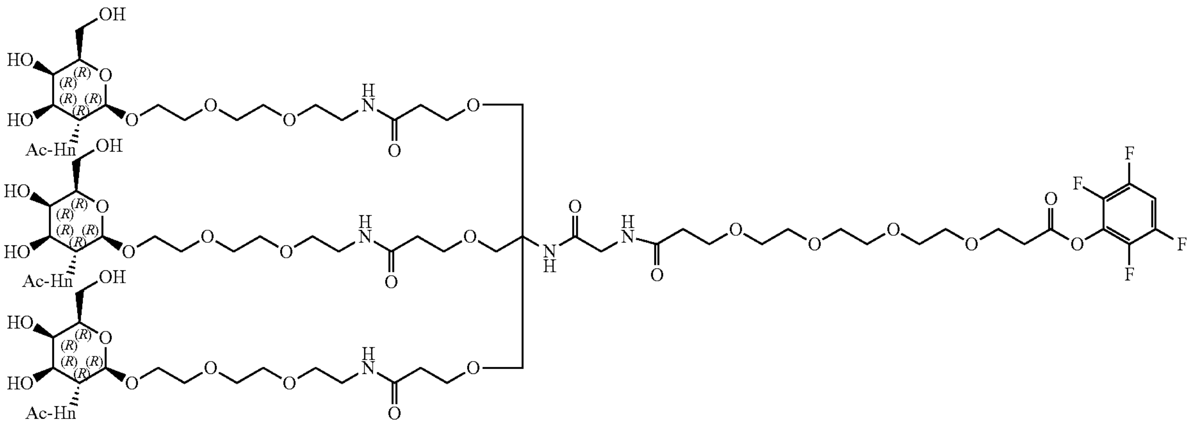

31

To a solution of Bis-PEG4-TFP (2.53 g, 5.00 equivalents) in DMF (25 mL) was added a mixture of Target A001 (1.2 g, 1.00 equivalent) and DIEA (332.9 mg, 449.9 μL, three equivalents) in 10 mL DMF at 0° C. The resulting reaction was stirred for five minutes at 0° C. After completion monitored by liquid chromatography-mass spectroscopy, the mixture was directly injected into the reverse column, purified by prep-high performance liquid chromatography (A: 0.075% trifluoroacetic acid/water, B: acetonitrile), followed by lyophilization to make Intermediate 31 (700 mg, 95.0% purity, 57.5% yield) as colorless oil. liquid chromatography-mass spectroscopy: retention time is 0.709 minutes, MS calculated: $M_{av}$=1821.81, mass observed: $[M+16+3H]^{3+}$=613.10.

Preparation of TBT301:

Harvest and Clarification

Subjected the cell culture fluid to centrifugation at 10000 g for thirty minutes and then pass through a 0.22 μm sterile filter.

Affinity Capture by MabSelect SuRe Resin for ABT301

(1) Purified at room temperature.

(2) Chose the column based on titer, recommended load density (5-10 mg/ml resin).

(3) Equilibrated, five column volumes, with the buffer of 25 mM Tris-HCl, 150 mM sodium chloride, 5 mM EDTA, pH7.5.

(4) Sampled load.

(5) EQ wash. Washed with the buffer of 25 mM Tris-HCl, 150 mM sodium chloride, 5 mM EDTA, pH7.5, for five column volumes.

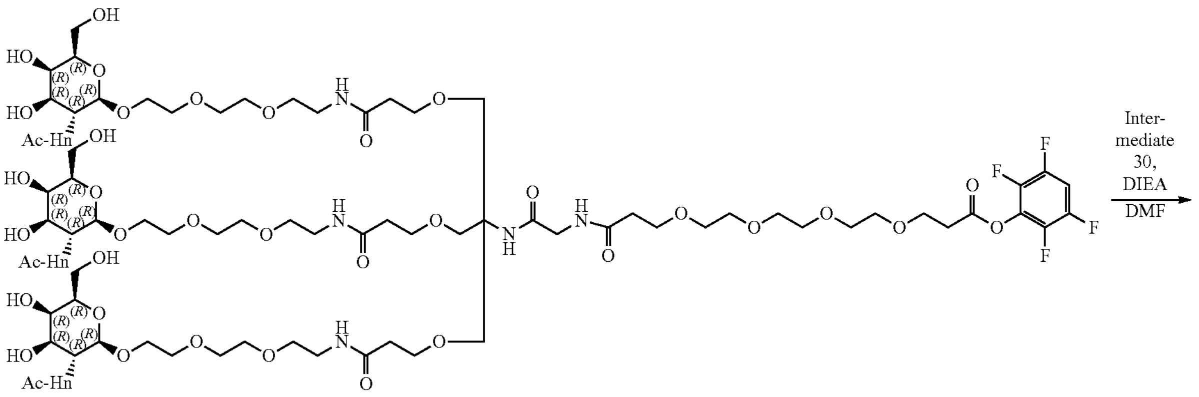

31

BH0003070

To a solution of Intermediate 30 (140.86 mg, 76.85 μmol, 1.00 equivalent) and Intermediate 31 (140 mg, 76.85 μmol, 1.00 equivalent) in DMF (2 mL) was added DIEA (29.80 mg, 230.54 μmol, 40.16 μL, 3.00 equivalents). The mixture was stirred at 20° C. for one hour. After completion monitored by liquid chromatography-mass spectroscopy, the mixture was acidified by 1 M HCl to pH=5. The mixture was purified by prep-high performance liquid chromatography (A: 0.075% trifluoroacetic acid/water, B: acetonitrile) directly. This step was followed by lyophilization to make TBT301 (103 mg, 92.8% purity, 35.6% yield.) as a white solid. liquid chromatography-mass spectroscopy: retention time is 1.391 minutes, MS calculated: $M_{av}$=3488.76, mass observed: $[M+3H]^{3+}$=1163.90.

Example 4

ABT301 Transient Expression (1) The inventors seeded and passaged CHO K1 host cells in advance of performing the assay.

(2) On the day of transfection, the inventors centrifuged host cells to specific cell density for transfection.

(3) Added DNA and transfection reagent (PEI) into host cell for transfection.

(4) Incubated the transfected culture by shaking at 150 rpm.

(5) Shifted temperature from 36.5 degree to 33 degree at 24 hours post transfection.

(6) Performed feeding on day 0 and day 4, then harvested cell culture on day 7 or when VIA<60%.

(6) Triton wash. Washed with the buffer of 25 mM Tris-HCl, 150 mM sodium chloride, 5 mM EDTA, 0.05% Triton 114, 0.05% Triton 100, pH 7.5, for sixty minutes.

(7) EQ wash. Washed with the buffer of 25 mM Tris-HCl, 150 mM sodium chloride, 5 mM EDTA, pH7.5, for ten column volumes.

(8) Eluted with elution buffer 0.1M HAC, for five column volumes (neutralize immediately with neutralization buffer to make a final pH around 5.5).

(9) Tested for affinity chromatography eluates: SDS-PAGE gel non-reducing and reducing, size exclusion chromatography-HPLC.

Size Exclusive Chromatography for ABT301

(1) Purified at room temperature.

(2) Chose the column based on protein amount and molecule weight, e.g., Superdex 200 pg.

(3) Equilibrated with a buffer of phosphate-buffered saline, pH7.4 for ABT301-01, 200 mM Arginine, 137 mM succinic acid, pH 5.0 for ABT301-02 for one column volume.

(4) Sampled load.

(5) Elution with a buffer of phosphate-buffered saline, pH7.4 for ABT301-01, 200 mM Arginine, 137 mM succinic acid, pH 5.0 for ABT301-02 for one column volume.

(6) Collected target protein with desirable purity. Testing for size exclusion chromatography eluates: SDS-PAGE gel nonreducing and reducing, size exclusion chromatography-HPLC.

Buffer Exchange for ABT301

The size exclusion chromatography pool of ABT301-02 was in a buffer containing 200 mM arginine, 137 mM succinic acid, pH 5.0. The sample was then concentrated and dialyzed into a formulation buffer of phosphate-buffered saline at pH 7.4.

Size Exclusion Chromatography-HPLC (1) Perform size exclusion chromatography-HPLC analysis on a Vanquish Flex Duo liquid chromatography instrument using a TSKgel G3000SWxl stainless steel column (7.8×300 mm, particle size 5 μm).

(2) The mobile phase consists of 50 mM sodium phosphate and 300 mM sodium chloride at pH 6.8.

(3) Inject 25 μg of sample per run. Perform isocratic elution for 15 min at a flow rate of 1.0 mL/min. Monitor protein elution by UV absorbance at 280 nm. Integrate the peaks corresponding to aggregates, monomers and LMW species, and calculate the percentage of each species.

SDS-PAGE (1) Perform Non-reducing and reducing SDS-PAGE analysis using precast NuPAGE™ 4-12% Bis-Tris Gel from Thermo Scientific. Sample loading buffer (4×LDS) is from Invitrogen. Gel running buffer (20×MES) is from GenScript.

(2) Treat non-reducing samples with 30 mM iodoacetamide and heat at 95° C. for 5 min before analysis. Treat reducing samples with 50 mM DTT and heat at 95° C. for 5 min before analysis. Carry out electrophoresis at a constant voltage of 180 V for 40 min. Stain gels using Coomassie blue for 30 min and destain with water for one hour.

Endotoxin Level Testing (1) Dilute purified proteins based on maximum valid dilution (MVD) in LAL reagent water (Charles River/W110).

(2) Load samples into Charles River Laboratories EndoSafe LAL Cartridges (Charles River/PTS11F) and detect them using Charles River Laboratories EndoSafe NexGen-MCS™ instrument.

Molecular Mass Analysis by LC-MS (1) Conduct LC-MS analysis by using Agilent 6230 AdvanceBio LC/TOF system with a PL1912-1502, PLRP-S 1000 Å, 2.1×50 mm, 5 μm column (Agilent/PL1912-1502).

(2) For the Non-reduced intact mass analysis, dilute 200 pmol sample by ddH2O, and subject to LC/MS. For the reduced mass analysis, denature and reduce 100 pmol sample using 10 mM Urea (Sigma/15568), 30 mM Tris-HCl (Invitrogen/15568), and DTT (Sigma/D0632) in a total volume of 50 μL. Incubate samples at 37° C. for 20 min and then subjected them to LC/MS.

(3) Analyze the mass spec data using Bioconfirm 10.0 software and identify molecules based on molecular masses.

Example 5

AGN301-001 Report

The composition of matter AGN301-001 is a lysine-based antibody conjugate. The molecule consists of two same single chains covalently linked by disulfide bonds (ABT301, Fc-fusion). The linker payload (TBT301) is conjugated to lysine amines in the antibody. The leaving group will be eliminated when the payload is conjugated to amines. The targeting DAR is 2.

Purification method for antibody conjugate by UF/DF. An ultrafiltration membrane (Pellicon3 0.11m$^2$ Cassette, Ultracel 30 kDa) having a molecular weight of 30 kDa is preferable to concentrate the sample. The UF/DF was pre-processed according to the following procedure:

(1) The inventors assembled the UF/DF system and install the cassette (0.11 m$^2$ membrane area, 30 kDa MWCO).

(2) The inventors flushed the system with water, clean with the 0.1 M sodium hydroxide for thirty minutes, and flush with water again.

(3) The inventors added phosphate-buffered saline, pH 7.4 to the feed tank. Start the feed pump. Verify that the pH and conductivity in the system have been equilibrated to the level of the phosphate-buffered saline.

(4) The inventors added reaction mixture solution to the feed tank. Start the feed pump by partially closing the retentate valve and adjusting the pump speed. Diafilter the product with the phosphate-buffered saline, pH7.4, 10% dimethyl sulfoxide (Sigma-Aldrich, BCCL4606) for 40 DV, followed by phosphate-buffered saline, pH7.4 for 20 DV.

(5) Open the retentate valve fully and collect all the product. Filter the product by 0.22 μm membrane.

(6) Test the quality and concentration of product. Ultraviolet-visible spectroscopy platform by Nanodrop to determine protein concentration of in-process sample and final composition of matter. 750 nm was set up as baseline. The ultraviolet absorption at 280 nm and 220 nm were measured respectively. The calculation method based on Beer-Lambert Law A=E*C*I.

$$A_{280}=E^{mAb}{}_{280}*C_{[mAb]}*I$$

Where E: molar extinction coefficient, C: molar concentration, and I: light path (Nanodrop: 0.1 cm).

DAR determination by liquid chromatography-mass spectroscopy. LC-MS was performed using a combination of Agilent 1260 series high performance liquid chromatography system and time-of-flight mass spectrometry. DAR was calculated based on the peak abundance of the deconvoluted Mass.

(1) Preparation of sample used in liquid chromatography-mass spectroscopy analysis (deglycosylation)

(a) Denaturation. Transfer sample into 1.5 ml tube and incubate at 75° C. for five minutes.

(b) Deglycosylation. Transfer 15 μg of denatured samples into a 1.5 ml tube, add 3 μL Rapid PNGase F (non-reducing format, 5×) enzyme buffer and 0.5 μL Rapid PNGase F (non-reducing format) enzyme for de-glycosylation and some water to ensuring the total volume is 15 μL, then incubate this solution at 50° C. for fifteen minutes. The obtained sample was used in a liquid chromatography-mass spectroscopy analysis.

A high performance liquid chromatography analysis was carried out under the following measurement conditions.

TABLE 4

Liquid chromatography parameters for DAR determination

| | | |
|---|---|---|
| Equipment | HPLC Agilent 1260 | |
| Column | Agilent PLRP-S, 50 × 2.1 mm, 8 μm, 1000 Å | |
| Detection wavelength | 280 nm, 214 nm | |
| Column oven temperature | 80° C. | |
| Sampler temperature | 2~8° C. | |
| Flow rate | 0.5 mL/min | |
| Injection amount: | 2 μg | |
| Mobile phases | A: 0.025% trifluoroacetic acid + 0.1% FA in water. B: 0.025% trifluoroacetic acid + 0.1% FA in acetonitrile | |
| Gradient program | Ten minutes | |
| | Time (minutes) | B (%) |
| Gradient | 0.0 | 25 |
| | 0.7 | 34 |
| | 5 | 45 |
| | 6 | 90 |

TABLE 4-continued

| Liquid chromatography parameters for DAR determination | |
|---|---|
| 7 | 90 |
| 7.1 | 25 |
| 10.0 | 25 |

TABLE 5

| Time-of-flight (TOF) parameters for DAR determination | |
|---|---|
| Equipment | Agilent 6224TOF |
| Polarity | positive |
| Gas Temp. | 350° C. |
| Drying Gas | 13 L/min |
| Nebulizer | 45 psig |
| VCap | 5000 V |
| Fragmentor | 250 V |
| Mass Range | 500-8000 m/z |
| Acquisition Rate | 1 spectra/s |

Aggregation determination by size exclusion chromatography-high performance liquid chromatograph. Size-exclusion chromatography was performed using an Agilent 1260 series HPLC system with the TSK gel G3000SWXL Size-exclusion chromatography column (7.8×300 mm, 5 μm) at 25° C. The mobile phase was consisted of 78 mM $KH_2PO_4$, 122 mM $K_2HPO_4$, 250 mM potassium chloride, 15% isopropanol at pH 7.0±0.1. The flow rate was set at 0.75 ml/min. Sample loading was 40~50 μg per injection. Samples were detected at 280 nm and 370 nm with a UV detector. The retention time of the aggregation peak was recorded based on its relative molecular weight. And the aggregation level was determined by the relative area of the peak at 280 nm.

Residual free drug determined by reverse phase-UPLC. The residual free drug level was determined by reverse phase UPLC. After protein precipitation, supernatant was loaded to Luna Omega 1.6 μm Polar C18 100 Å column and eluted by a gradient of increasing the organic mobile phase. The percentage of residual free drug was quantified via peak area by comparing it to external standard curve.

Solvent Preparation:

Solvent I (for protein precipitation): Weighed 10 g NaCl to the pre-mixed organic solvent of 30 mL methanol and 50 mL acetonitrile, mixed and stirred one hour at least, allowed the solution to stand for at least one hour before use. The supernatant was the saturated sodium chloride solution.

Dilution Buffer I. Mix 250 μL of dimethyl sulfoxide, 700 μL of phosphate-buffered saline, 1000 μL of 6 mg/mL Herceptin® in phosphate-buffered saline as Buffer I.

Dilution Buffer II. Mix 300 μL of dimethyl sulfoxide, 700 μL of phosphate-buffered saline, 1000 μL of 6 mg/ml Herceptin® in phosphate-buffered saline as Buffer II.

Preparation of standard curve (uABT (cpd1724)/linker payload (TBT301)). The stock standard uABT (cpd1724)/linker payload (TBT301) solution was firstly diluted to 1000 UM with DMSO for standard curve preparation. Add 10 μL of the 1000 μM uABT to 390 μL of dilution buffer I for a final concentration of 25 μM. Then the standard curve and sample were prepared. Take 160 μl of each standard samples and add 240 μl solvent buffer I as final standard curve (10 μM, 5 μM, 2 μM, 1 μM, 0.5 μM, 0.2 μM, 0.1 μM). Vortex solution for ten minutes at room temperature. Centrifuge solution for ten minutes at 16,000 rcf at room temperature. Remove the supernatant immediately into a glass vial for analysis.

Preparation of sample. The inventors added phosphate-buffered saline and dimethyl sulfoxide (Sigma-Aldrich, BCCL4606) to sample to 6 mg/ml with 15% (v/v) dimethyl sulfoxide. Then they mixed 30 μL 6 mg/ml sample with 45 μl Solvent I (sample: precipitant 1:1.5v/v). Vortex solution for ten minutes at room temperature. Centrifuge solution for ten minutes at 16,000 rcf at room temperature. Remove the supernatant immediately into a glass vial for analysis.

TABLE 6

| Reverse phase-high performance liquid chromatography parameters for free drug determination | | |
|---|---|---|
| Column: | Luna Omega 1.6 μm polar C18 100 Å | |
| Detection Wavelength: | 220 nm | |
| Column Oven Temperature: | 30° C. | |
| Sampler Temperature: | 2~8° C. | |
| Flow Rate: | 0.4 mL/minute | |
| Injection Volume: | 40 μL | |
| Mobile Phases: | A: 0.1% trifluoroacetic acid in water. B: 0.1% trifluoroacetic acid in acetonitrile | |
| Gradient Program | Forty minutes | |
| | Time (minutes) | B (%) |
| Gradient | 0.00 | 2.00 |
| | 32.00 | 50.00 |
| | 32.01 | 90.00 |
| | 35.00 | 90.00 |
| | 37.01 | 2.00 |
| | 40.00 | 2.00 |

Data Analysis (Linker Payload)

Integrated the stand DAR curve injections. Plotted the peak area (Y) as a function of concentration (X), Y=Kx+b. Calculated the slope (k) and intercept (b).

Integrated the related drug peak in the sample. Recorded the sum peak area (Y) and interpolated against the standard curve. Calculated the concentration obtained.

Where $C_{linker\ payload}$=concentration of linker payload by C18-UPLC, Y=sum peak areas of drug related impurities, k=slope of standard curve, and b=intercept of standard curve.

Where: $C_{linker\ payload}$=concentration of linker payload by C18-UPLC (mg/ml), $C_{protein}$=concentration of protein (mg/mL), DAR=drug to antibody ratio by liquid chromatography-mass spectroscopy, $Mw_{Linker\ payload}$=molecular weight of drug, and $Mw_{protein}$=molecular weight of monoclonal antibody.

Data Analysis (uABT):

Integrated the standard DAR curve injections. Plotted the peak area (Y) as a function of concentration (X), Y=Kx+b. Calculated the slope (k) and intercept (b).

Integrated the related drug peak in the sample. Recorded the sum peak area (Y) and interpolated against the standard curve. Calculated the concentration obtained.

Where $C_{uABT}$=concentration of uABT by C18-UPLC, Y=sum peak areas of drug related impurities, k=slope of standard curve, and b=intercept of standard curve.

Where $C_{uABT}$=concentration of uABT by C18-UPLC (mg/mL), $C_{protein}$=concentration of protein (mg/mL), DAR=drug to antibody ratio by liquid chromatography-mass spectroscopy, $Mw_{uABT}$=molecular weight of uABT, and $Mw_{protein}$=molecular weight of monoclonal antibody.

Residual Payload Determination by Reverse Phase-UPLC.

The residual free drug level was determined by reverse phase UPLC. After protein precipitation, supernatant was loaded to Luna Omega 1.6 μm Polar C18 100 Å column and eluted by a gradient of increasing the organic mobile phase.

The percentage of residual free drug was quantified via peak area by comparing it to external standard curve.

Preparation of standard curve (payload cpd1777). The stock standard payload cpd1777 solution was firstly diluted to 1000 μM with formulation buffer for standard curve preparation. Add 10 μl of the 1000 μM payload cpd1777 to 90 μL of solvent II for a final concentration of 100 μM. Then the standard curve and sample were prepared. Vortex solution for ten minutes at room temperature. Centrifuge solution for ten minutes at 16,000 rcf at room temperature. Remove the supernatant immediately into a glass vial for analysis.

TABLE 7

Payload cpd1777 dilution table

| Sample name | Stock sample name | V stock (μL) | V Dilution buffer (μL) | V Total (μL) | V final (μL) |
|---|---|---|---|---|---|
| STD_10 μM | STD_100 μM | 30 | 270 | 300 | 120 |
| STD_5 μM | STD_10 μM | 180 | 180 | 360 | 240 |
| STD_2 μM | STD_5 μM | 120 | 180 | 300 | 90 |
| STD_1 μM | STD_2 μM | 180 | 180 | 360 | 180 |
| STD_0.75 μM | STD_2 μM | 30 | 50 | 80 | 80 |
| STD_0.5 μM | STD_1 μM | 180 | 180 | 360 | 360 |
| STD_0.2 μM | STD_0.5 μM | 120 | 180 | 300 | 300 |

Preparation of sample. Mix 30 μL sample with 60 μl Solvent I (sample: precipitant 1:2 v/v). Vortex solution for ten minutes at room temperature. Centrifuge solution for ten minutes at 16,000 rcf at room temperature. Remove the supernatant immediately into a glass vial for analysis.

TABLE 8

Reverse phase- high performance liquid chromatography parameters for free drug determination

| | | |
|---|---|---|
| Column: | Luna Omega 1.6 μm Polar C18 100 Å | |
| Detection Wavelength: | 196 nm | |
| Column Oven Temperature: | 30° C. | |
| Sampler Temperature: | 2~8° C. | |
| Flow Rate: | 0.4 mL/minute | |
| Injection Volume: | 40 μL | |
| Mobile Phases: | A: 0.1% trifluoroacetic acid in water. B: 0.1% trifluoroacetic acid in acetonitrile | |
| Gradient Program | 28 minutes | |
| | Time (minutes) | B (%) |
| Gradient | 0.00 | 5.00 |
| | 20.00 | 35.00 |
| | 20.01 | 90.00 |
| | 23.00 | 90.00 |
| | 23.01 | 5.00 |
| | 28.00 | 5.00 |

Data Analysis.

Integrated the standard DAR curve injections. Plotted the peak area (Y) as a function of concentration (X), Y=Kx+b. Calculated the slope (k) and intercept (b).

Integrated the related drug peak in the sample. Recorded the sum peak area (Y) and interpolated against the standard curve. Calculated the concentration obtained.

Where $C_{payload}$=concentration of payload by C18-UPLC, Y=sum peak areas of drug related impurities, k=slope of standard curve, and b=intercept of standard curve.

Report the relative amount of residual payload in antibody conjugate composition of matter (% mol/mol) with two decimal place.

Where $C_{payload}$=concentration of payload by C18-UPLC (mg/mL), $C_{protein}$=concentration of protein (mg/mL), DAR=drug to antibody ratio by liquid chromatography-mass spectroscopy, $MW_{payload}$=molecular weight of payload, and $MW_{protein}$=molecular weight of monoclonal antibody.

Hydrophobicity determination by hydrophobic interaction chromatography-high performance liquid chromatography. Hydrophobic interaction chromatography was performed using an Agilent 1260 series HPLC system with the TSK gel Butyl-NPR Hydrophobic Interaction chromatography column (4.6×35 mm, 5 μm) at 25° C. The mobile phase A was consisted of 1.5 M $(NH_4)_2SO_4$ and 50 mM $K_2HPO_4 \cdot 3H_2O$, at pH 7.2±0.2, Cond. 190,000±200 us/cm. The mobile phase B was consisted of 50 mM Potassium Phosphate and 25% 2-propanol, at pH 7.4±0.2, Cond. 3400±200 us/cm. The flow rate was set at 0.6 mL/min. Sample loading was 8 μl per injection. Samples were detected at 280 nm with an ultraviolet light detector.

TABLE 9

Hydrophobic interaction chromatography-high performance liquid chromatography parameters

| | | | |
|---|---|---|---|
| Column | TOSOH, TSKgel Butyl-NPR, 2.5 μm, 4.6 * 35 mm | | |
| Detection | 280 nm BW 4 | | |
| Column Oven Temp.: | 25° C. | | |
| Sampler Temp.: | 6 ± 2° C. | | |
| Flow Rate: | 0.6 mL/minute | | |
| Stop Time: | 20 minutes | | |
| Maximum Pressure: | 300 bar | | |
| Injection Amount: | 8 μL | | |
| Mobile Phases: | Mobile Phase A: 1.5M $(NH_4)_2SO_4$ and 50 mM $K_2HPO_4 \cdot 3H_2O$. Mobile Phase B: 50 mM potassium phosphate and 25% 2-propanol | | |
| | Time (minutes) | A (%) | B (%) |
| Gradient Program: | 0 | 100 | 0 |
| | 2 | 100 | 0 |
| | 15 | 0 | 100 |
| | 16 | 0 | 100 |
| | 17 | 100 | 0 |
| | 20 | 100 | 0 |

Endotoxin determination: The endotoxin level was determined by kinetic turbidimetric assay.

Preparation of endotoxin standards and quality control: The Control Standard Endotoxin (CSE)(10 EU/vial, lyophilized was reconstituted with 1 ml of water for BET to yield a 10 EU/mL standard solution. Made ten-fold dilution using the water for BET, prepare standard solutions with four concentrations (S1_10 EU/mL, S2_1 EU/mL, S3_0.1 EU/mL, S4_0.01 EU/mL). Diluted CSE with water for BET to prepare quality control (0.05 EU/mL).

Preparation of Tachypleus Amebocyte Lysate (TAL) reagents: The TAL reagent is stable when stored at 2~8° C.

before expiration. Allow reagents to equilibrate to room temperature before use. Added 1.25 mL Water for BET to dissolve one bottle of TAL reagent.

Preparation of Samples: The inventors diluted all the sample X/2 folds with water for BET. Taken half volume of X/2 folds sample and added equal volume of water for BET to make the finally tested sample with X folds dilution. Added equal volume of S3 in the remaining half of volume of X/2 folds sample to make its PPC sample with endotoxin concentration to quality control.

Add 100 μL of the standard curve, quality control, sample, PPC and NTC into wells. Add 100 μl of TAL reagent into the 96-well plat wells (Greiner-655185). All standards control and samples need duplicate. Read microplate with a plate reader.

$OD_{405}$ nm was read during incubating at 37° C. for one hundred minutes in a microplate reader.

A standard curve was prepared by plotting the average 405 nm measurement for each standard compared to its endotoxin level in EU/mL.

Standard curve was used to determine the endotoxin level of samples.

Conjugation Buffer and Formulation Buffer.

(1) ABT301 in original buffer (phosphate-buffered saline, pH7.4) was buffer exchanged to 20 mM phosphate-buffered saline, pH 6.5 by Amicon® Ultra Centrifugal Filter Unit. Concentration was tested with 10.71 mg/mL by Nanodrop.

(2) 77 mg of antibody was transferred to 50 ml tube (Greiner, GN227270) and placed in ice bath; then added with conjugation buffer (20 mM PB, pH 6.5) and 10 mM TBT301 solution (4.77 equivalents). The total dimethyl sulfoxide concentration in the reaction mixture was 3.05%; the concentration of the reaction is 10 mg/mL. The reaction vessel was allowed to approach ambient temperature and then incubated at 25° C. for twenty-four hours.

(3) The crude conjugation was purified with UF/DF (Pellicon 3, 30 kDa, 0.11 $m^2$) with phosphate-buffered saline, pH7.4 (Gibco, 10010031), 10% dimethyl sulfoxide (Sigma, D4540) for 40 DV, followed by phosphate-buffered saline, pH7.4 for 20 DV.

(4) The purified sample was filtered with 0.22 μm filter.

(5) Performed the quality control tests including concentration, size exclusion chromatography-high performance liquid chromatography, hydrophobic interaction chromatography-high performance liquid chromatography, liquid chromatography-mass spectroscopy, and endotoxin level.

Results of Bulk Conjugation.

After conjugation, the reaction mixture was purified with UF/DF (Pellicon 3, 30 kDa, 0.11m2) with phosphate-buffered saline, pH 7.4 (Gibco, 10010031) contain 10% dimethyl sulfoxide (Sigma-Aldrich) for 40 DV and followed by phosphate-buffered saline, pH7.4 for 20 DV. Then filter with 0.22 μM membrane.

Reaction conditions and results for AGN301-001 bulk conjugation. TBT301 to ABT301 ratio was 4. Conjugation Concentration was 10 mg/mL. Conjugation temperature and time was 4-25° C. for twenty-four hours. Theoretical mass was 109683.17 Da. Measured mass was 109700.63 Da Amount was 54.71 mg. MS-DAR was 2.00 Size exclusion chromatography-purity was 97.44% Yield was 71.06%.

TABLE 10

| Equipment list | |
|---|---|
| Equipment name | Equipment information |
| High performance liquid chromatography | Agilent Technologies, HPLC 1260 |

TABLE 10-continued

| Equipment list | |
|---|---|
| Equipment name | Equipment information |
| Liquid chromatography-mass spectroscopy | Agilent Technologies, HPLC 1260/6224 TOF |
| Liquid chromatography-mass spectroscopy | Agilent Technologies, HPLC 1290/6530 QTOF |
| Nanodrop 2000 | Thermo Scientific, 1294881 |
| Pure water generator | Milli-Q Reference |

TABLE 11

| Material list | |
|---|---|
| Material name | Material information |
| Column for liquid chromatography-mass spectroscopy | Agilent Technologies, PLRP-S, 1000 A 8 μm 50*2.1 mm, PL1912-1802 |
| Size exclusion chromatography column | TOSOH, TSKgel G3000SWXL, 7.8 × 300 mm, 5 μm, 08541 |
| C18 column | Agilent Technologies, InfinityLab Poroshell 120 SB-C18, 4.6 × 100 mm, 2.7 μm, 685975-902 |
| Hydrophobic interaction chromatography column | TOSOH, TSKgel Butyl-NPR, 2.5 μm, 4.6 * 35 mm |
| Free drug column | Luna Omega 1.6 μm Polar C18 100 Å |
| Millex-GP Syringe Filter Unit, 0.22 μm | Millipore-SLGPR33RB |
| Acetonitrile | Merck, Supelco-1.00030.4008 |
| phosphate-buffered saline, pH 7.4 | Gibco, 10010031 |
| Trifluoroacetic acid | jkchemical-134753 |
| $Na_2HPO_4$•$7H_2O$ | Sigma-S2429-500G |
| $NaH_2PO_4$ | Sigma-S5011-500G |
| $(NH_4)_2SO_4$ | Sigma-A4418-1KG |
| 2-propanol | Sigma-34863 |
| Sodium Chloride | Domestic |
| UF/DF cassette | Pellicon3 0.11 $m^2$ Cassette, Ultracel 10 kDa |
| $K_2HPO_4$ | SIGMA/P5655 |
| $KH_2PO_4$•$3H_2O$ | SIGMA/900170 |
| Methanol | Merck, 106007 |
| L-histidine | Merck/1.04352.1000 |
| L-histidine HCl | Avantor-4942-06 |
| Sucrose | PFANSTIEHL/S-124-1-MC |

Example 6

Surface Plasmon Resonance Binding Experiments

Binding confirmation by surface plasmon resonance. Surface plasmon resonance (SPR) assays were performed on a Cytiva Biacore S200 and Cytiva Biacore 8k+ instrument. Anti-TSHR M22 monoclonal antibody was diluted in 10 mM sodium acetate buffer pH 4.5 to 10 μg/mL. The antibody ligand was immobilized to the surface of a CM5 chip via amine-coupling, targeting 300 RU. AGN301 was prepared in HBS-P running buffer in concentrations ranging from 1-1000 nM. AGN301 was then injected over M22 antibody as analyte using Single-cycle kinetics method. As analyte is flowed in solution over an immobilized ligand, binding events between analyte and ligand induce a change in the refractive index proportional to bound mass. Data were analyzed using the Biacore Insight Evaluation Software to determine binding affinity.

AGN301 binds to M22 by SPR ($K_D$ ~100 nM), similar to unfunctionalized LRD-Fc-fusion (ABT301, $K_D$ ~265 nM). SPR results for AGN301 was $K_D$=123±2.8 nM.

AGN301 binds to human TSH in the SPR binding assay with less affinity to than to autoantibody M22. In this SPR assay setup, AGN301 is immobilized as a ligand to the surface of a CM5 chip via amine-coupling and human TSH or anti-TSHR antibody M22 are flowed over as analyte. For human TSH $K_D$: 497±118 nM. For M22 (positive control), $K_D$: 11.2±0.5 nM.

Figure 5A:
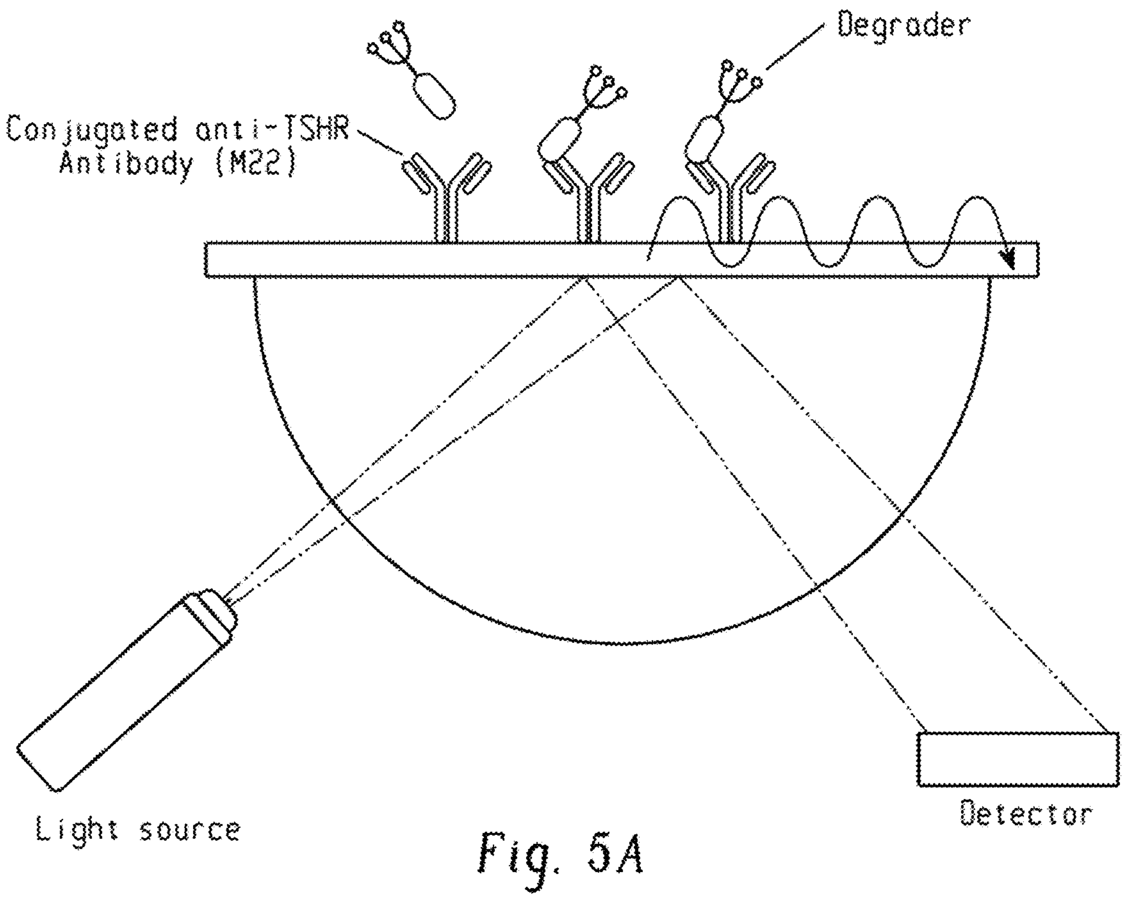
FIG. 5A schematically shows binding of the molecular degrader according to an embodiment of the present invention to anti-TSHR antibody M22 in the SPR assay.

FIG. 5A schematically shows binding of the molecular degrader according to an embodiment of the present invention to an immobilized anti-TSHR antibody M22 in the SPR assay.

Figure 5B:
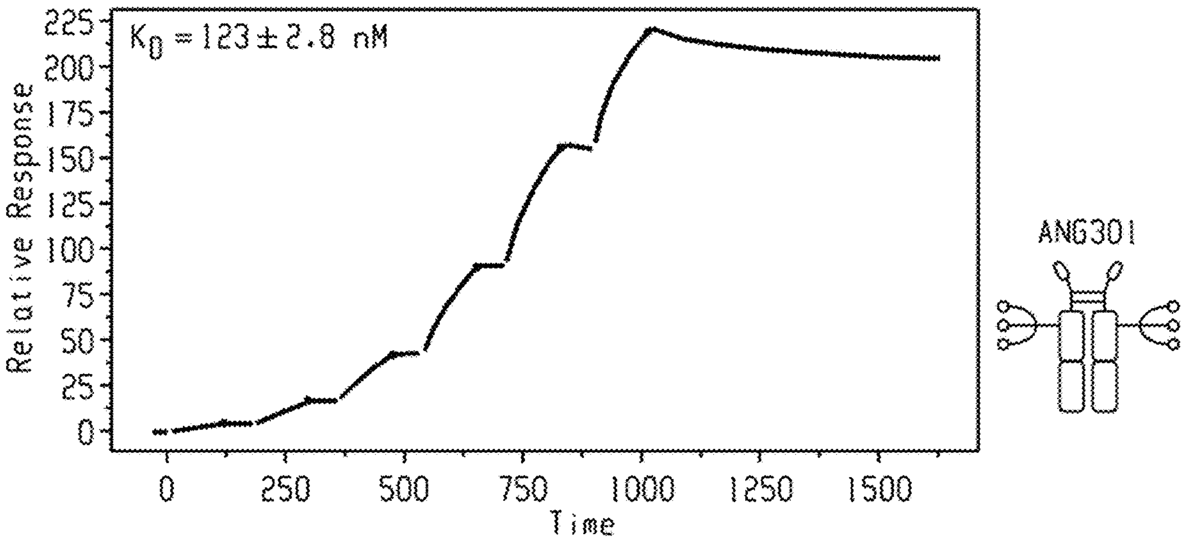
FIG. 5B illustrates the results of AGN301 binding to patient-derived anti-TSHR antibody M22 in the SPR assay.

FIG. 5B illustrates the results of AGN301 binding to patient-derived anti-TSHR antibody M22 in the SPR assay.

Conclusion: Degraders bind to patient-derived anti-TSHR antibody M22 by surface plasmon resonance.

Example 7

Ternary complex formation assay. The ability of degraders to induce a ternary complex between anti-TSHR M22 antibody and ASGPR was evaluated using a TR-FRET assay. 12.5 nM anti-TSHR mouse M22 antibody was mixed with 50 nM biotinylated ASGPR CRD along with dilutions of degraders and their unconjugated bait counterparts. After incubating mixture, a HTRF fluorophore pair comprising of 15 nM pAb anti-mouse IgG d2-conjugate (Revvity) and 2.5 nM streptavidin-europium cryptate conjugate (Revvity) were added. The FRET ratio was read using an Envision plate reader and data were analyzed using GraphPad Prism 10. $EC_{50}$ reported correspond to complex formation.

AGN301 $EC_{50}$=0.01 nM.

Degraders AGN301 and Compound A mediate dose-dependent ternary complex between ASGPR and anti-TSHR (M22) whereas their unconjugated bait counterparts do not.

Degraders AGN301 and Compound A induce ternary complex between ASGPR and anti-TSHR antibody whereas their unconjugated bait counterparts do not.

Figure 6A:
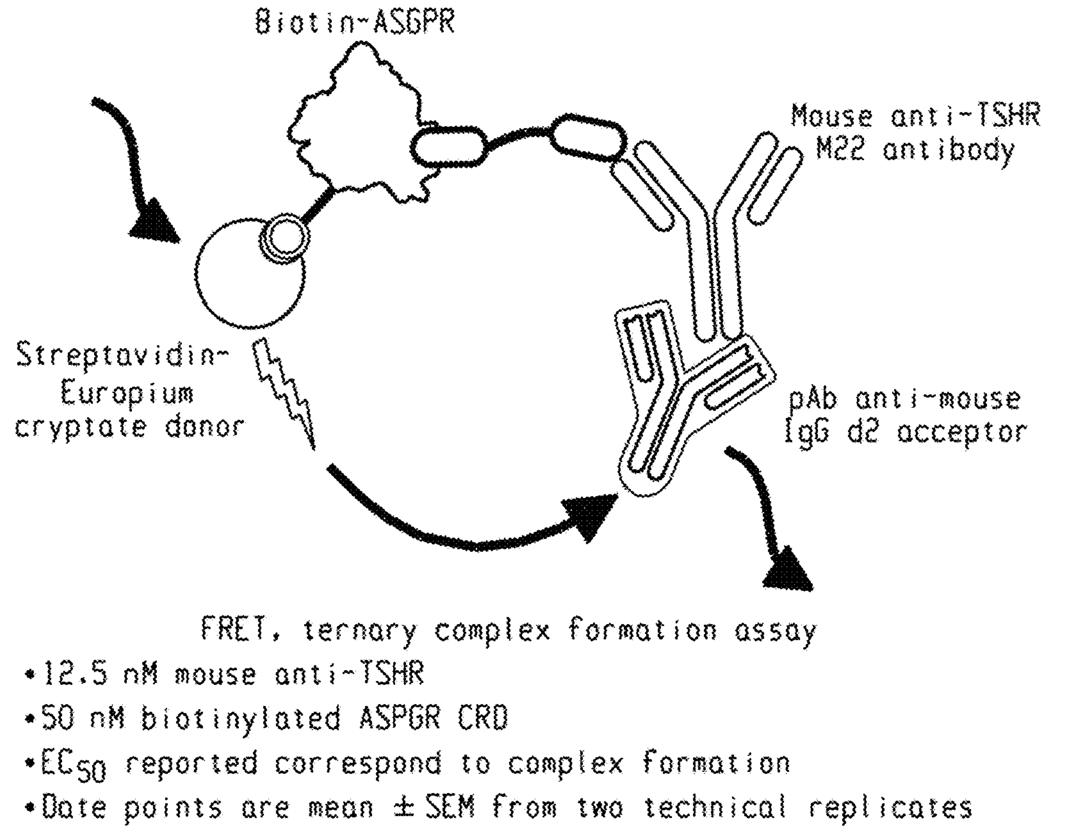
FIG. 6A is a diagram schematically showing formation of a ternary complex in the TR-FRET assay.

FIG. 6A is a diagram schematically showing formation of a ternary complex in the TR-FRET assay.

Figure 6B:
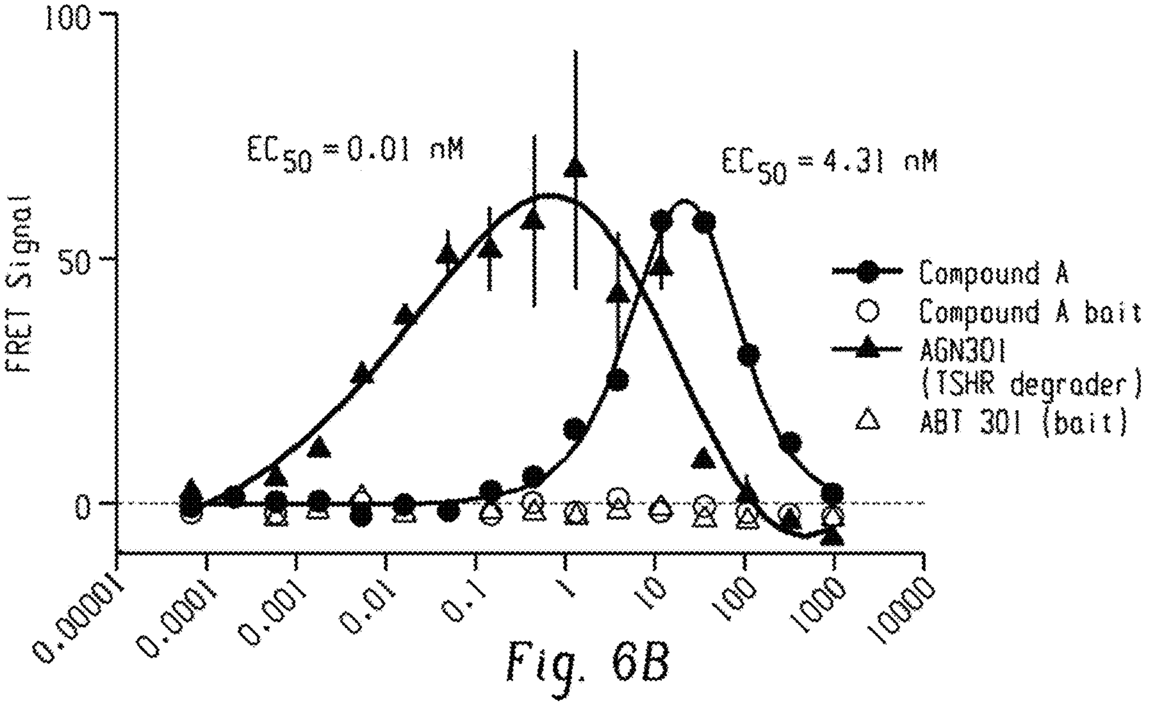
FIG. 6B shows formation of the ternary complex between ASGPR and anti-TSHR antibody M22 for TSHR degrader AGN301 in the TR-FRET assay.

FIG. 6B shows formation of the ternary complex between ASGPR and M22 for TSHR degrader AGN301 in the TR-FRET assay.

Example 8

Meso Scale Discovery (MSD)

Immobilized protein bait is a leucine-rich domain (LRD) protein bait (Fc-fusion), ABT301 (Compounds 7147) or an LRD bait without Fc, ABT302 (Compound 7150).

Detected: IgG (% depletion).

TSHR-LRD protein baits capture IgG from patient samples.

Anti-TSHR status determined by clinical-grade ELISA using a TSHR-LRD protein bait.

LRD protein bait (ABT302, SEQ ID NO: 6) selectively engages patient IgG by competitive MSD.

Binding of serum IgG to a TSHR-LRD bait (ABT301, Fc-fusion) is effectively competed in Graves' patient samples but not in control.

Figure 7:
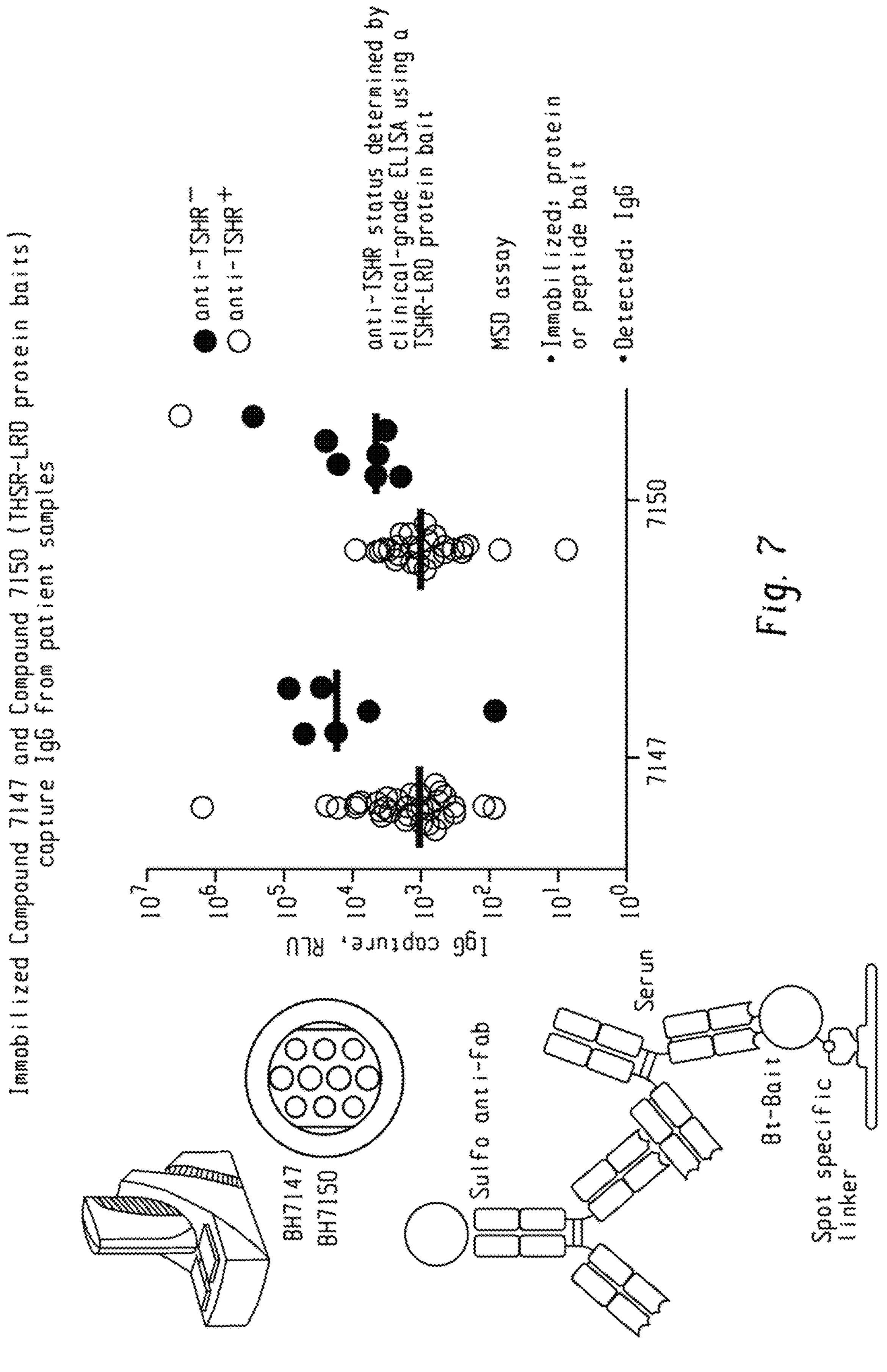
FIG. 7 illustrates capture of IgG from patient samples by THSR-LRD protein baits ABT301 (Compound 7147 and Compound 7150) according to an embodiment of the present invention.

FIG. 7 illustrates capture of IgG from patient samples by THSR-LRD protein baits ABT301 (Compounds 7147) and ABT302 (Compound 7150) according to an embodiment of the present invention.

Figure 8:
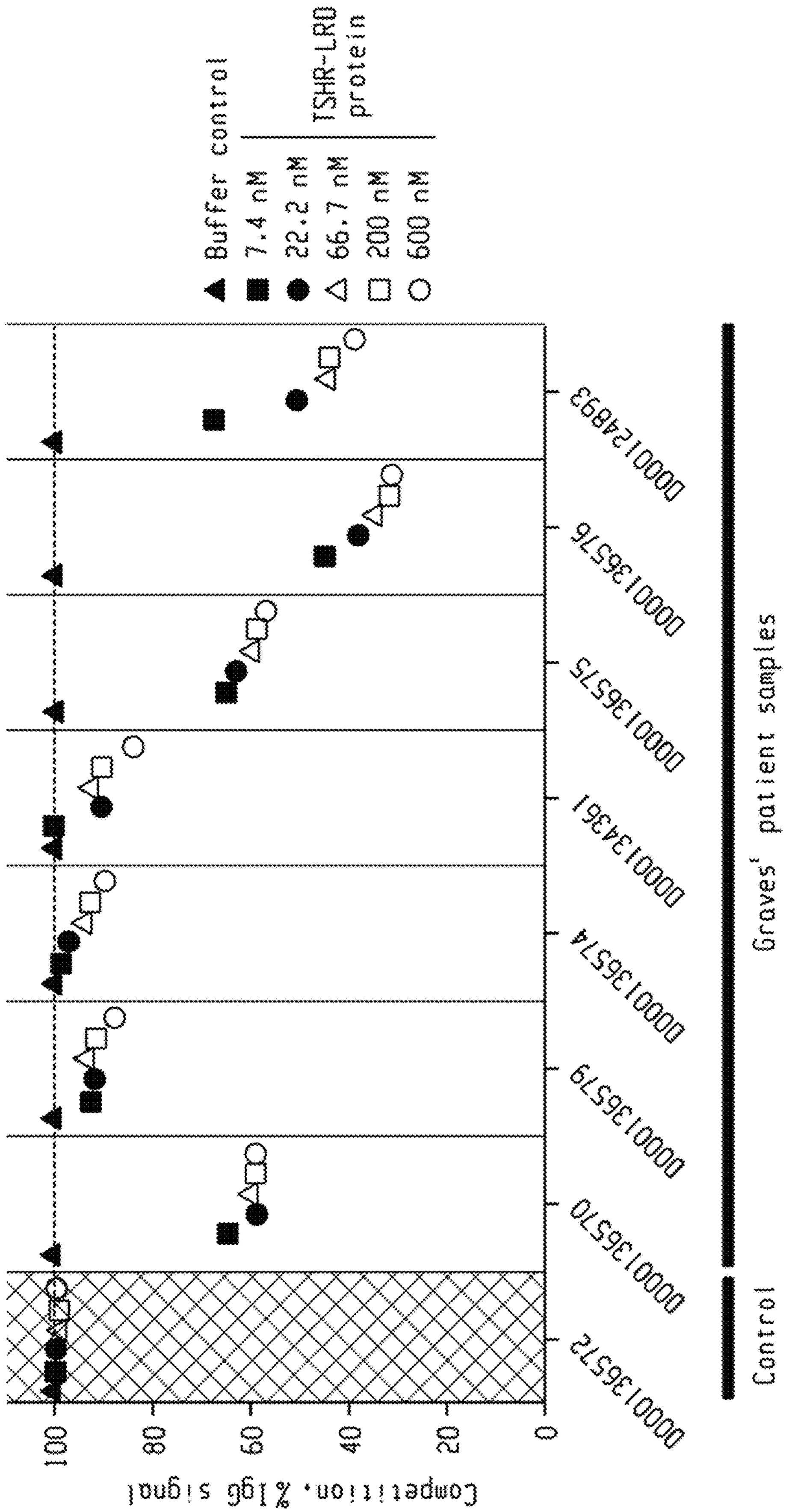
FIG. 8 is a diagram showing that the LRD protein bait selectively engages patient IgG by competitive MSD.
Figure 8:
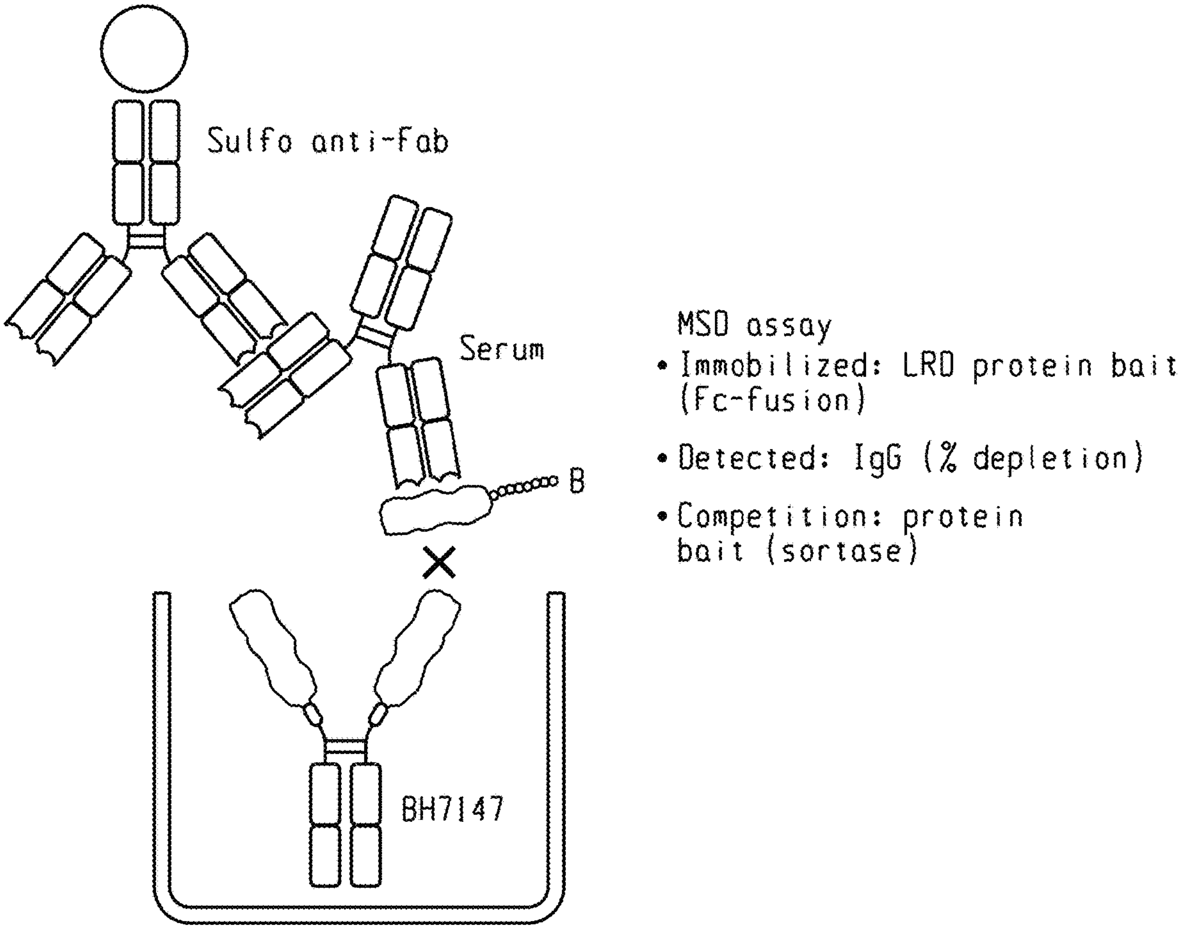

FIG. 8 is a diagram showing that the LRD protein bait selectively engages patient IgG by competitive MSD.

Example 9 cAMP Conditioned Media Assay

The inventors developed a successful cAMP functional assay using conditioned media post-endocytosis. Compounds+M22 antibody was added first to HEK293-ASGPR1 cell line. Twenty-four hour-conditioned media was applied to CHOK1-TSHR cell line. A CAMP-Glo Max assay (Promega) was used to measure TSHR stimulation by M22. Compounds representing the LRD-bait successfully functioned as decoys in this cAMP functional assay.

Cyclic AMP concentration in lysates can be assayed using Direct CAMP ELISA kits (Enzo Life Sciences, Exeter, UK). See Miller-Gallacher et al., Journal of Molecular Endocrinology, 62, 117-128 (2019).

Example 10

Endocytosis Cellular Assay

ASGPR-dependent uptake assay. An on-mechanism endocytosis assay that indirectly measures the ternary complex formed by a fluorescently labeled tool anti-TSHR antibody (M22), a degrader compound, and ASGPR, and directly measures degrader-dependent antibody internalization in HEK293 cells.

HEK293-ASGPR-mediated endocytosis assay methods. HEK293-ASGPR1 cell line cells were cultured in DMEM media containing 10% HI-Fetal Bovine Serum, 1% penicillin/streptomycin, and 200 μg/ml G418 (complete HEK293 media) maintaining a density at or below 90% confluency. Cells were harvested by washing twice with phosphate-buffered saline followed by detachment with Accutase. Cells were strained with a 40 μm strainer into a fresh centrifuge tube then centrifuged for five minutes at 500×g. Supernatant was poured off and the pellet was resuspended in fresh complete HEK293 media. Viable cell density was measured using a Countess II cell counter and trypan blue dye. Viable cells were diluted with complete HEK293 media with 2 μg/mL PDL to a concentration $3.0\times10^5$ cells/mL to achieve $3.0\times10^4$ cells/well in a 96-well assay plate. Assay plate was incubated overnight 37° C. and 5% $CO_2$ to allow for cell attachment and monolayer establishment.

The next day, M22 antibody was labeled with Alexa Fluor 647 using an Alexa Fluor antibody labeling kit to make M22 directly conjugated to AlexaFluor-647. Alternatively, LysoLight-Deep Red (LLDR, Invitrogen) can be used as the fluorophore. LysoLight-Deep Red dye visible after cleavage with cathepsin B (Thermo L36004). Briefly, M22 antibody was buffer exchanged into phosphate-buffered saline using a Zeba desalting column. The concentration of the antibody was verified using a Nanodrop and 100 μg was mixed with 0.1 volumes 1M sodium bicarbonate provided in the kit and added to a vial of reactive AF-647 dye. The reaction was allowed to incubate for one hour in the dark. Following conjugation, residual unreacted dye was removed through a Zeba desalting column and the final product was measured for IgG and AF-647 concentration via Nanodrop.

A 2.2 nM solution of M22-647 was prepared in OptiMEM for the HEK293 endocytosis assay. AGN301 was serial diluted in OptiMEM with a starting concentration of 20 nM down to 30 μM in 3-fold increments to create a 10× dilution series for dosing. A 0 μM compound control was also included as a vehicle control for each compound. The assay plate containing cells was removed from the incubator and media was gently removed by aspiration. 90 μl of 2.2 nM M22-647 was added to each well of the assay plate. Ten μl of the AGN301 dilution series or vehicle control was added to select wells in duplicate allowing for a 2 nM final concentration of M22-647. The final concentration of AGN301 from 2 nM to 3 μM with a 0 nM vehicle control.

The assay plate was incubated at 37° C. and 5% $CO_2$ in the Incucyte instrument, collecting three phase and near-IR (NIR) images per well for twenty-four hours post AGN301 dosing. Incucyte analysis software was used to process individual images and subtract background fluorescent signal. For each independent experiment, the total area of NIR signal ($\mu m^2$/image) per well was measured from two replicate wells and concentration response curves were analyzed in GraphPad Prism 10. Peak fluorescent area and $EC_{50}$ values were determined by fitting the data to a four-parameter non-linear regression model.

The results for [Ligand]<34 nM were fitted to obtain an $EC_{50}$. Data points were mean±SEM from two technical replicates. Peak fluorescent area follows the 100 nM AGN301 dose over time.

There was successful cellular internalization of a patient-derived monoclonal anti-TSHR antibody M22 with lead degraders. The degraders mediate uptake of patient-derived anti-TSHR (M22) into ASGPR-expressing cells.

Figure 9:
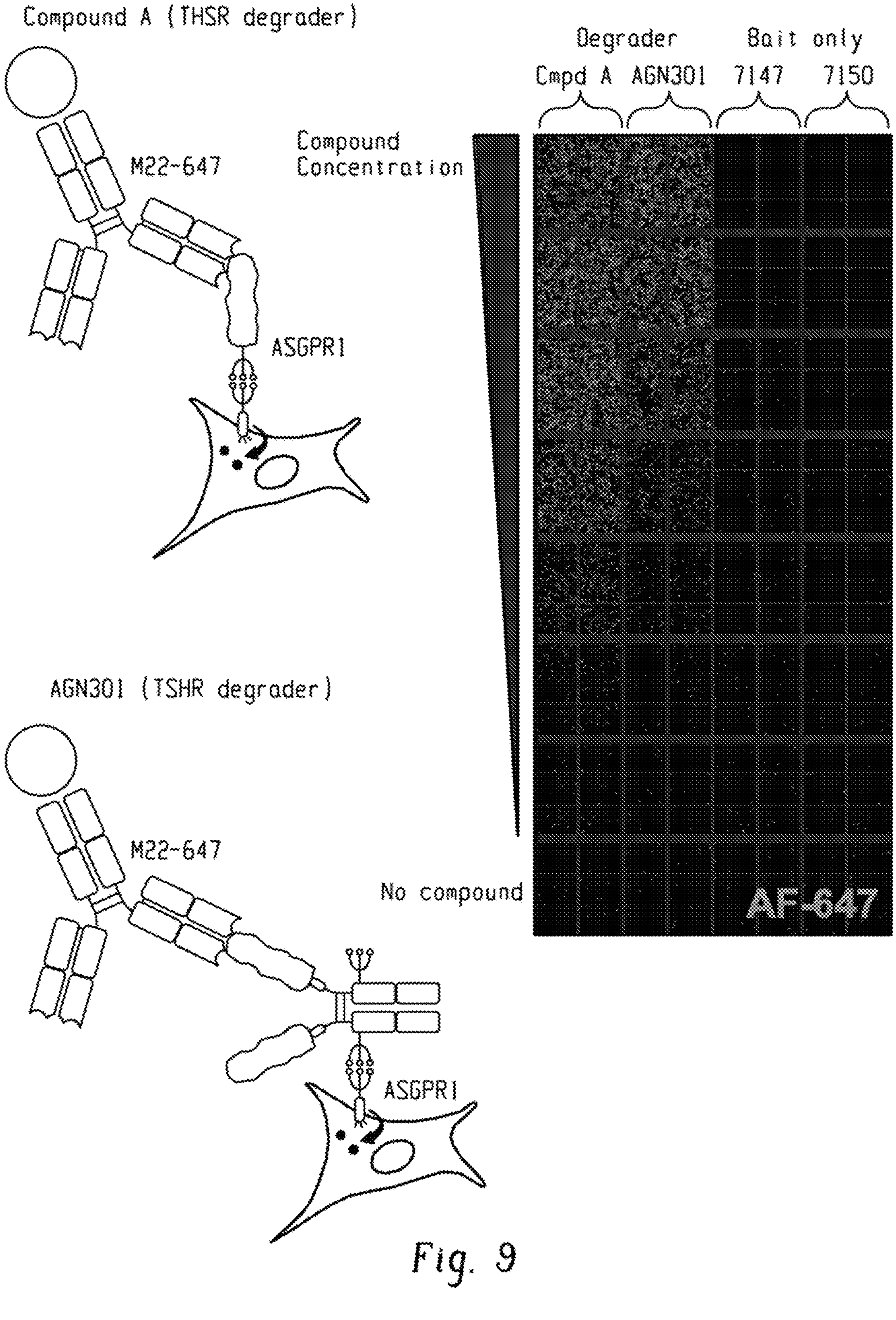
FIG. 9 shows results of the cellular internalization of the agonistic, patient-derived anti-TSHR antibody M22 upon addition of AGN301, in a concentration-response manner.
Figure 9:
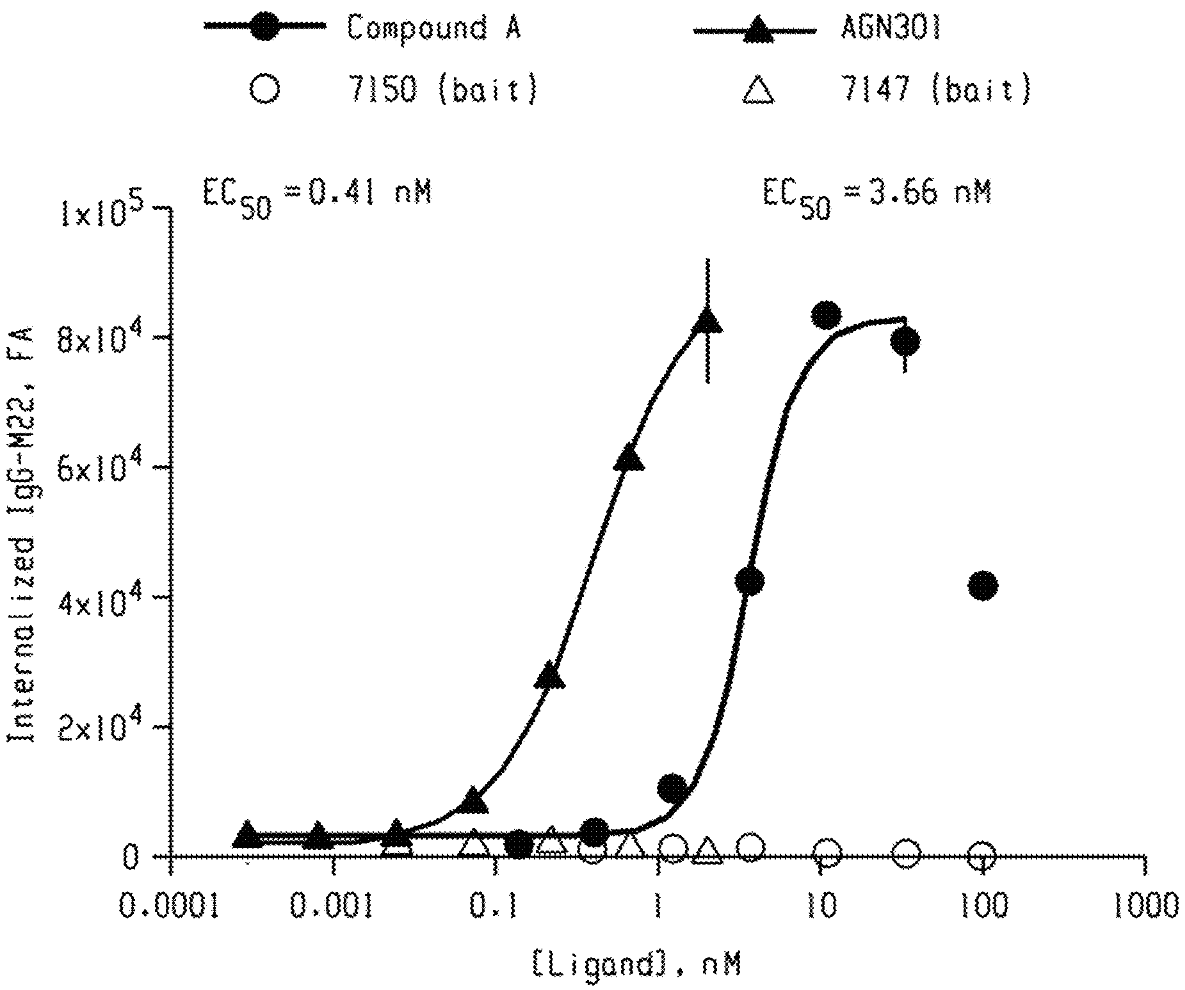

FIG. 9 shows results of the cellular internalization of the agonistic, patient-derived anti-TSHR antibody M22 by AGN301 (and Compound A).

Example 11

In Vivo Pharmacodynamics

AGN301 rapidly depletes patient-derived anti-TSHR antibody M22 added to mice (0.4 μg/mouse) from the mice both intravenously and subcutaneously.

AGN301 (intravenously) 8 mpk
AGN301 (intravenously) 3 mpk
AGN301 (subcutaneously) 3 mpk
AGN301 (subcutaneously) 0.3 mpk
AGN301 (subcutaneously) 0.1 mpk For AGN301 subcutaneously (SC), all dose levels tested, 3, 0.3, and 0.1 mpk, successfully depleted >90% added M22 antibody. 8 mpk dose achieved higher $C_{max}$ than 3 mpk. AGN301 (3 mpk IV) achieved ~95% depletion of M22 antibody. No rebound of M22 antibody effect was observed. TSH was not depleted by AGN301 dosed intravenously.

For the in vivo proof-of-concept, degraders rapidly remove patient-derived anti-TSHR (M22) in mouse.

Figure 10A:
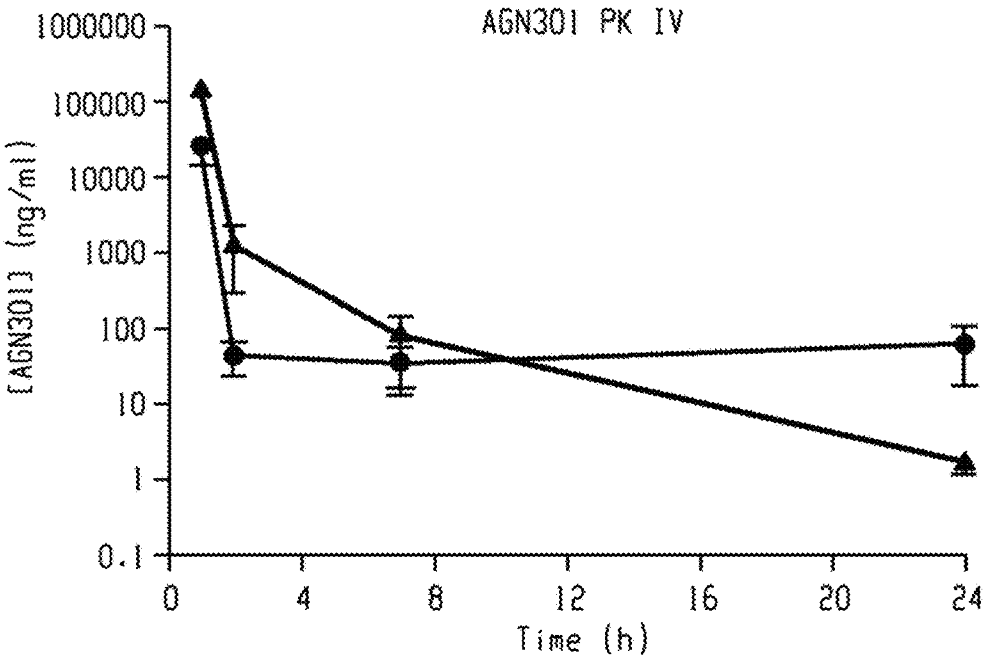
FIG. 10 shows results of the in vivo PK/PD study with AGN301 in mouse, dosed intravenously (IV)
Figure 10B:
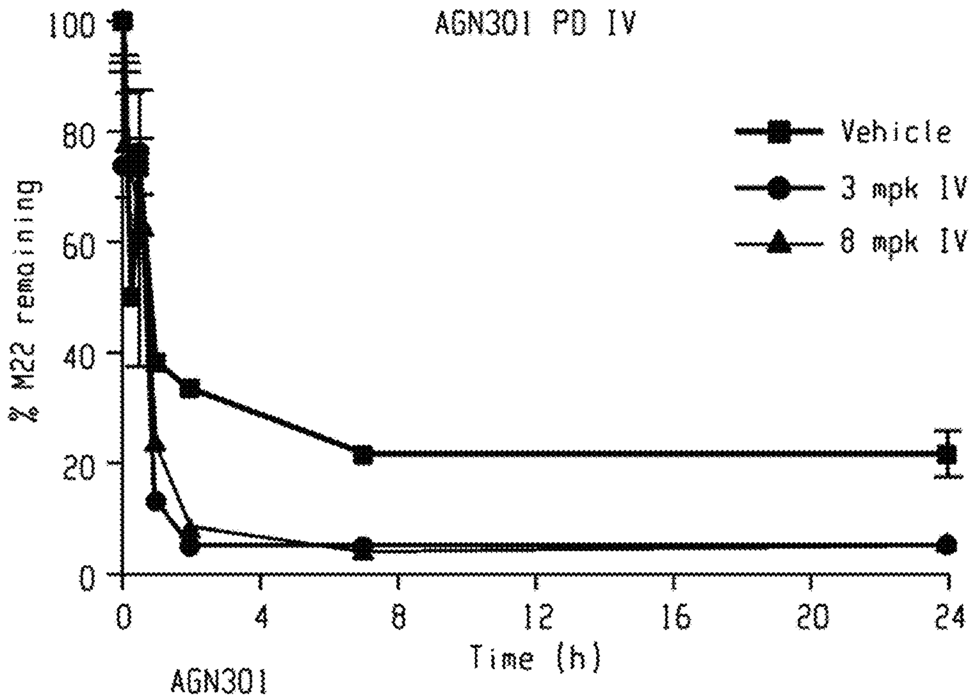
Figure 10B:
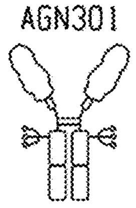

FIG. 10 shows results of the in vivo PK/PD study with AGN301 in mouse, dosed intravenously (IV)

Figure 11A:
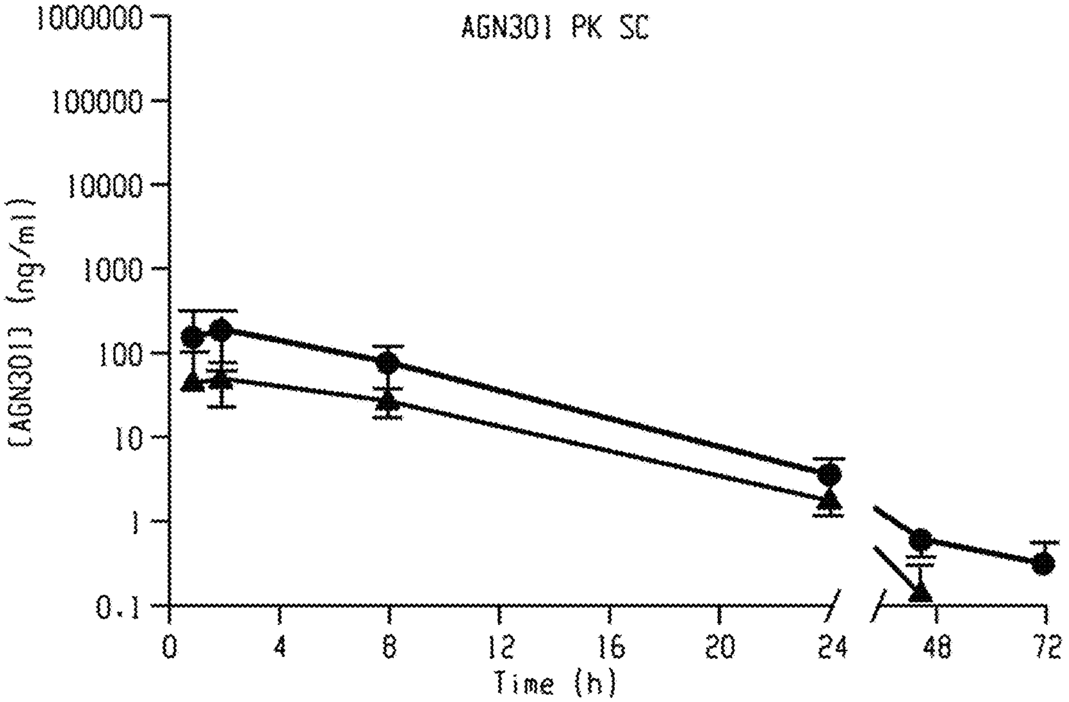
FIG. 11 shows results of the in vivo PK/PD with AGN301 in mouse, dosed subcutaneously (SC)
Figure 11B:
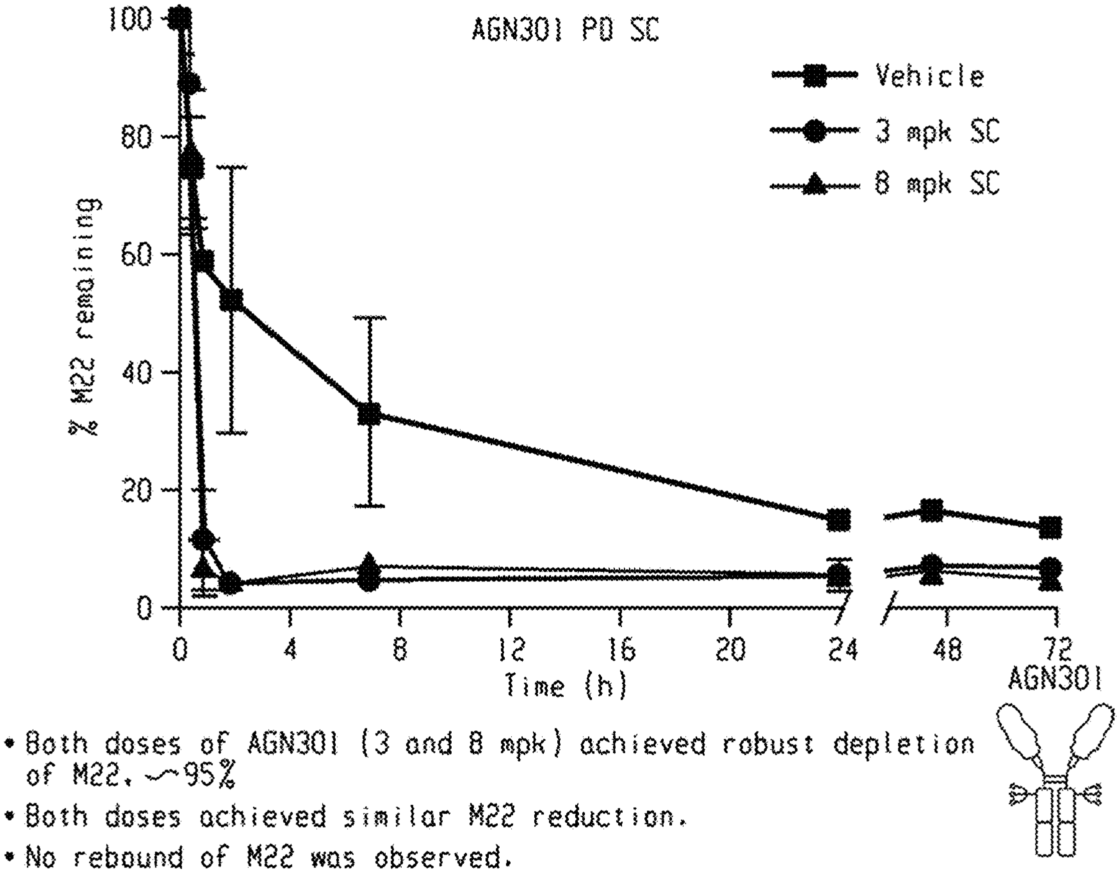

FIG. 11 shows results of the in vivo PK/PD with AGN301 in mouse, dosed subcutaneously (SC).

Figure 12:
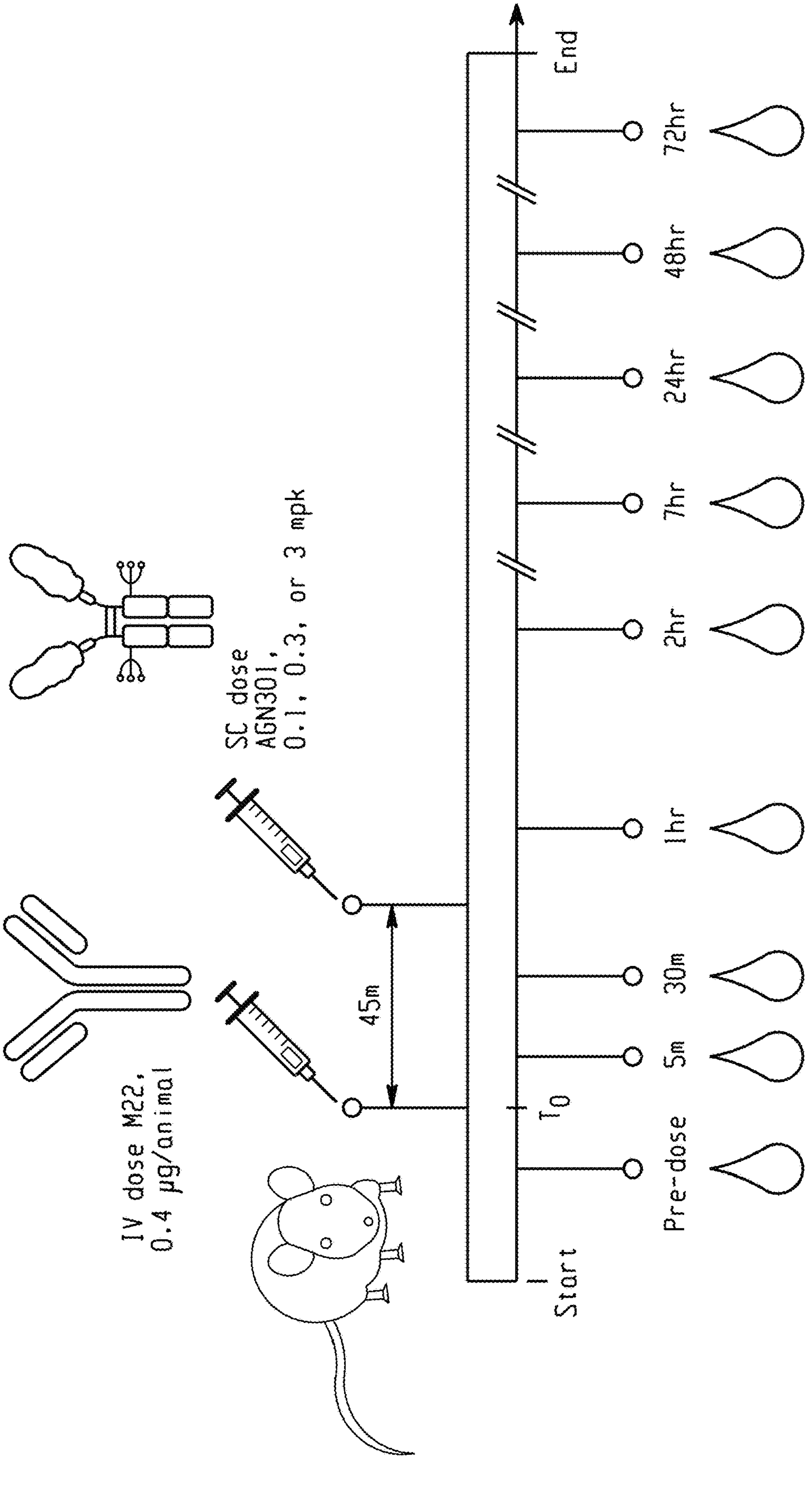
FIG. 12 shows results of the in vivo PD dose-titration of AGN301 in mouse, dosed subcutaneously (SC)
Figure 12:
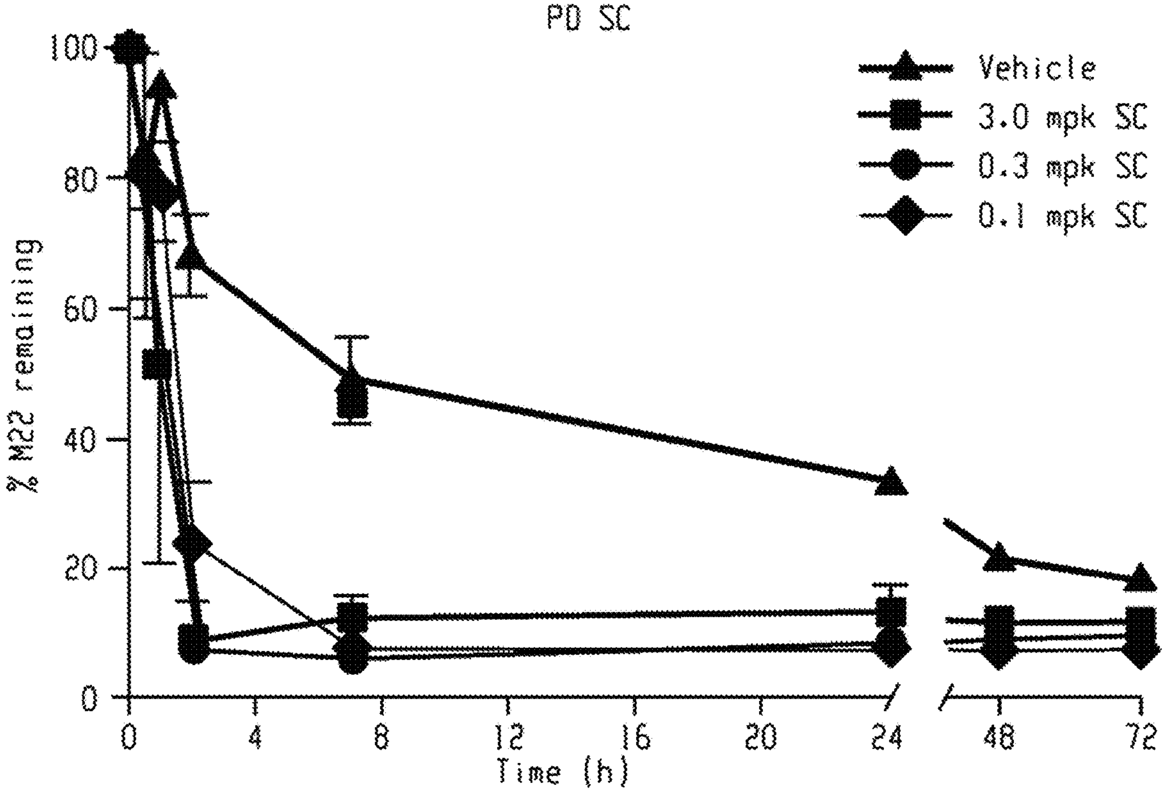
Figure 12:
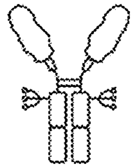
Figure 13:
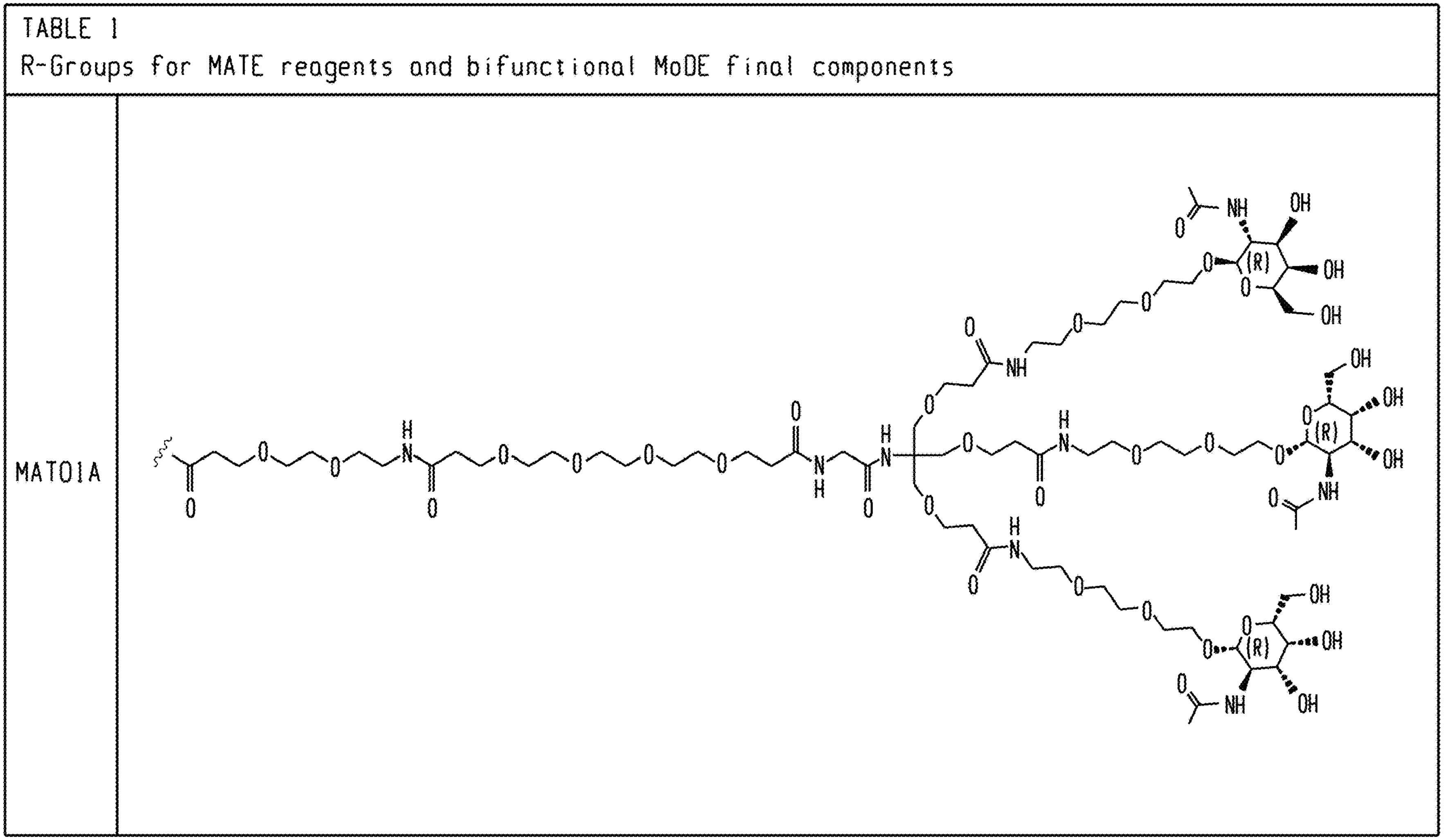
FIG. 13 is a table of R-Groups for MATE reagents and bifunctional MoDE final compounds.
Figure 13:
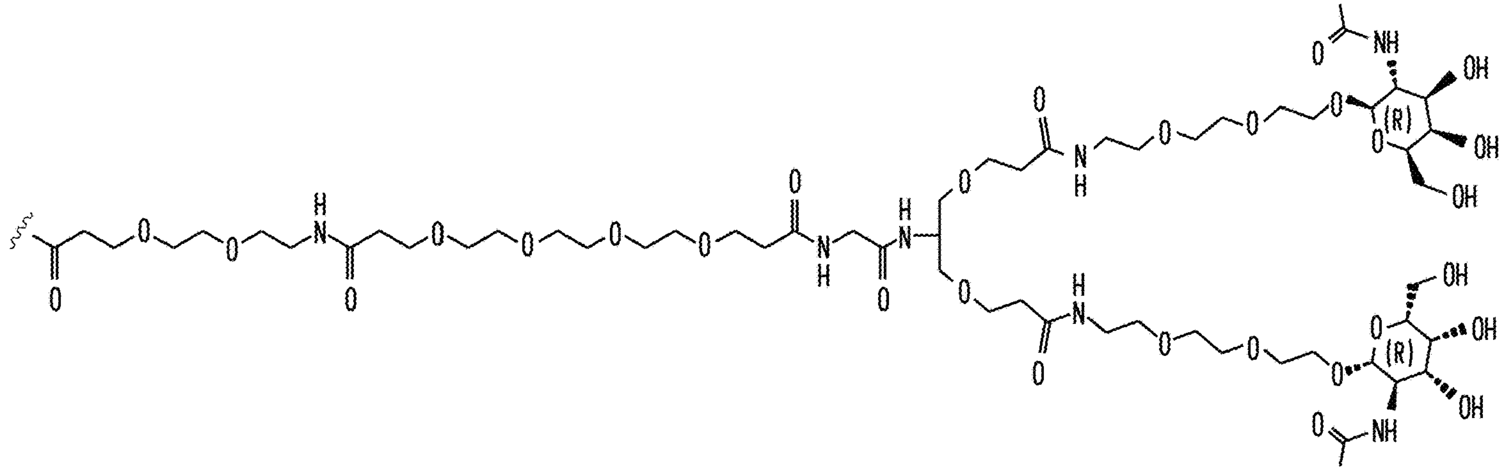
Figure 13:
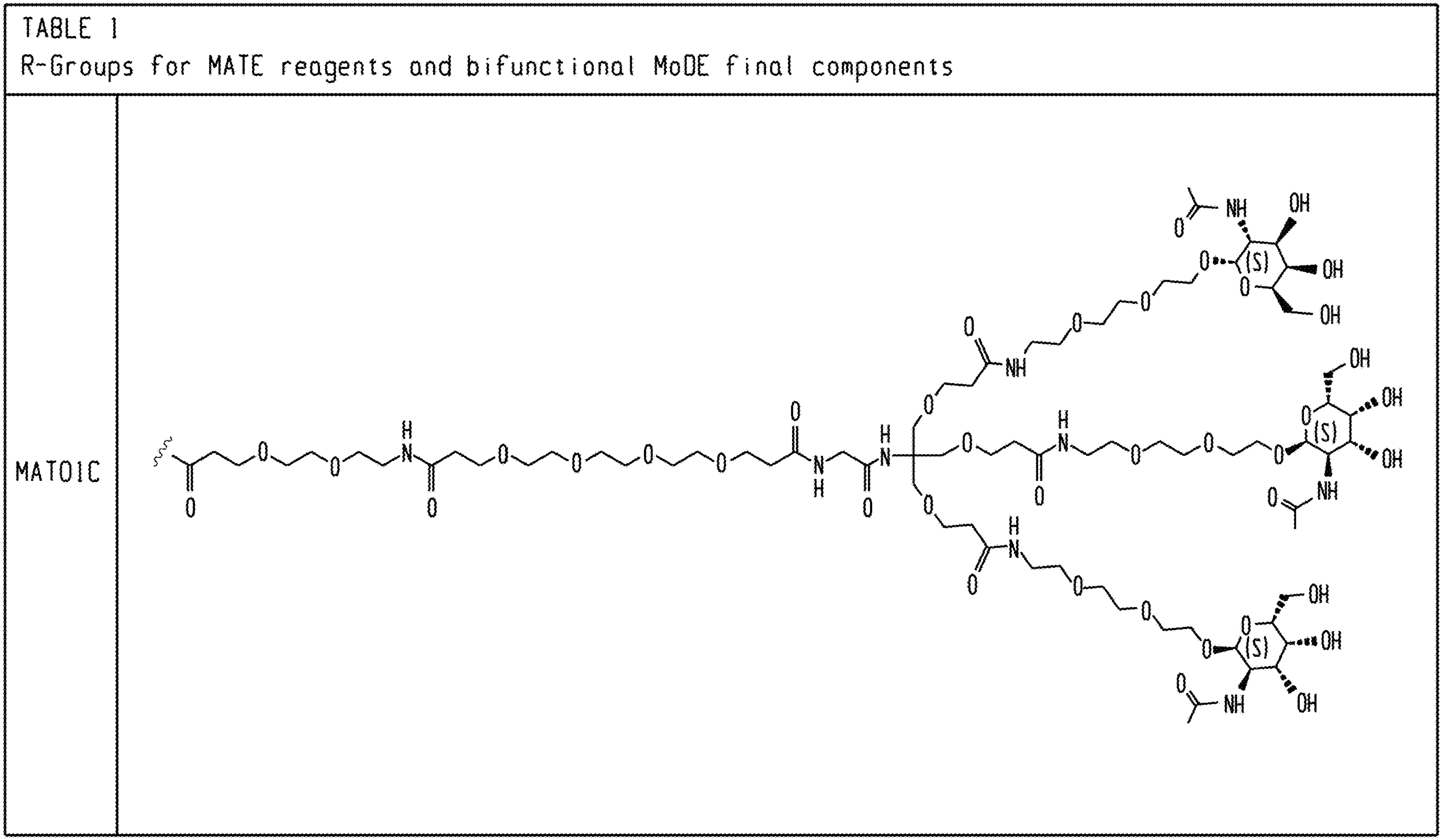
Figure 13:
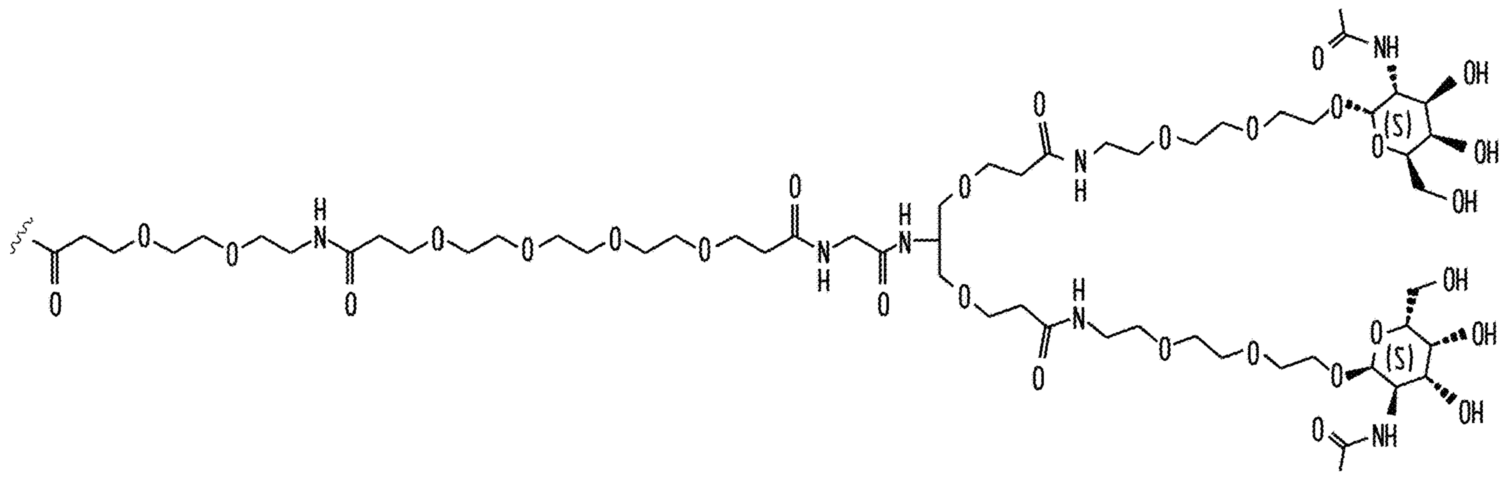
Figure 13:
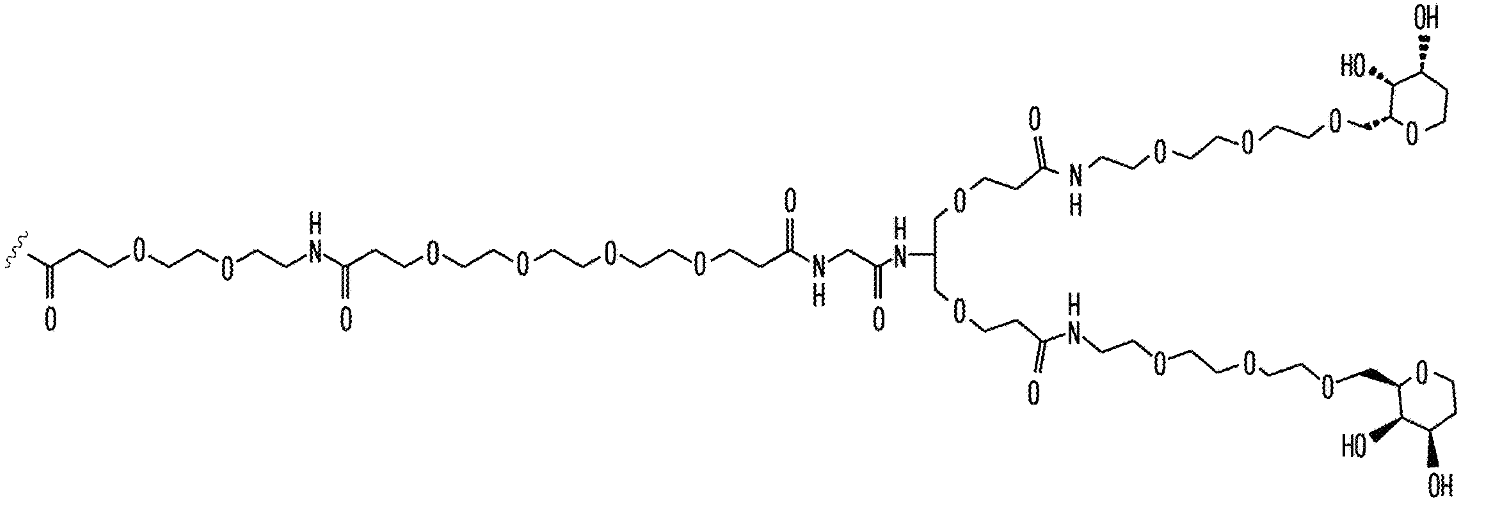
Figure 13:
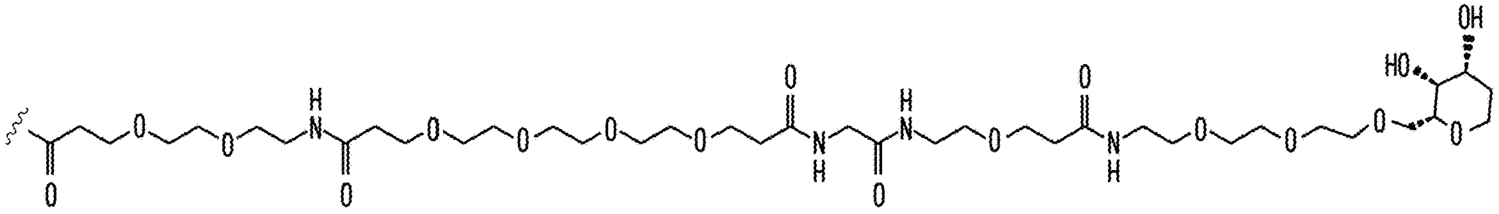
Figure 13:
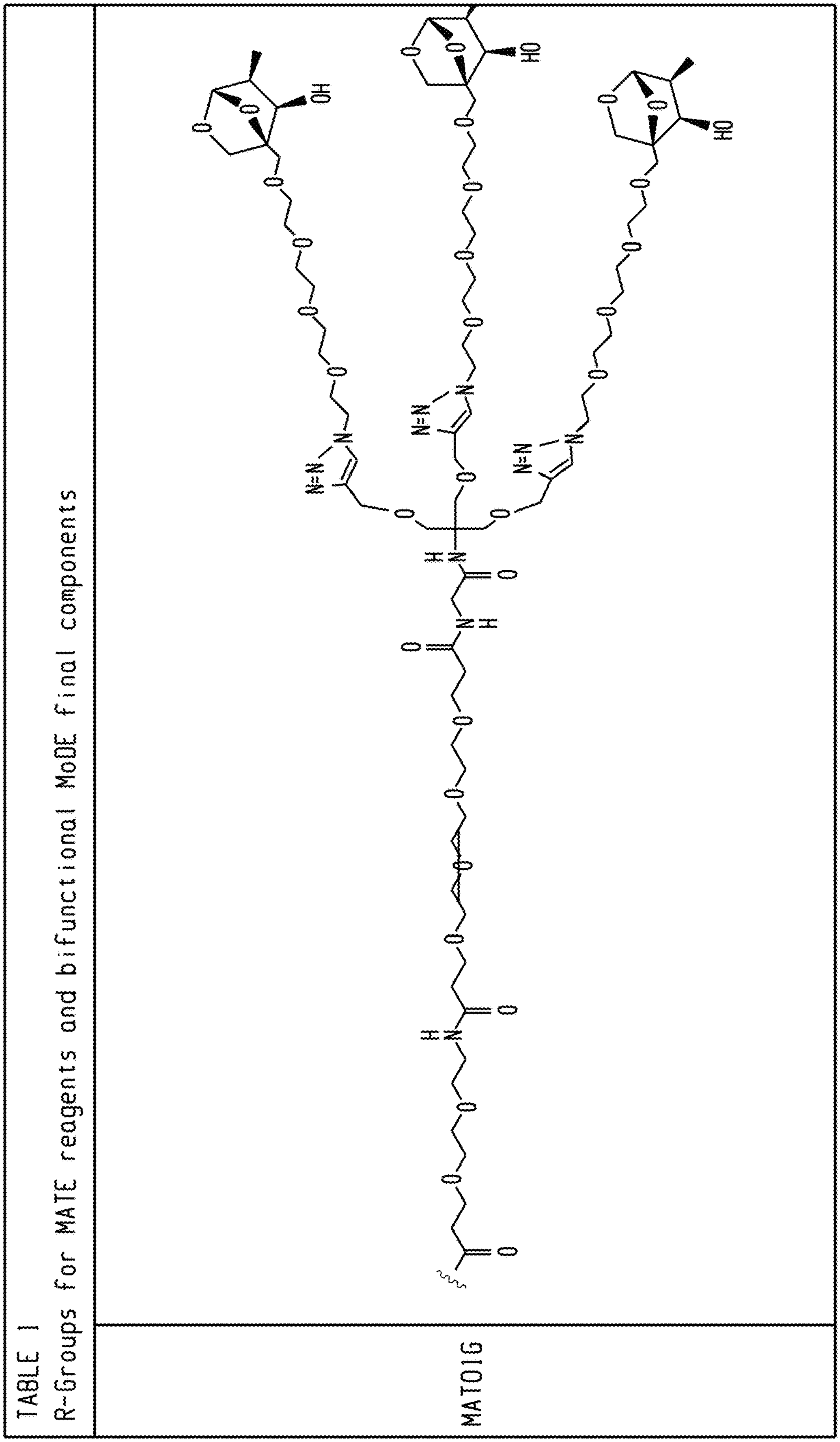
Figure 13:
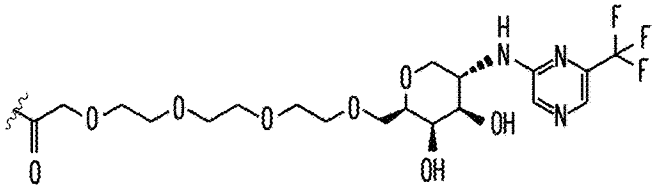
Figure 13:
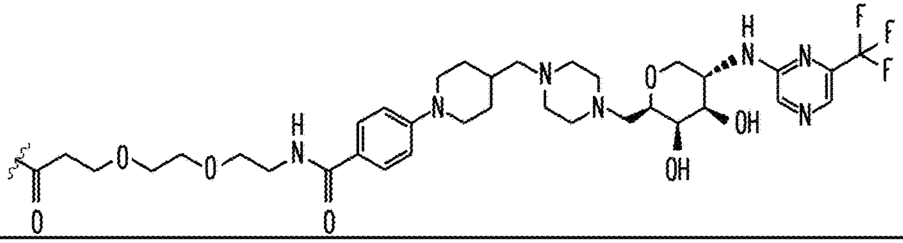
Figure 13:
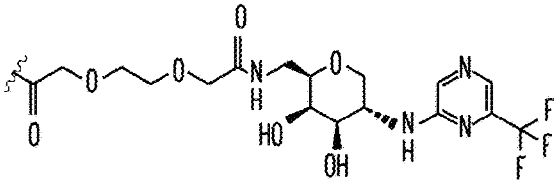
Figure 13:
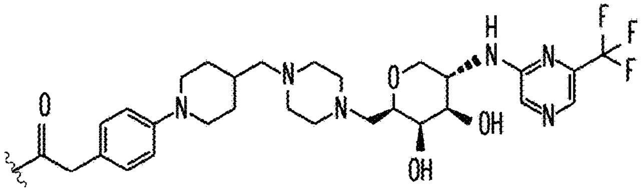

FIG. 12 shows results of the in vivo PD dose-titration of AGN301 in mouse, dosed subcutaneously (SC).

Example 12

Pharmacodynamic Biotinylated M22 Method

Biotinylated M22 levels were checked using an MSD format. Briefly, multi array 96-well streptavidin coated plates were blocked with 150 μL/well MSD Blocker A for a minimum of 1 hour at room temperature with shaking at 700 rpm. During the block incubation, a standard curve of biotinylated-M22 was prepared in diluent-100 starting at 500 ng/ml with 5-fold dilutions for eight total concentrations. Samples were diluted in diluent-100 accordingly for each experiment aiming for the initial dose of antibody to be approximately 100 ng/ml. After the blocking incubation, the plates were washed three times with phosphate-buffered saline with Tween 20 at 150 μL/well using a plate-washer. The M22 dilution curve and each sample were added 25 μl/well to the appropriate wells in duplicate and incubated for two hours at room temperature with shaking. After incubation, the plates were washed with phosphate-buffered saline with Tween 20 three times and then incubated with a sulfo-tagged anti-human IgG antibody that detects the Fab region of the IgG at 0.8 μg/mL. The plates were incubated for 1.5 hours at room temperature with shaking then finally washed three times with phosphate-buffered saline with Tween 20. Read Buffer A was added to each well and the plates were immediately read on the MSD instrument.

Example 13

Pharmacokinetics (AGN301)

Multi array 96-well streptavidin plates were coated with 25 L/well biotinylated soybean lectin (SBA) for 1 hour at room temperature with shaking at 700 rpm. The solution was dumped and 150 μL MSD Blocker A was added to each well. The plates were incubated at room temperature for one hour with shaking. During the block incubation, a standard curve of AGN301 was prepared in diluent-100 starting at 1000 ng/ml with five-fold dilutions for eight total concentrations. Samples were diluted in diluent-100 accordingly for each experiment with a minimum twenty-fold dilution to prevent background plasma interference. After the blocking incubation, the plates were washed three times with phosphate-buffered saline with Tween 20 at 150 μL/well using a plate-washer. The AGN301 dilution curve and each sample were added 25 μL/well to the appropriate wells in duplicate and incubated for two hours at room temperature with shaking. After incubation, the plates were washed with phosphate-buffered saline with Tween 20 three times and then incubated with a sulfo-tagged M22 antibody at 4 μg/mL. The plates were incubated for 1.5 hours at room temperature with shaking then finally washed three times with phosphate-buffered saline with Tween 20. Read Buffer A was added to each well and the plates were immediately read on the MSD instrument.

Example 14

Patient Sample Screening (UPlex)

Each protein bait was assigned a spot for a UPLEX MSD sector plate each with a spot-specific linker that enables multiplexed loading. Loading complexes were prepared by adding 400 μL 420 nM of biotinylated ABT301 to 600 μL of the assigned linker, mixing well by pipette, then incubation at room temperature for thirty minutes. The reaction was stopped by adding 400 μL of Stop solution and incubated for thirty minutes at room temperature before being combined into a single loading solution. The loading solution was added 50 μL/well to 2 6-spot UPLEX MSD plates and incubated at room temperature for one hour with shaking at 700 rpm. The solution was dumped and 150 μL MSD Blocker A was added to each well. The plates were incubated at room temperature for one hour with shaking. During the block incubation, a standard curve of M22 and K1-70 anti-TSHR antibodies was prepared in diluent-100 starting at 2000 ng/ml with 4-fold dilutions for eleven total concentrations. Patient samples were diluted fifty-fold in diluent-100 by adding 4 μL of serum to 196 μl diluent-100. After the blocking incubation, the plates were washed three times with phosphate-buffered saline with Tween 20 at 150 μL/well using a plate-washer. The antibody standard curves and each patient sample were added 25 μl/well to the appropriate wells in duplicate and incubated for 2 hours at room temperature with shaking. After incubation, the plates were washed with phosphate-buffered saline with Tween 20 three times and then incubated with a sulfo-tagged anti-human IgG antibody that detects the Fab region of the IgG at 0.8 µg/mL. The plates were incubated for 1.5 hours at room temperature with shaking then finally washed three times with phosphate-buffered saline with Tween 20. Read Buffer B was added to each well and the plates were immediately read on the MSD instrument.

Degraders effectively captured anti-TSHR autoantibodies from Graves' disease patient samples. See FIG. 7.

Example 15

Patient Sample Screening (Competition)

Multi array 96-well streptavidin plates were coated with 25 µL/well biotinylated ABT301 for 1 hour at room temperature with shaking at 700 rpm. The solution was dumped and 150 µL MSD Blocker A was added to each well. The plates were incubated at room temperature for one hour with shaking. During the block incubation, patient samples were diluted fifty-fold by mixing 16 µl serum with 784 µL diluent-100 to create a 2× working solution. A no competition control was prepared in diluent-100. A 1× sample solution was prepared by adding 60 µL of each 2× patient sample to 60 µL of diluent-100 no compound control. After the blocking incubation, the plates were washed three times with phosphate-buffered saline with Tween 20 at 150 µl/well using a plate-washer. The samples were added 25 µL/well to the appropriate wells in duplicate and incubated for two hours at room temperature with shaking. After incubation, the plates were washed with phosphate-buffered saline with Tween 20 three times and then incubated with a sulfo-tagged anti-human IgG antibody that detects the Fab region of the IgG at 0.8 µg/mL. The plates were incubated for 1.5 hours at room temperature with shaking then finally washed three times with phosphate-buffered saline with Tween 20. Read Buffer B was added to each well and the plates were immediately read on the MSD instrument.

Degraders effectively captured anti-TSHR autoantibodies from Graves' disease patient samples. See FIG. 8.

EQUIVALENTS

Persons having ordinary skill in the biomedical art will recognize or be able to determine using no more than routine experimentation many equivalents to the specific procedures described in this specification. These equivalents are within the scope of this invention and are covered by the following claims. For example, pharmaceutically acceptable salts other than those specifically disclosed in the description and Examples in this specification can be employed. Furthermore, it is intended that specific items within lists of items, or subset groups of items within larger groups of items, can be combined with other specific items, subset groups of items, or larger groups of items whether there is a specific disclosure in this specification identifying such a combination.

Further Embodiments

1. A composition of matter comprising a binding moiety that binds to anti-TSH receptor autoantibody, a cellular receptor-binding moiety capable of binding to hepatocytes or other degrading cells through asialoglycoprotein receptors (ASGPR) of hepatocytes or other cell receptors on surface degrading cells, and an optional linker moiety (for example, a single peptide linkage) connecting the anti-TSH receptor autoantibody-binding moiety and the cellular receptor-binding moiety.

2. The composition of matter of embodiment 1, having a structure of: AGN101, AGN102, or a pharmaceutically acceptable salt thereof, wherein each of a and b is independently an integer of 1 or greater; each AT or ABT is an anti-TSH receptor autoantibody-binding moiety or a fragment thereof; Lis a linker moiety; and each TBT is independently a cellular receptor-binding moiety that binds to hepatocytes or other degrading cells through asialoglycoprotein receptors (ASGPR) of hepatocytes or other cell receptors on the surface degrading cells in a patient or subject.

3. The composition of matter of embodiment 2, wherein a is 1, b is 3, and each TBT comprises an N-acetyl-D-galactosamine (GalNAc) moiety.

4. The composition of matter of embodiment 1, wherein the anti-TSH receptor autoantibody-binding moiety is selected from the Markush group consisting of TSH receptors, mutant TSH receptors, fragments comprising one or more epitopes of a TSH receptor, and polypeptide comprising one or more epitopes of a TSH receptor.

5. The composition of matter of embodiment 4, further comprising a VHH moiety conjugated to the linker moiety, wherein one or two TSH receptors, mutant TSH receptors, or fragments thereof, or one or two polypeptides comprising one or more epitopes of a TSH receptor are conjugated to one or each of the protein chains of the VHH moiety.

6. The composition of matter of embodiment 1, wherein: the anti-TSH receptor autoantibody-binding moiety comprises IgG1 or an antigen-binding fragment connected to the linker L at an amino acid residue selected from K246 and K248 of an IgG1 heavy chain and amino acid residues corresponding thereto; or the anti-TSH receptor autoantibody-binding moiety comprises IgG2 or a fragment thereof connected to the linker at an amino acid residue selected from K251 and K253 of an IgG2 heavy chain and amino acid residues corresponding thereto; or the anti-TSH receptor autoantibody-binding moiety comprises IgG4 or an antigen-binding fragment thereof, connected to the linker at an amino acid residue selected from K239 and K241 of an IgG4 heavy chain and amino acid residues corresponding thereto.

7. The composition of matter of embodiment 6, wherein the anti-TSH receptor autoantibody-binding moiety comprises IgG1 and is over 90% connected to the linker L at a K248 as compared with any other linkage with a lysine of the antibody.

8. The composition of matter of embodiment 6, wherein: the anti-TSH receptor autoantibody-binding moiety comprises IgG1 and has two linkers at an amino acid connected to residue selected from K246 and K248 of each of the IgG1 heavy chains and amino acid residues corresponding thereto.

9. The composition of matter of embodiment 1, wherein the cellular receptor-binding moiety comprises an ASGPR binding group connected through an amine group.

10. The composition of matter of embodiment 1, wherein the cellular receptor-binding moiety comprises an ASGPR binding group according to the chemical structure

[TBT101]

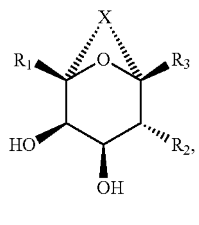

or

-continued

[TBT102]

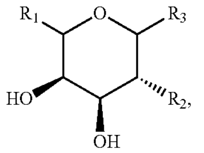

or a pharmaceutically acceptable salt, stereoisomer, solvate, or polymorph thereof. Groups $R^1$, $R^2$, $R_3$, and X may be the same as described in International Patent Publication WO 2019/199634 and International Patent Publication WO 2019/199621.

11. The composition of matter of embodiment 1, wherein the cellular receptor-binding moiety has the structure

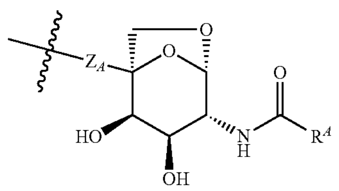

or

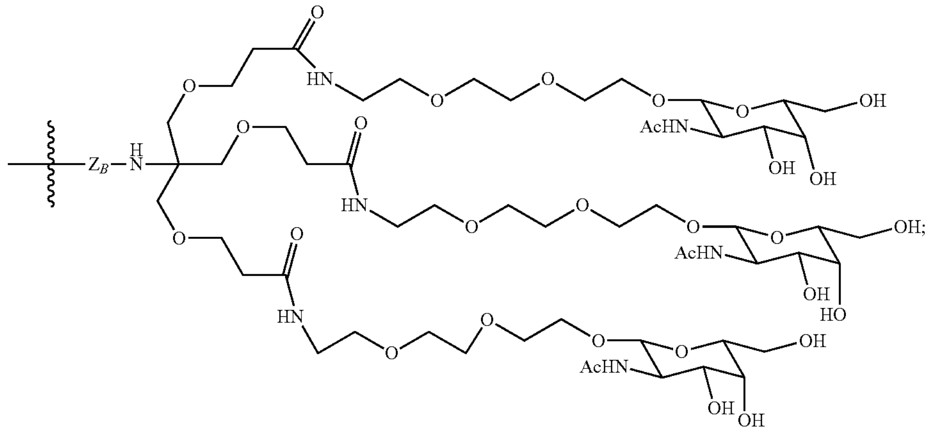

where RA is a C1-C3 alkyl group optionally substituted with 1-5 halo groups (preferably RA is a methyl or ethyl group optionally substituted with from 1-3 fluoro groups); ZA is —(CH2)IM, —O—(CH2)IM, S—(CH2)IM, NRM-(CH2) IM, C(O)—(CH2)IM-, a PEG group containing from 1 to 8 preferably 1-4 ethylene glycol residues or a —C(O)(CH2) IMNRM group (preferably a PEG containing group comprising from 1 to 8 ethylene glycol, preferably 2-4 ethylene glycol residues) where IM and RM are the same as above; and ZB is absent, (CH2)IM, C(O)—(CH2)IM- or C(O)—(CH2)IM-NRM, where IM and $R_M$ are the same as above.

12. The composition of matter of embodiment 1, wherein the ASGPR binding group is N-acetyl-D-galactosamine.

13. A pharmaceutical composition comprising a composition of matter any of the preceding embodiments 1-12 and a pharmaceutically acceptable excipient.

14. A composition comprising: a first composition of matter comprising: an anti-TSH receptor autoantibody-binding moiety, a cellular receptor-binding moiety capable of binding to hepatocytes or other degrading cells through asialoglycoprotein receptors (ASGPR) of hepatocytes or other cell receptors on surface degrading cells, and a linker moiety connecting the anti-TSH receptor autoantibody-binding moiety and the cellular receptor-binding moiety, and at least one additional composition of matter comprising: a cellular receptor-binding moiety capable of binding to hepatocytes or other degrading cells through asialoglycoprotein receptors (ASGPR) of hepatocytes or other cell receptors on surface degrading cells, and a linker moiety connecting the cellular receptor-binding moiety and capable of binding to an anti-TSH receptor autoantibody-binding moiety.

15. A method of removing anti-TSH receptor autoantibody in a patient or subject in need comprising administering to the patient or subject an agent of any of embodiments 1-12.

16. A method of treating a disease state or condition associated with the upregulation of anti-TSH receptor autoantibody in a patient by administering to the patient an effective amount of an agent (TRAP) of any of embodiments 1-12.

17. A method of treating Graves' disease by administering to a Graves' disease patient an effective amount of an agent (TRAP) of any of embodiments 1-12.

18. A method of treating Hashimoto thyroiditis by administering to a Hashimoto thyroiditis patient an effective amount of agent (TRAP) of any of embodiments 1-12.

REFERENCES

Persons having ordinary skill in the biomedical art can use these patents, patent applications, and scientific references as guidance to predictable results when making and using the invention.

PATENT LITERATURE

European Pat. No. EP1355919B1 (MedImmune LLC et al.), Molecules with extended half-lives, compositions, and uses thereof.

European Pat. No. EP1565493B1 provides details about the properties of a human monoclonal autoantibody with powerful stimulating activity and its interaction with the TSH receptor.

European Pat. No. EP1021721B1 (RSR Ltd.), Assays for TSH receptor autoantibodies.

Intl. Pat. Publ. WO 2002/060919 (MedImmune LLC et al.), Molecules with extended half-lives, compositions and uses thereof.

Intl. Pat. Publ. WO 2006/016121 A1 (RSR Ltd.) discloses TSH receptor mutants carrying, e.g., a point mutation at position 255 which are less stimulated by TSH receptor autoantibodies. WO 2006/016121A1 discloses a mutated TSH receptor preparation including at least one point mutation which can be used in the differential screening and identification of patient serum stimulating TSH receptor autoantibodies, patient serum blocking TSH receptor autoantibodies and TSH in a sample of body fluid from a patient being screened.

Intl. Pat. Publ. WO 2008/099185A1 discloses the isolation and characterization of a human monoclonal antibody 5C9 to the TSH receptor that is an effective antagonist of TSH and of stimulating TSH receptor autoantibodies in patient sera.

Intl. Pat. Publ. WO 2010/073012 A2 (RSR Ltd.) discloses TSH receptor mutants, which are more thermostable than the wild-type receptor, e.g., TSH receptor LRD C-CAP, which contains amino acids 1-409 of the human TSH receptor having amino acids 306-384 removed. TSH receptor mutants, such as TSHR260, are provided. Labeling with alkaline phosphatase is proposed. WO 2010/073012 also describes an assay to measure TSH receptor autoantibodies based on the bridging principle whereby divalent antibodies bind to the TSH receptor coated onto an ELISA plate well with one arm and to liquid phase TSHR260-alkaline phosphatase with the other arm to form a bridge. WO 2010/073012 further discloses the isolation and characterization of a further human monoclonal autoantibody (K1-18) with powerful stimulating activity and a human monoclonal autoantibody (K1-70) that is a potent TSH receptor antagonist from the peripheral blood lymphocytes of a patient.

Intl. Pat. Publ. WO 2012/017021 (Graffinity Pharmaceuticals GmbH), Ligands for antibody and Fc-fusion protein purification by affinity chromatography.

Intl. Pat. Publ. WO 2012/098413 (Heptares Therapeutics Ltd.) discloses means and methods for producing mutant G-protein coupled receptors (GPCRs) with an increased stability such as increased thermostability relative to a parent GPCR. Provided are the mutation methods.

Intl. Pat. Publ. WO 2015/189543 (RSR Ltd.), Glycoprotein hormone receptor mutations, discloses mutant thyroid stimulating hormone receptor fragments comprising one or more mutations, wherein the mutant TSH receptor has increased thermostability with respect to the equivalent wild type TSH receptor or fragment. See the corresponding European Pat. No. EP3155011 (RSR Ltd.) and U.S. Pat. No. 11,732,026 (Rees Smith et al.).

Intl. Pat. Publ. WO 2019/023501 (Kleo Pharmaceuticals, Inc.), Universal ABT compounds and uses thereof.

Intl. Pat. Publ. WO 2019/136442 (Kleo Pharmaceuticals, Inc.), Cd16a binding agents and uses thereof.

Intl. Pat. Publ. WO 2024/228935 (Biohaven Therapeutics, Ltd.), Bifunctional degraders of galactose-deficient immunoglobulins.

Intl. Pat. Publ. WO 2025/030009 (Merida Biosciences, Inc.), Molecules for controlling immune response.

U.S. Pat. No. 6,228,597 (Parmentier et al.).

U.S. Pat. No. 6,933,364 (Hattori et al.).

U.S. Pat. No. 7,083,784 (Dall'Acqua et al.), Molecules with extended half-lives, compositions and uses thereof.

U.S. Pat. No. 7,658,921 (Dall'Acqua et al.), Molecules with extended half-lives, compositions and uses thereof.

U.S. Pat. No. 8,088,376 (Chamberlain et al.), Fc variants with altered binding to FcRn.

U.S. Pat. No. 8,969,526 (Baehner), Antibody Fc variants.

U.S. Pat. No. 9,562,100 (Dall'Acqua et al.), Molecules with extended half-lives, compositions and uses thereof.

U.S. Pat. Publ. 2019/0111149 (Gardiner et al.), Anti-EGFR antibody drug conjugate.

NON-PATENT LITERATURE

Acqua et al., Increasing the affinity of a human IgG1 for the neonatal Fc receptor: biological consequences. The Journal of Immunology, 169 (9), 5171-5180 (2002).

Alves, Kiziltepe, & Bilgicer, Oriented surface immobilization of antibodies at the conserved nucleotide binding site for enhanced antigen detection. Langmuir, 28, 9640-9648 (2012).

Bhattacharya et al., Rapid computational prediction of thermostabilizing mutations for G protein-coupled receptors, Journal of Chemical Theory and Computation, Vol. 10, No. 11, pages 5149-5160 (Oct. 14, 2014).

Bolton et al., Measurement of thyroid-stimulating hormone receptor autoantibodies by ELISA. Clin Chem., 45, 2285-2287 (1999).

Bunin et al., American Academy of Neurology (AAN) 2024 Annual Meeting (Apr. 18, 2024)

Caianiello et al., Bifunctional small molecules that mediate the degradation of extracellular proteins. Nature Chemical Biology, 17 (9), 947-953 (2021) describes the ASGPR-dependent mechanism of Molecular Degraders of Extracellular targets (MoDE)- induced degradation.

Chazenbalk et al., Thyroid-stimulating autoantibodies in Graves preferentially recognize free A subunit, not the thyrotropin holoreceptor. Journal of Clinical Investigation 110 209-217 (2002).

Cheever et al., Chimeric autoantibody receptor T cells specifically eliminate Graves' Disease autoreactive B cells. Frontiers in Immunology, 16, 1562662 (Apr. 8, 2025).

Choe, Durgannavar, & Chung, Fc-binding ligands of immunoglobulin G: An overview of high affinity proteins and peptides. Materials (Basel), 9 (12), 994 (Dec. 8, 2016).

Cobb et al., A combination of two human neutralizing antibodies prevents SARS-COV-2 infection in rhesus macaques. bioRxiv, 2021-09 (2021).

Davies et al., Graves' disease. Nature Reviews Disease Primers, 6 (1), 52 (Jul. 2, 2020). Anti-TSHR antibodies are highly specific to Graves' disease and are used in diagnosis.

Eckstein et al., Thyrotropin receptor autoantibodies are independent risk factors for Graves' ophthalmopathy and help to predict severity and outcome of the disease. The Journal of Clinical Endocrinology & Metabolism, 91 (9), 3464-70 (Sep. 1, 2006). Stimulating anti-TSHR antibody titer correlates with Graves' orbitopathy severity.

Furmaniak et al., TSH receptor specific monoclonal autoantibody K1-70™ targeting of the TSH receptor in subjects with Graves' disease and Graves' orbitopathy-results from a phase I clinical trial. Clinical Endocrinology, 96, 878-887 (2022).

Gupta et al., Computationally designed antibody-drug conjugates self-assembled via affinity ligands. Nature Biomedical Engineering, 3, 917-929 (2019).

Kruljec et al., Alternative affinity ligands for immunoglobulins. Bioconjugate Chem., 28 (8): 2009-2030 (2017).

Kerntke et al., There is (scientific) strength in numbers: a comprehensive quantitation of Fc gamma receptor numbers on human and murine peripheral blood leukocytes. Frontiers in immunology, 11, 118. (Feb. 5, 2020) describes FcγRIIB protein expression.

Kruljec et al., Development and characterization of peptide ligands of immunoglobulin G Fc region. Bioconjugate Chem., 29 (8), 2763-2775 (2018).

Lane et al., New therapeutic horizons for Graves' hyperthyroidism. Endocrine Reviews, 41 (6), 873-84 (Dec. 1, 2020).

Latif et al., Endocrinology and Metabolism Clinics of North America, 38, 319-341 (2009).

Lytton et al., A novel thyroid stimulating immunoglobulin bioassay is a functional indicator of activity and severity of Graves' orbitopathy. The Journal of Clinical Endocrinology & Metabolism, 95 (5), 2123-31 (May 1, 2010). Stimulating anti-TSHR antibody titer correlates with Graves' orbitopathy severity.

Magnani et al., Co-evolving stability and conformational homogeneity of the human adenosine A (2a) receptor, Proceedings of the National Academy of Sciences, U.S.A., Vol. 105, No. 31, pages 10744-10749, (Aug. 5, 2008) relates to the conformational thermostabilization of the human adenosine A2a receptor.

Miller-Gallacher et al., Crystal structure of a ligand-free stable TSH receptor leucine-rich repeat domain. Journal of Molecular Endocrinology, Volume 62, Issue 3, page 117-128 (April 2019). Reported production and crystallization of an isolated TSHR-Leucine-Rich Domain.

Muguruma et al., Kinetics-based structural requirements of human immunoglobulin G binding peptides. ACS Omega, 4, 14390-14397 (2019).

Mullard, Extracellular targeted protein degrader removes antibodies in first test in humans. Nature Reviews Drug Discovery (Jun. 18, 2024).

Mustafaoglu et al., Antibody purification via affinity membrane chromatography method utilizing nucleotide binding site targeting with a small molecule, Analyst, 141 (24), 6571-6582 (Nov. 28, 2016).

Nagayama, Kaufman, Seto, & Rapoport, Molecular cloning, sequence and functional expression of the cDNA for the human thyrotropin receptor. Biochem. Biophys. Res. Commun. 165 (3), 1184-1190 (1989).

Nakatake et al., Estimation of serum TSH receptor autoantibody concentration and affinity. Thyroid, 16 (11), 1077-84 (Nov. 1, 2006).

Núñez Miguel et al., Structure of full-length TSH receptor in complex with antibody K1-70™. Journal of Molecular Endocrinology, 70, e220120 (2022).

Pokhrel & Bhusal, Graves' Disease. In: StatPearls [Internet] (Treasure Island (FL), StatPearls Publishing, January 2024).

Rapoport et al., The thyrotropin (TSH) receptor: interaction with TSH and autoantibodies. Endocrine Reviews. 19, 673-716 (1988).

Rees Smith et al., TSH receptor antibodies. Thyroid, 17, 923-938 (2007).

Rees Smith et al., TSH receptor-autoantibody interactions. Hormone and Metabolic Research, 41, 448-455 (2009).

Rees Smith, Mclachlan, & Furmaniak, Autoantibodies to the thyrotropin receptor. Endocrine Reviews, 9, 106-121 (1988).

Sanders et al., Ballière's Clinical Endocrinology and Metabolism, 11, 451-479 (London, Ballière Tindall, 1997).

Sanders et al., Crystal structure of the TSH receptor bound to a blocking type TSHR autoantibody. Journal of Molecular Endocrinology, 46, 81-99 (2011).

Sanders et al., Crystal structure of the TSH receptor in complex with a thyroid-stimulating autoantibody. Thyroid, 17, 395-410 (2007) aligned human TSHR-LRD (M22-L260) to the mouse sequence and noted a high degree of identity for residues important for M22 binding based on a human TSHR-M22 structure.

Sanders et al., Human monoclonal thyroid stimulating autoantibody. Lancet, 362 (9378), 126-128 (2003).

Saxena & Wu, Advances in therapeutic Fc engineering-modulation of IgG-associated effector functions and serum half-life. Frontiers in immunology, 7, 580 (2016) (review).

Serrano-Vega et al., Conformational thermostabilization of the beta1-adrenergic receptor in a detergent-resistant form, Proceedings of the National Academy of Sciences, U.S.A., Vol. 105, No. 3, pages 877-882 (Jan. 22, 2008), relates to the conformational thermostabilization of the beta1-adrenergic receptor analyzing 318 mutants. The most stabilized variant contained six-point mutations.

Shields et al., High resolution mapping of the binding site on human IgG1 for FcγRI, FcγRII, FcγRIII, and FcRn and design of IgG1 variants with improved binding to the FcγR. Journal of Biological Chemistry 276 (9), 6591-6604 (2001).

Smith &Hegedüs, Graves' disease. N. Engl. J. Med., 375 (16), 1552-1565 (Oct. 20, 2016) provides a theoretical model of the pathogenesis of thyroid eye disease.

Stöhr et al., Predicting the relapse of hyperthyroidism in treated Graves' disease with orbitopathy by serial measurements of TSH-Receptor autoantibodies. Hormone and Metabolic Research, 53(04), 235-44 (April 2021). Decreased anti-TSHR titers following ATD treatment is associated with remission.

Strohl, Optimization of Fc-mediated effector functions of monoclonal antibodies. Current Opinion in Biotechnology, 20 (6), 685-691 (2009).

Tamm & Schmidt, IgG binding sites on human Fcγ receptors. International reviews of immunology 16 (1-2), 57-85 (1997).

Tanaka et al., Subunit structure of thyrotropin receptors expressed on the cell surface. Journal of Biological Chemistry, Volume 274, Issue 48, pages 33979-33984 (Nov. 26, 1999).

Teng et al., A strategy for the generation of biomimetic ligands for affinity chromatography. Combinatorial synthesis and biological evaluation of an IgG binding ligand, J. Mol. Recognition, 12, 67-75 (1999).

Tilman et al., Novel human IgG1 and IgG4 Fc-engineered antibodies with completely abolished immune effector functions. Protein Engineering, Design and Selection, Volume 29, Issue 10, pages 457-466 (October 2016). This paper shows that even LALA itself abolishes c1q binding. P329A alone is tested, abolishes c1q binding, and reduces FcgR binding. They show that P329G/LALA further reduces FcgR binding beyond LALA alone.

Uttamchandani et al., Microarrays of tagged combinatorial triazine libraries in the discovery of small-molecule ligands of human IgG, J. Comb. Chem., 6 (6), 862-8 (November-December 2004).

Watanabe et al., Human soluble phospholipase A2 receptor is an inhibitor of the integrin-mediated cell migratory response to collagen. Am. J. Physiol. Cell Physiol., 315, C398-C408 (2018).

Yamada et al., Angewandte Chemie Int., Ed Engl.; 58 (17), 5592-5597 (Apr. 16, 2019).

Zalevsky et al. Enhanced antibody half-life improves in vivo activity. Nature Biotechnology, 28 (2), 157-159 (2010).

TEXTBOOKS AND TECHNICAL REFERENCES

Current Protocols in Molecular Biology (CPMB), Ausubel, ed. (John Wiley and Sons, Inc., 2014).

Lewin's Genes XI, (2014). published by Jones & Bartlett Publishers.

Molecular Cloning: A Laboratory Manual, 4th ed., Michael Richard Green, and Joseph Sambrook, (Cold Spring Harbor Laboratory Press, Cold Spring Harbor, N.Y., USA, 2012).

The Merck Manual of Diagnosis and Therapy, 19th edition (Merck Sharp & Dohme Corp., 2018).

Remington's, Pharmaceutical Sciences 23rd edition (Elsevier, 2020).

Greene's Protecting Groups in Organic Synthesis, Wuts, editor (John Wiley & Sons, 2014).

Throughout this application, several publications are referenced by author name and date or by patent or patent publication number. The disclosures of these publications are incorporated in their entireties by reference into this application to describe the state of the art more fully as known to persons having ordinary skill in the biomedical art as of the date of the invention described and claimed in this specification. However, the citation of a reference in this specification should not be construed as an acknowledgment that this reference is prior art to the present invention.

All patents and publications cited throughout this specification are incorporated in their entireties by reference to disclose and describe the materials and methods that might be used with the technologies described in this specification. The publications discussed are provided only for their disclosure before the filing date. They should not be construed as an admission that the inventors may not antedate this disclosure under prior invention or for any other reason. If there is an apparent discrepancy between a prior patent or publication and the description provided in this specification, the specification (including any definitions) and claims shall control. All statements about the date or contents of these documents are based on the information available to the applicants. These statements are no admission to the correctness of the dates or contents of these documents. The publication dates in this specification may differ from the actual publication dates. If there is an apparent discrepancy between a publication date in this specification and the actual publication date supplied by the publisher, the actual publication date shall control.

---

What is claimed is:

1. A composition of matter having Formula (I):

Formula (I)

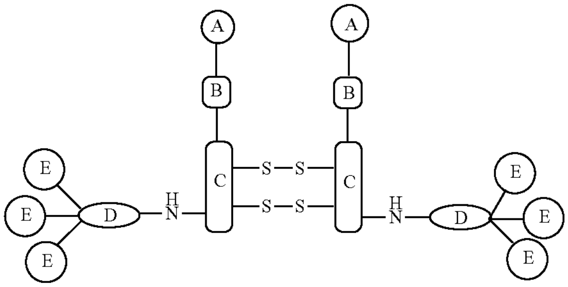

wherein, each Ⓐ is a moiety having SEQ ID NO: 7 or a TSHR antigen protein thereof, wherein the TSHR antigen protein amino acid sequence has 95% sequence identity with SEQ ID NO: 7, wherein the amino acid sequence of the TSHR antigen protein has the same numbering as SEQ ID NO: 7 according to the EU numbering scheme, wherein the differences in amino acid sequence between the sequence of SEQ ID NO: 7 and sequence of the TSHR antigen protein are due only to conservative amino acid substitutions, and wherein the TSHR antigen protein is capable of binding to anti-TSH receptor autoantibody;

each

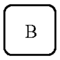

is a linking moiety connecting Ⓐ and

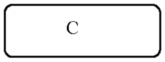;

each

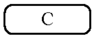

is a peptide moiety having SEQ ID NO: 8, wherein the moieties

are linked together via two disulfide bridges

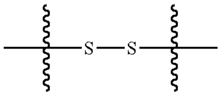

as shown in Formula (II), wherein one disulfide bridge links cysteine residues located in position 11 of SEQ ID NO: 8 of each moiety

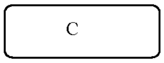, and wherein the other disulfide bridge links cysteine residues located in position 14 of SEQ ID NO: 8 of each moiety

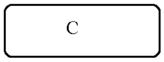;

each

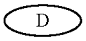

is a linker moiety connecting

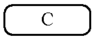

and Ⓔ wherein each

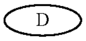

is connected to

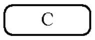

via a side chain amino group of a lysine residue of

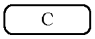

to form

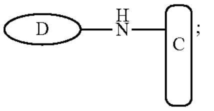

and each Ⓔ is an asialoglycoprotein receptor ("ASGPR") binding moiety comprising an N-acetyl-D-galactosamine ("GalNAc") group having Formula (II):

Formula (II)

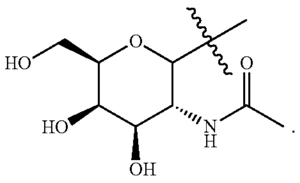

2. The composition of matter of claim 1, wherein

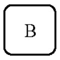

each chemical bond or a peptide connecting moiety comprising an amino acid selected from the group consisting of G, E, L, P, Q, S, and T.

3. The composition of matter of claim 1, wherein each

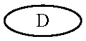

comprises a moiety selected from the group consisting of:

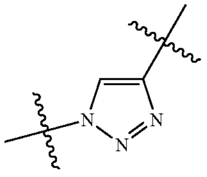
,
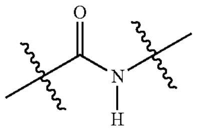
,
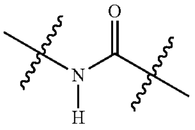
,
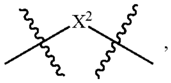
,
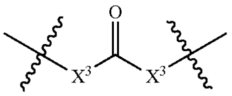
,
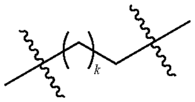
, -continued

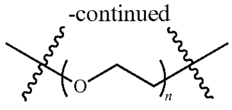

wherein, $X^2$ are independently $CH_2$, O, S, $NR^4$, C(O), S(O), $S(O)_2$, $S(O)_2O$, $OS(O)_2$, or $OS(O)_2O$;

$X^3$ are independently O, S, $NR^4$, wherein $R^4$ is H or a $C_1$-$C_3$ alkyl; and k and n are independently 1 to 25.

4. The composition of matter of claim 1, wherein each Ⓔ comprises a moiety selected from the group consisting of:

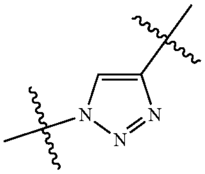
,
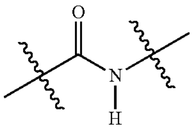
,
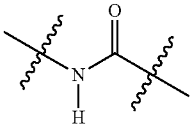
,
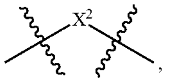
,
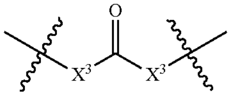
,
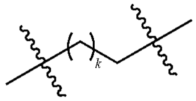
,
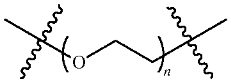

wherein, $X^2$ are independently $CH_2$, O, S, $NR^4$, C(O), S(O), $S(O)_2$, $S(O)_2O$, $OS(O)_2$, or $OS(O)_2O$;

$X^3$ are independently O, S, $NR^4$, wherein $R^4$ is H or a $C_1$-$C_3$ alkyl; and k and n are independently 1 to 25.

5. The composition of matter of claim 1, wherein each

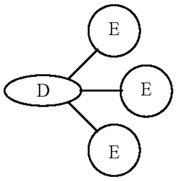

comprises a group having Formula (IV) or Formula (V):
Formula (IV)
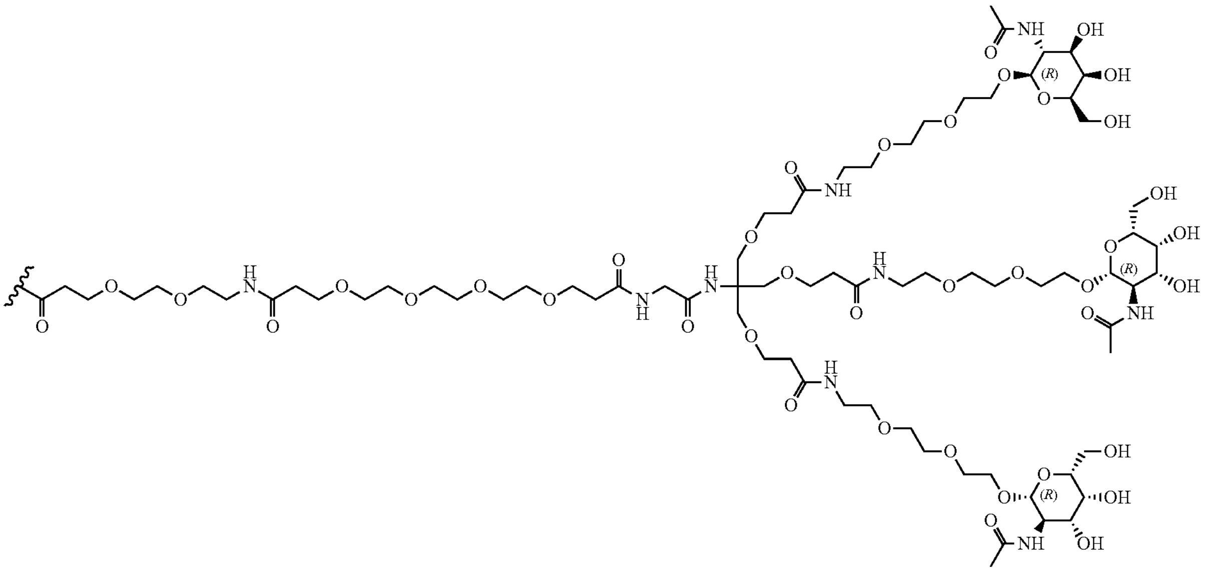
Formula (V)
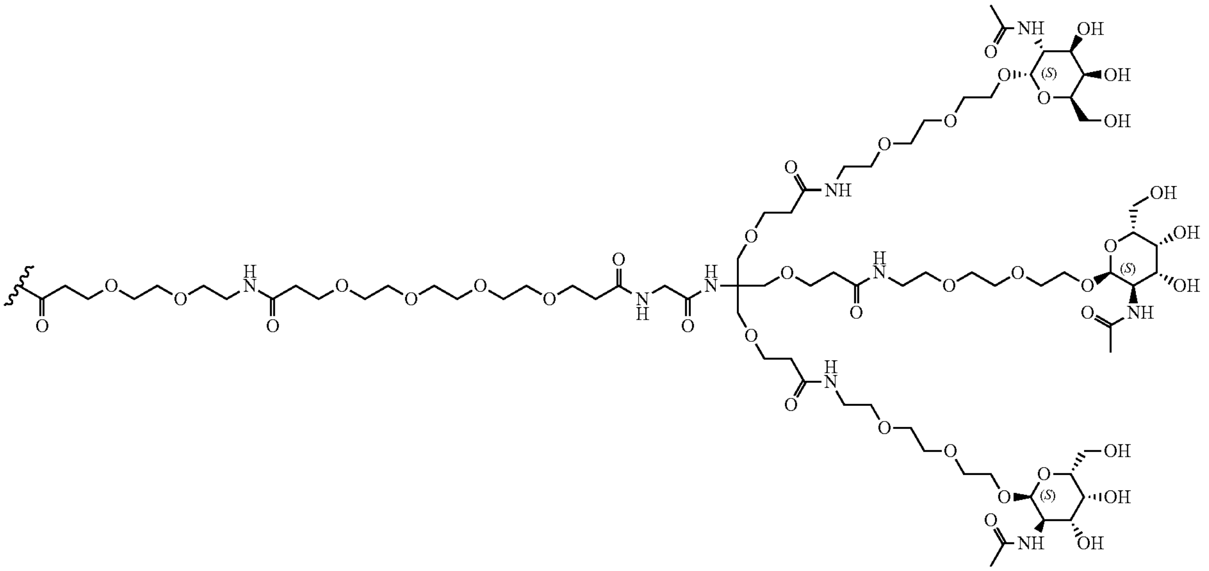
* * * * *